(12) United States Patent
Tkaczyk et al.

(10) Patent No.: US 11,168,133 B2
(45) Date of Patent: Nov. 9, 2021

(54) **COMBINATIONS OF ANTI-*STAPHYLOCOCCUS AUREUS* ANTIBODIES**

(71) Applicant: MedImmune, LLC, Gaithersburg, MD (US)

(72) Inventors: Christine Tkaczyk, Gaithersburg, MD (US); Bret Sellman, Gaithersburg, MD (US); Qun Du, Gaithersburg, MD (US); Melissa Damschroder, Gaithersburg, MD (US); Taylor Cohen, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 16/596,388

(22) Filed: Oct. 8, 2019

(65) Prior Publication Data

US 2020/0109189 A1 Apr. 9, 2020

Related U.S. Application Data

(60) Provisional application No. 62/743,490, filed on Oct. 9, 2018, provisional application No. 62/833,297, filed on Apr. 12, 2019.

(51) Int. Cl.
*C07K 16/12* (2006.01)
*A61K 38/00* (2006.01)

(52) U.S. Cl.
CPC .......... *C07K 16/1271* (2013.01); *A61K 38/00* (2013.01); *C07K 2317/24* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,596,541 B2 | 7/2003 | Murphy et al. |
| 9,527,905 B2 | 12/2016 | Sellman et al. |
| 9,845,348 B2 | 12/2017 | Sellman et al. |
| 9,879,070 B2 | 1/2018 | Sellman et al. |
| 10,457,724 B2 | 10/2019 | Sellman et al. |
| 10,730,934 B2 | 8/2020 | Sellman et al. |
| 2003/0226155 A1 | 12/2003 | Sadeghi et al. |
| 2005/0226876 A1 | 10/2005 | Graus et al. |
| 2006/0093610 A1 | 5/2006 | Lang et al. |
| 2008/0152587 A1 | 6/2008 | Zhou et al. |
| 2009/0053235 A1 | 2/2009 | Taylor et al. |
| 2009/0155164 A1 | 6/2009 | Brasel et al. |
| 2011/0274693 A1 | 11/2011 | Torres et al. |
| 2017/0129943 A1 | 5/2017 | Sellman et al. |
| 2019/0016787 A1 | 1/2019 | Sellman et al. |
| 2019/0077851 A1 | 3/2019 | Jafri et al. |
| 2020/0048330 A1 | 2/2020 | Tkaczyk et al. |
| 2020/0109190 A1 | 4/2020 | Tkaczyk et al. |

FOREIGN PATENT DOCUMENTS

| | | |
|---|---|---|
| CN | 1513874 A | 7/2004 |
| EP | 2208787 A1 | 7/2010 |
| JP | 2009539979 A | 11/2009 |
| JP | 2010538015 A | 12/2010 |
| WO | WO-2002072600 A2 | 9/2002 |
| WO | WO-2007145689 A1 | 12/2007 |
| WO | WO-2009029831 A1 | 3/2009 |
| WO | WO-2010003108 A2 | 1/2010 |
| WO | WO-2012109285 A2 | 8/2012 |
| WO | WO-2014074540 A2 | 5/2014 |
| WO | WO-2015055814 A1 | 4/2015 |
| WO | WO-2015175874 A2 | 11/2015 |
| WO | WO-2016166223 A1 | 10/2016 |
| WO | WO-2017075188 A2 | 5/2017 |
| WO | WO-2020023644 A2 | 1/2020 |
| WO | WO-2020076789 A2 | 4/2020 |
| WO | WO-2020076790 A1 | 4/2020 |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, pp. 12272-12273).*
Tkaczyk et al. (Antimicrobial Agents and Chemotherapy vol. 61 Issue 8, pp. 1-14).*
Thomsen et al. (Journal of Infectious Diseases vol. 215, pp. 1124-1131).*
Cohen, T.S, et al., *Staphylococcus aureus* drives expansion of low density neutrophils in diabetic mice, Journal of Clinical Investigation 129(5): 2133-2144, American Society for Clinical Investigation, United States (2019).
Digiandomenico, A and Sellman, B.R., "Antibacterial Monoclonal Antibodies: the Next Generation?," Current Opinion in Microbiology, 27:78-85, Current Biology, England (Aug. 2015).
Fadini, G.P., et al., "NETosis Delays Diabetic Wound Healing in Mice and Humans," Diabetes, 65(4):1061-1071, American Diabetes Association, United States (Apr. 2016).
Foletti, D., et al., "Mechanism of Action and In Vivo Efficacy of a Human-Derived Antibody against *Staphylococcus aureus* A-Hemolysin," Journal of Molecular Biology, 425(10):1641-1654, Elsevier, England (May 2013).

(Continued)

*Primary Examiner* — Robert A Zeman
(74) *Attorney, Agent, or Firm* — Sterne, Kessler, Goldstein & Fox P.L.L.C.

(57) ABSTRACT

The present disclosure is directed to anti-*Staphylococcus aureus* antibody combinations including combinations of antibodies that bind to *S. aureus* alpha toxin (AT) protein, clumping factor A protein (ClfA), and/or at least one leukotoxin protein. Methods of treating and preventing infections comprising administering the antibody combinations are also provided herein.

22 Claims, 19 Drawing Sheets

Specification includes a Sequence Listing.

(56) References Cited

OTHER PUBLICATIONS

Fridlender, Z.G., et al., "Polarization of Tumor-associated Neutrophil Phenotype by TGF-beta: "N1" versus "N2" TAN," Cancer Cell, 16(3):183-194, Cell Press, United States (Sep. 2009).

Hazenbos, W.L., et al., "Novel Staphylococcal Glycosyltransferases Sdga and Sdgb Mediate Immunogenicity and Protection of Virulence-associated Cell Wall Proteins," PLOS Pathogens, 9(10):e1003653, Public Library of Science, United States (2013).

Hua, L., et al., "Assessment of an Anti-Alpha-Toxin Monoclonal Antibody for Prevention and Treatment of *Staphylococcus aureus*-Induced Pneumonia," Antimicrobial Agents and Chemotherapy, 58(2):1108-1117, American Society for Microbiology, United States (2014).

Karauzum, H., et al., "Synthetic Human Monoclonal Antibodies toward Staphylococcal Enterotoxin B (Seb) Protective against Toxic Shock Syndrome," Journal of Molecular Biology, 287(30):25203-25215, American Society for Biochemistry and Molecular Biology, United States (Jul. 2012).

Kelly, A., et al., "Human Monocytes and Macrophages Regulate Immune Tolerance via Integrin Avβ8-mediated TGFβ Activation," Journal of Experimental Medicine, 215(11):2725-2736, Rockefeller University Press, United States (Nov. 2018).

Lowy, F.D., "*Staphylococcus aureus* Infections," The New England Journal of Medicine, 339(8):520-532, Massachusetts Medical Society, United States (Aug. 1998).

Powers, M.E., et al., "Synergistic Action of *Staphylococcus aureus* α-Toxin on Platelets and Myeloid Lineage Cells Contributes to Lethal Sepsis," Cell Host & Microbe, 17(6):775-787, Cell Press, United States (Jun. 2015).

Rouha, H., et al., "Five Birds, One Stone: Neutralization of A-hemolysin and 4 Bi-component Leukocidins of *Staphylococcus aureus* with a Single Human Monoclonal Antibody," MAbs, 7(1):243-254, Taylor & Francis, United States (2015).

Sagiv, J.Y., et al., "Phenotypic Diversity and Plasticity in Circulating Neutrophil Subpopulations in Cancer," 10(4):562-573, Cell Press, United States (Feb. 2015).

Surewaard, B.G.J., et al., "α-Toxin Induces Platelet Aggregation and Liver Injury during *Staphylococcus aureus* Sepsis," Cell Host & Microbe, 24(2):271-284, Cell Press, United States (Aug. 2018).

Travis, M.A., et al., "Loss of Integrin Alpha(V)beta8 on Dendritic Cells Causes Autoimmunity and Colitis in Mice," Nature, 449(7160):361-365, Nature Publishing Group, England (Sep. 2007).

Tsuda, Y., et al., "Three Different Neutrophil Subsets Exhibited in Mice With Different Susceptibilities to Infection by Methicillin-resistant *Staphylococcus aureus*," Immunity, 21(2):215-226, Cell Press, United States (Aug. 2004).

Villanueva, E., et al., "Netting Neutrophils Induce Endothelial Damage, Infiltrate Tissues, and Expose Immunostimulatory Molecules in Systemic Lupus Erythematosus," Journal of Immunology, 187(1):538-552, American Association of Immunologists, United States (Jul. 2011).

Wong, S.L., et al., "Diabetes Primes Neutrophils to Undergo NETosis, Which Impairs Wound Healing," Nature Medicine, 21(7):815-819, Nature Publishing Company, United States (Jul. 2015).

Co-Pending U.S. Appl. No. 16/596,445, filed Oct. 8, 2019, inventor Tkaczyk, C., et al., (Unpublished).

Co-Pending U.S. Appl. No. 16/599,595, filed Oct. 11, 2019, inventor Sellman, B., et al., (Unpublished).

Adhikari, R. P., et al., "Antibodies to *S. aureus* LukS-PV Attenuated Subunit Vaccine Neutralize a Broad Spectrum of Canonical and Non-Canonical Bicomponent Leukotoxin Pairs," PLoS One 10(11):e0137874, 17 pages, Public Library of Science, United States (2015).

Al-Lazikani, B., et al., "Standard conformations for the canonical structures of immunoglobulins," Journal of Molecular Biology 273(4):927-948, Elsevier, United Kingdom (Nov. 1997).

Alonzo, F., III and Torres, V.J., "Bacterial Survival Amidst an Immune Onslaught: the Contribution of the *Staphylococcus aureus* Leukotoxins," PLoS Pathogens 9(2):e1003143, 4 pages, Public Library of Science, United States (Feb. 2013).

Bhakdi, S., et al., "Alpha-toxin of *Staphylococcus aureus*," Microbiological Reviews 55(4):733-751, American Society for Microbiology, United States (1991).

Blomqvist, L., and Sjogren, A., "Production and characterization of monoclonal antibodies against *Staphylococcus aureus* alpha-toxin," Toxicon 26(3):265-273, Elsevier, United Kingdom (1988).

Borrok, M.J., et al., "pH-dependent Binding Engineering Reveals an FcRn Affinity Threshold That Governs IgG Recycling," The Journal of Biological Chemistry 290(7):4282-4290, American Society for Biochemistry and Molecular Biology, United States (2015).

Brown, M., et al., "Tolerance to Single, but not Multiple, Amino Acid Replacements in Antibody VH CDR2: A Means of Minimizing B Cell Wastage from Somatic Hypermutation?," Journal of Immunology 156(9):3285-3291, American Association of Immunologists, United States (May 1996).

Cheung, G.Y.C, and Otto, M., "The potential use of toxin antibodies as a strategy for controlling acute *Staphylococcus aureus* infections," Expert Opinion on Therapeutic Targets, 16(6):601-612, Ashley Publications, United Kingdom (Jun. 2012).

Coloma, M.J. and Morrison, S.L., "Design and Production of Novel Tetravalent Bispecific Antibodies," Nature Biotechnology 15(2):159-163, Nature America Publishing, United States (Feb. 1997).

Dimasi, N., et al., "The Design and Characterization of Oligospecific Antibodies for Simultaneous Targeting of Multiple Disease Mediators," Journal of Molecular Biology 393(3):672-692, Elsevier, United Kingdom (Aug. 2009).

Gershoni, J.M., et al., "Epitope Mapping: the First Step in Developing Epitope-based Vaccines," BioDrugs 21(3):145-156, Springer International, New Zealand (2007).

Gouaux, E., et al., "alpha-Hemolysin, gamma-hemolysin, and leukocidin from *Staphylococcus aureus*: distant in sequence but similar in structure," Protein Science 6(12):2631-2635, Cold Spring Harbor Laboratory Press, United States (Dec. 1997).

Harshman, S., et al, "Staphylococcal alpha-toxin: a structure-function study using a monoclonal antibody," Toxicon 24(4):403-411, Elsevier, United Kingdom (1986).

Hilliard, J.J., et al., "Anti-alpha-toxin monoclonal antibody and antibiotic combination therapy improves disease outcome and accelerates healing in a *Staphylococcus aureus* dermonecrosis model," Antimicrobial Agents and Chemotherapy 59(1):299-309, American Society for Microbiology, United States (Jan. 2015).

International Search Report and Written Opinion for International Application No. PCT/US2012/024201, European Patent Office, Netherlands, dated Jul. 27, 2012, 18 pages.

International Search Report and Written Opinion for International Application No. PCT/US2019/043254, European Patent Office, Netherlands, dated Feb. 13, 2020, 17 pages.

International Search Report and Written Opinion for International Application No. PCT/US2019/055143, European Patent Office, Netherlands, dated Sep. 23, 2020, 22 pages.

International Search Report and Written Opinion in International Application No. PCT/US2019/055144, European Patent Office, Netherlands, dated Jan. 20, 2020, 13 pages.

Laventie, B.J., et al., "Heavy chain-only antibodies and tetravalent bispecific antibody neutralizing *Staphylococcus aureus* leukotoxins," Proceedings of the National Academy of Sciences of the United States of America 108(39):16404-16409, National Academy of Sciences, United States (Sep. 2011).

Meesters, C., et al., "Structural characterization of the alpha-hemolysin monomer from *Staphylococcus aureus*," Proteins 75(1):118-126, Wiley-Liss, United States (Apr. 2009).

Mendes, R.E., et al., "Characterization of methicillin-resistant *Staphylococcus aureus* strains recovered from a phase IV clinical trial for linezolid versus vancomycin for treatment of nosocomial pneumonia," Journal of Clinical Microbiology 50(11):3694-3702, American Society for Microbiology, United States (Nov. 2012).

Monnet, C., et al., "Selection of IgG Variants with Increased FcRn Binding Using Random and Directed Mutagenesis: Impact on Effector Functions," Frontiers in Immunology 6:39, 1-14, Frontiers Research Foundation, Switzerland (Feb. 2015).

(56) References Cited

OTHER PUBLICATIONS

Oganesyan, V., et al., "Mechanisms of neutralization of a human anti-α-toxin antibody," The Journal of Biological Chemistry 289(43):29874-29880, American Society for Biochemistry and Molecular Biology, United States (2014).

Ohno, S., et al., "Antigen-binding specificities of antibodies are primarily determined by seven residues of $V_H$," Proc Natl Acad Sci USA 82:2945-2949, National Academy of Science, United States (1985).

Ortines, R.V., et al., "Neutralizing Alpha-Toxin Accelerates Healing of *Staphylococcus aureus*-Infected Wounds in Nondiabetic and Diabetic Mice," Antimicrobial Agents and Chemotherapy 62(3):e02288-17, 14 pages, American Society for Microbiology, United States (Mar. 2018).

Ortines, R.V., et al., "Efficacy of a Multimechanistic Monoclonal Antibody Combination against *Staphylococcus aureus* Surgical Site Infections in Mice," Antimicrobial Agents and Chemotherapy 63(8):e00346-19, 6 pages, American Society for Microbiology, United States (Jul. 2019).

Ragle, B.E., and Wardenburg, J.B., "Anti-alpha-hemolysin monoclonal antibodies mediate protection against *Staphylococcus aureus* pneumonia," Infect Immun 77(7):2712-2718, American Society for Microbiology, United States (2009).

Rudikoff, S., et al., "Single amino acid substitution altering antigen-binding specificity," Proc Natl Acad Sci USA 79:1979-1983, National Academy of Science, United States (1982).

Sharma-Kuinkel, B. K., "Characterization of alpha-toxin hla gene variants, alpha-toxin expression levels, and levels of antibody to alpha-toxin in hemodialysis and postsurgical patients with *Staphylococcus aureus* bacteremia," Journal of Clinical Microbiology 53(1):227-236, American Society for Microbiology, United States (2015).

Song, L., et al., "Structure of Staphylococcal α-Hemolysin, a Heptameric Transmembrane Pore," Science 274(5294):1859-1866, American Association for the Advancement of Science, United States (Dec. 1996).

Tkaczyk, C., et al., "Identification of anti-alpha toxin monoclonal antibodies that reduce the severity of *Staphylococcus aureus* dermonecrosis and exhibit a correlation between affinity and potency," Clin Vaccine Immunol 19(3):377-385, American Society for Microbiology, United States (2012).

Tkaczyk, C., et al., "Targeting Alpha Toxin and ClfA with a Multimechanistic Monoclonal-Antibody-Based Approach for Prophylaxis of Serious *Staphylococcus aureus* Disease," mBio 7(3):e00528-16, 11 pages, American Society for Microbiology, United States (May-Jun. 2016).

Tkaczyk, C., "Antibacterial monoclonal antibodies: A strategy to prevent serious bacterial infections," presented at the Society for Laboratory Automation and Screening on Feb. 4, 2019, retrieved from the Internet: https://www.eventscribe.com/2019/SLAS2019/fsPopup.asp?efp=V01VQUNFW1A2OTg4&PresentationID=466606&rnd=9.235436E-02&mode=presinfo on Jul. 15, 2020, 2 pages.

Traggiai, E., et al., "An efficient method to make human monoclonal antibodies from memory B cells: potent neutralization of SARS coronavirus," Nature Medicine 10(8): 871-875, Nature Publishing Group, United Kingdom (2004).

Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, United Kingdom (Jul. 2002).

Walker, B., and Bayley, H., "Key residues for membrane binding, oligomerization, and pore forming activity of Staphylococcal alpha-hemolysin identified by cysteine scanning mutagenesis and targeted chemical modification," The Journal of Biological Chemistry 270(39):23065-23071, The American Society for Biochemistry and Molecular Biology Inc., United States (1995).

Wardenburg, J.B., and Schneewind, O., "Vaccine protection against *Staphylococcus aureus* pneumonia," J Exp Med 205:287-294, Rockefeller University Press, United States (2008).

Wilke, G., et al., "Role of a disintegrin and metalloprotease 10 in *Staphylococcus aureus* alpha-hemolysin-mediated cellular injury," Proc Natl Acad Sci USA 107(30):13473-13478, National Academy of Science, United States (2010).

Yanjie, M., et al., "713. Preventive Administration of MEDI6389, a Combination of Monoclonal Antibodies (mAbs) Targeting Alpha-Toxin (AT), Panton-Valentine Leukocidin (PVL), Leukocidin Ed (LukED), Gamma-Hemolysin and Clumping Factor A (ClfA), in a Rabbit Model of USA300 MRSA Prosthetic Joint Infection (PJI)," Open Forum Infectious Diseases 6(Suppl 2):S320-S321, Oxford University Press, United Kingdom (Oct. 2019).

Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (2009).

Yu, X-Q., et al., "Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrob Agents Chemother 61(1):e01020-16, 9 pages, American Society for Microbiology, United States (Jan. 2017).

Office Action dated Sep. 25, 2020 in U.S. Appl. No. 16/521,223, inventors Tkaczyk, C., et al., filed Jul. 24, 2019, 15 pages.

\* cited by examiner

Figure 1
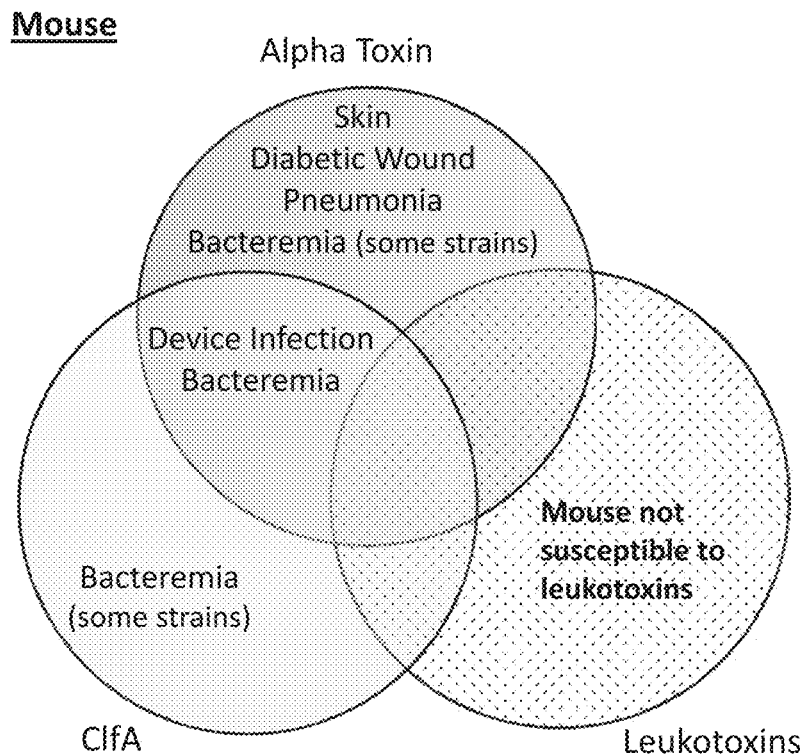
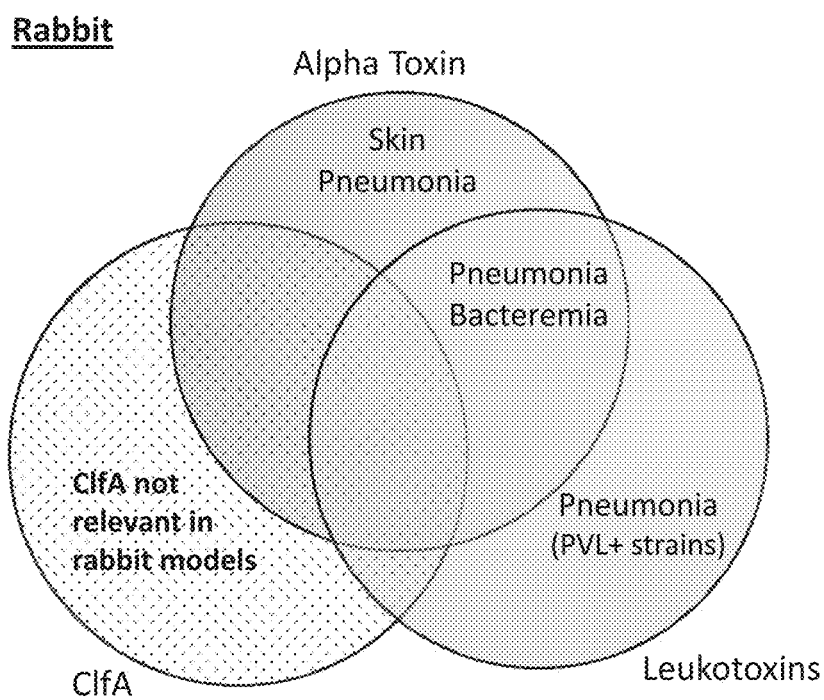

Figure 5
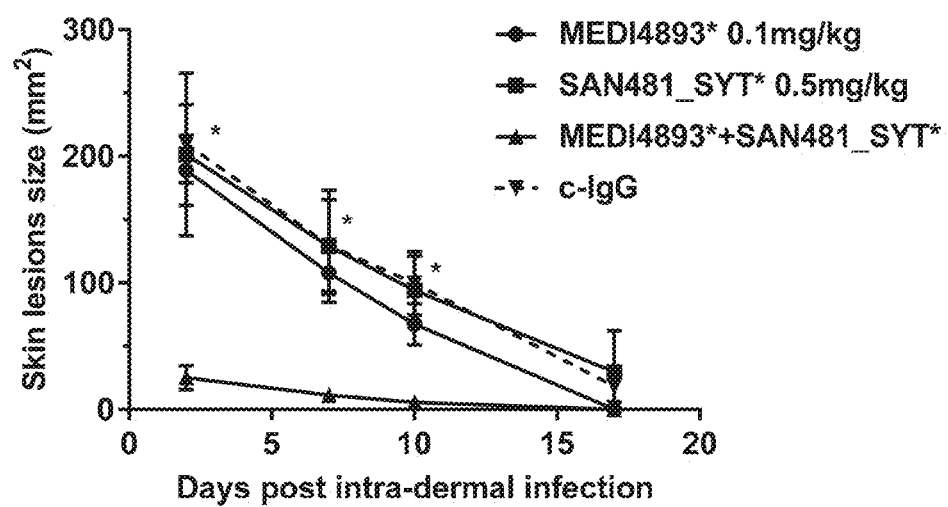
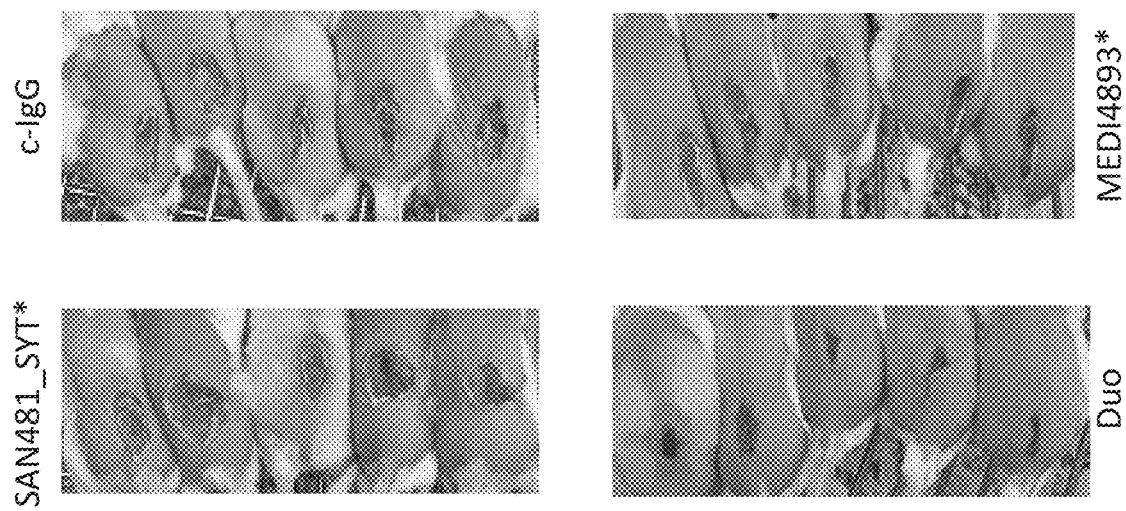

Figure 6
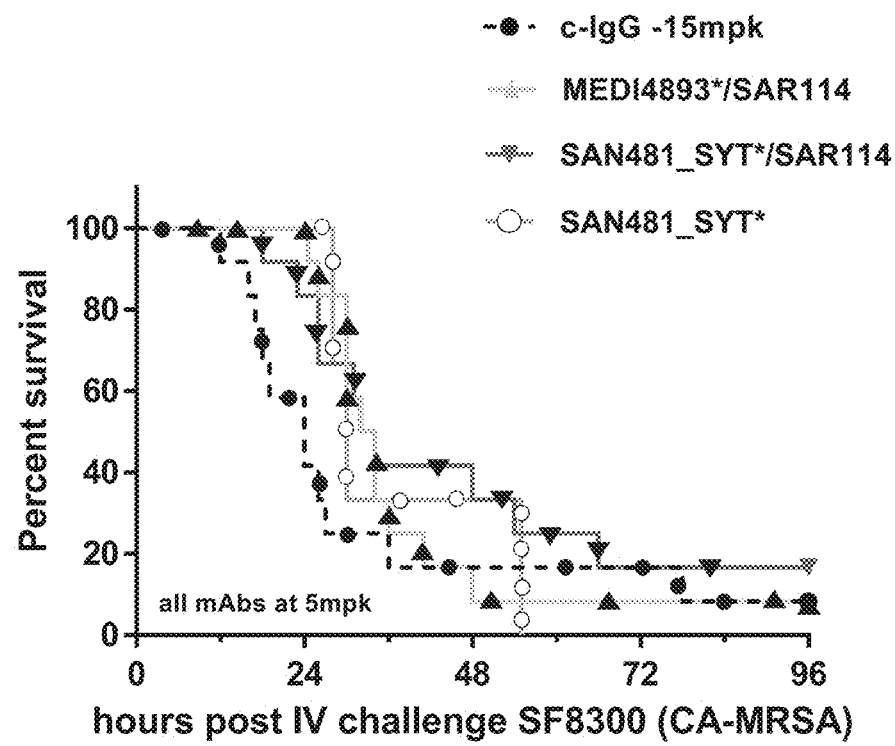
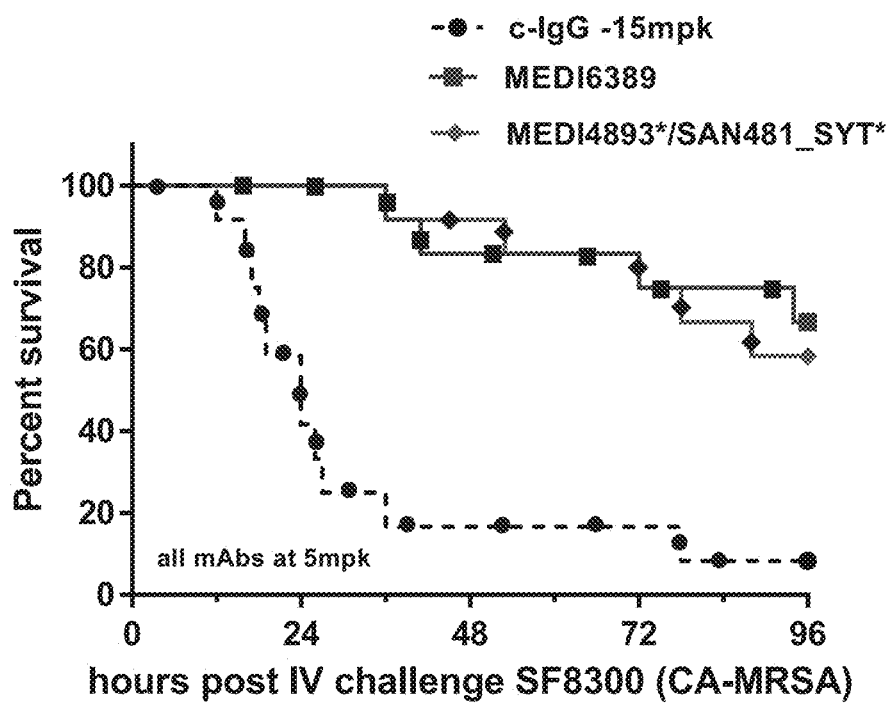

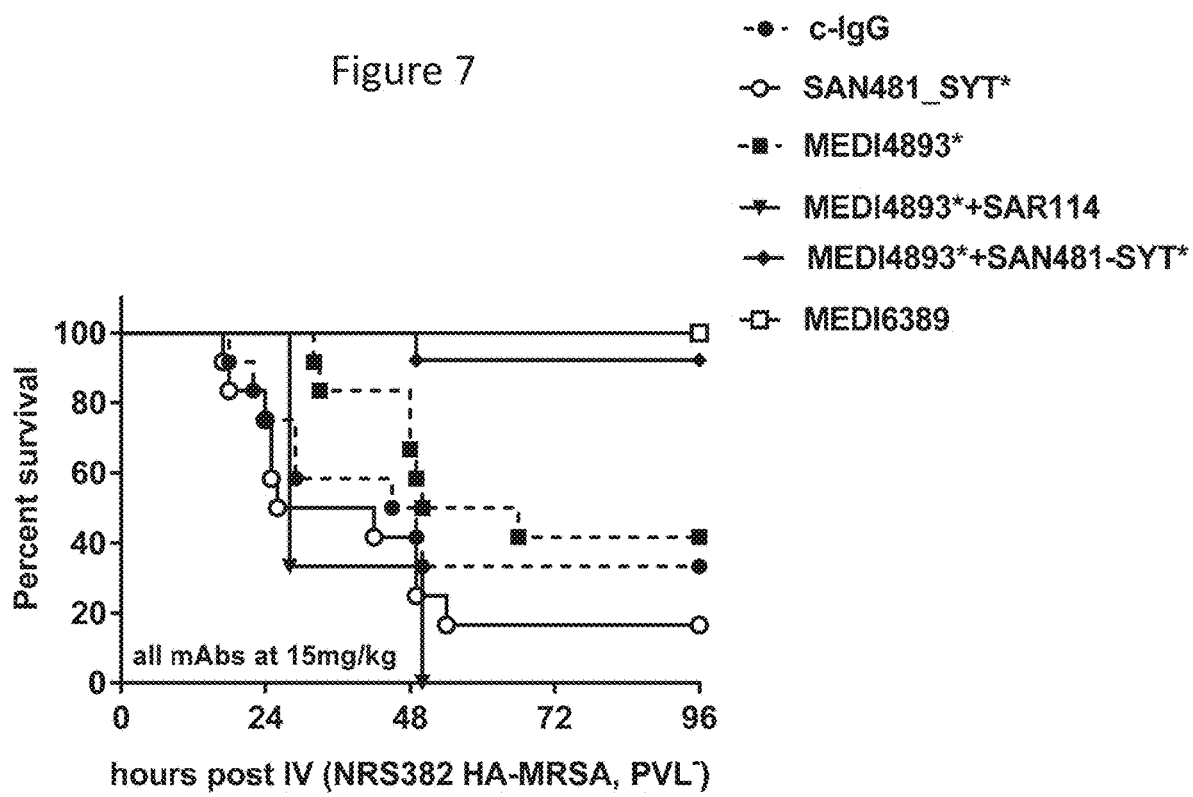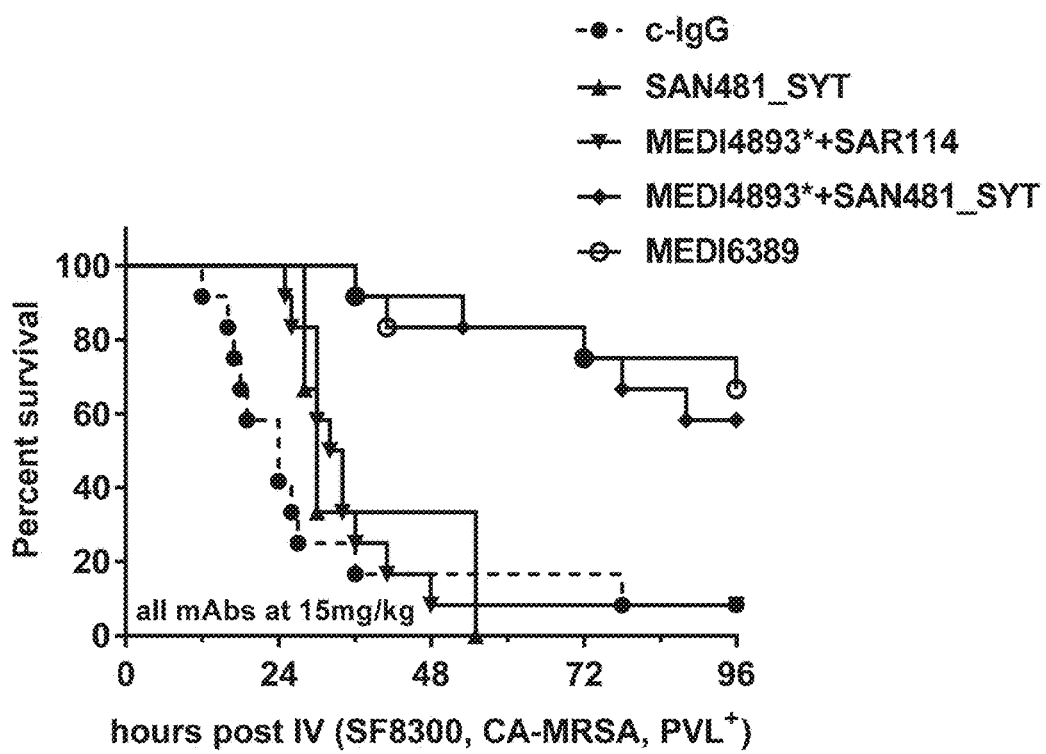
Figure 7

Figure 8
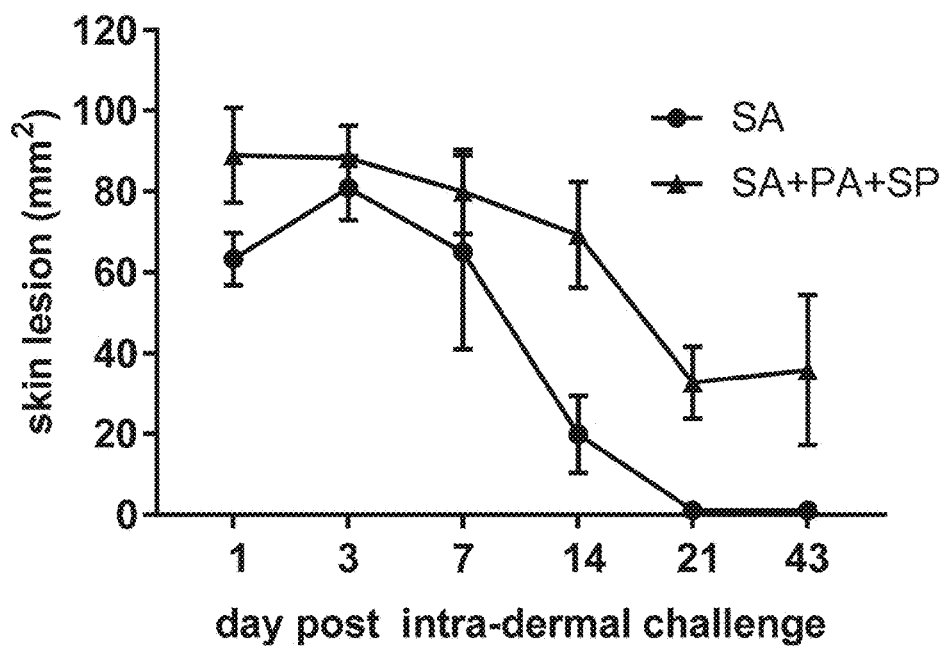

Figure 9
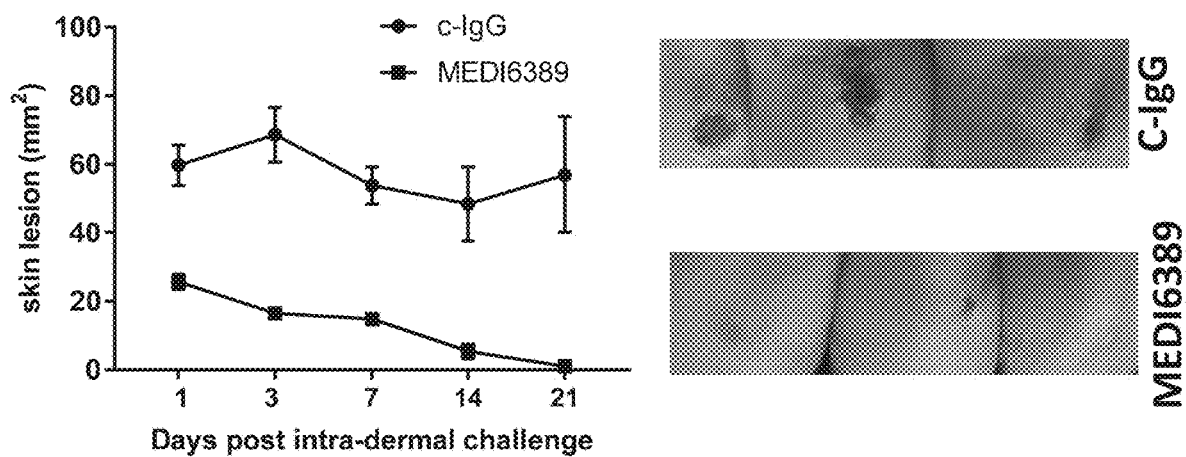
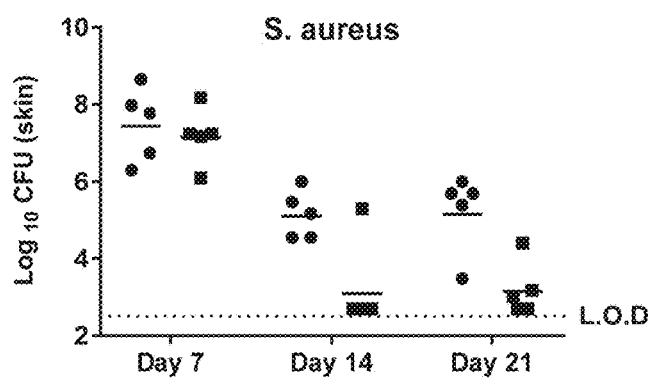
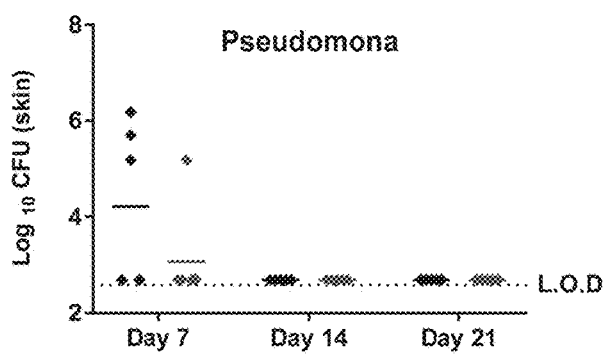
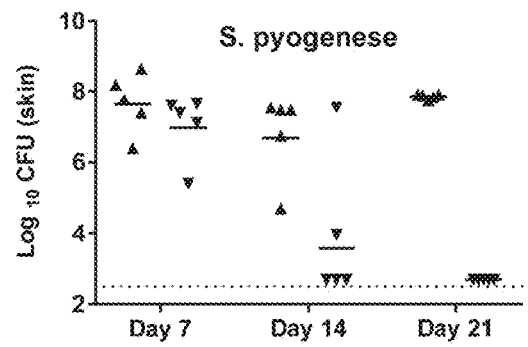

Figure 10

```
HlgB   GEGKITPVSVKKVDDKVTLYKTTATADSDKFKISQILTFNFIKDKSYDKDTIVLKATGNI   60
LukF   GAQHITPVSEKKVDDKITLYKTTATSDSDKLKISQILTFNFIKDKSYDKDTLILKAAGNI   60
LukD   GAQHITPVSEKKVDDKITLYKTTATSDNDKLNISQILTFNFIKDKSYDKDTIVLKAAGNI   60
       * :: ****.:* *******:**** ******:.****:****:********::**** :***:

HlgB   NSGFVKPNPNDYDFSKLYWGAKYNVSISSQSNDSVNVVDYAPKNQNEEFQVQNTLGYTFG   120
LukF   YSGYTKPNPKDTISSQFYWGSKYNISINSDSNDSVNVVDYAPKNQNEEFQVQQTVGYSYG   120
LukD   NSGYKKPNPKDYNYSQFYWGGKYNVSVSSESNDAVNVVDYAPKNQNEEFQVQQTLGYSYG   120
       ** *:**::: *.:***.**:*:.:.*::***:*************:*:.**::*

HlgB   GDISISNGLSGGLNGNTAFSETINYKQESYRTTLSRNTNYKNVGWGVEAHKIMNNGWGPY   180
LukF   GDINISNGLSGGNGSKSFSETINYKQESYRTSLDKRTNFKKIGWDVEAHKIMNNGWGPY   180
LukD   GDINISNGLSGGLNGSKSFSETINYKQESYRTTIDRKTNHKSIGWGVEAHKIMNNGWGPY   180
       ***:*******  .:.:.:************: ::: **:*.:**.*************

HlgB   GRDSFHPTYGNELFLAGRQSSAYAGQNFIAQHQMPLLSRSNFNPEFLSVLSHRQDGAKKS   240
LukF   GRDSYHSTYGNEMFLGSRQSNLNAGQNFLEYHKMPVLSRGNFNPEFIGVLSRKQNAAKKS   240
LukD   GRDSYDPTYGNELFLGGRQSSNAGQNFLPTHQMPLLARGNFNPEFISVLSHKQNDTKKS   240
       ****:: ****:**..:**. ::*****  :*:**:*:.*******:.***::*: :***

HlgB   KITVTYQREMDLYQIRWNGFYWAGANYKNFKTRTFKSTYEIDWENHKVKLLDTKETENNK   300
LukF   KITVTYQREMDRYTNFWNQLHWIGNNYKDENRATHTSIYEVDWENHTVKLIDTQSKEKNP   300
LukD   KIKVTYQREMDRYTNQWNRLHWVGNNYKNQNTVTFTSTYEVDWQNHTVKLIGTDSKETNP   300
       ** ********  *: :*: **.*:***::  .: : ::***:**:** ***:.:.**

HlgB   -- 300
LukF   MS 302
LukD   GV 302
       *.
```

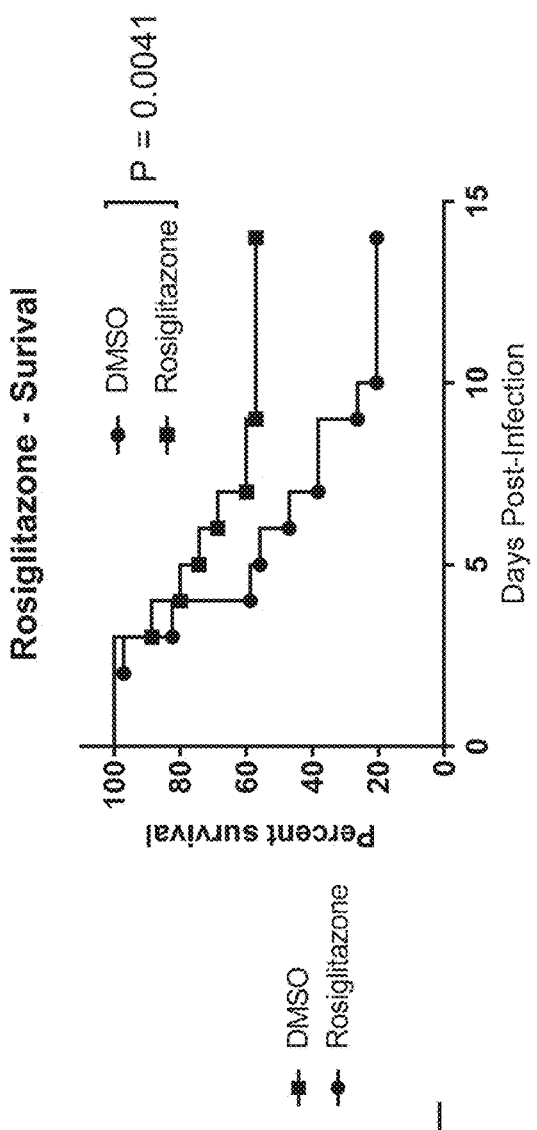
Figure 11E
Figure 11F
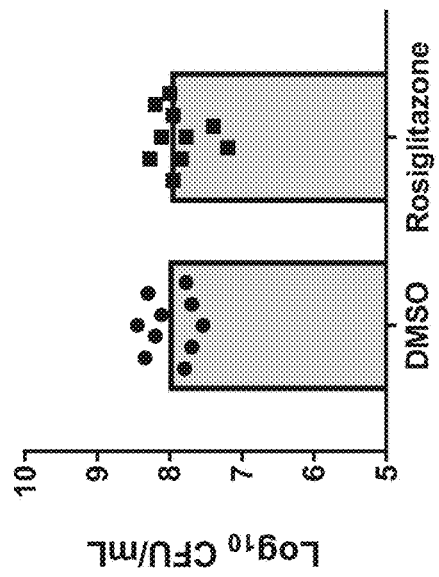
Figure 11G

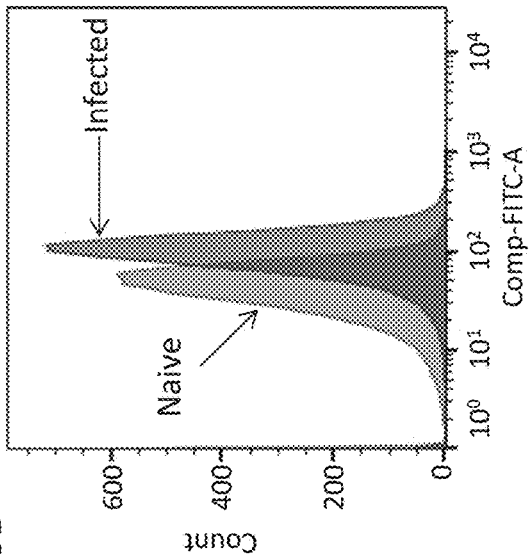
Figure 16A
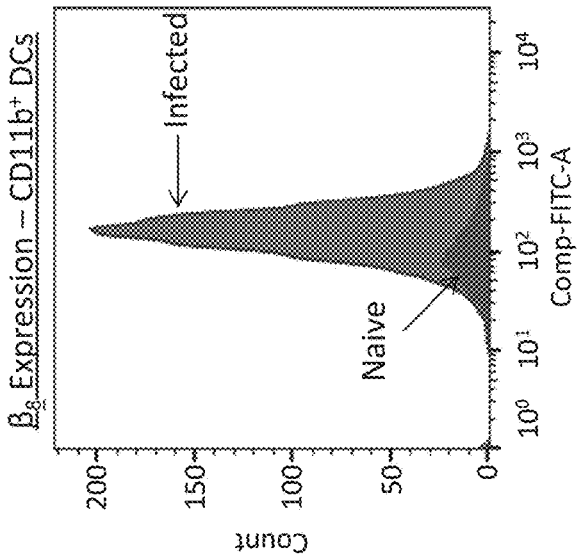
Figure 16B
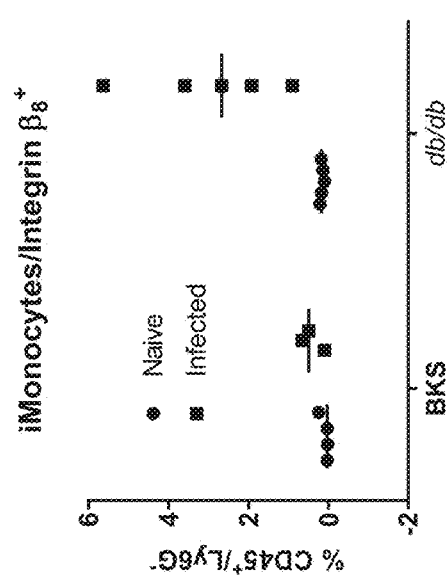
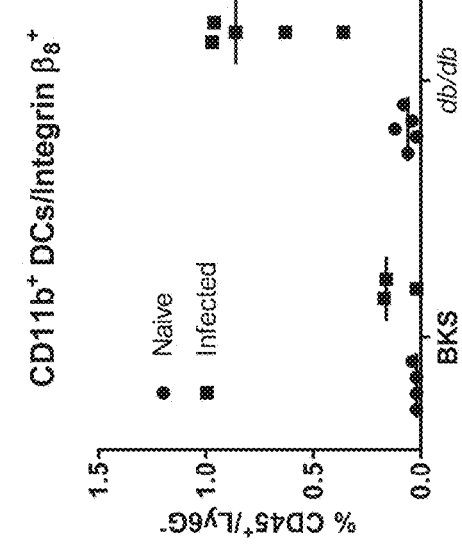

```
                          SEQUENCE LISTING

<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: VH CDR1

<400> SEQUENCE: 1

Ser His Asp Met His
1               5

<210> SEQ ID NO 2
<211> LENGTH: 16
<212> TYPE: PRT
<213> ORGANISM: Artificial Sequence
<220> FEATURE:
<223> OTHER INFORMATION: VH CDR2

<400> SEQUENCE: 2

Gly Ile Gly Thr Ala Gly Asp Thr Tyr Tyr Pro Asp Ser Val Lys Gly
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: VH CDR3

<400> SEQUENCE: 3

Asp Arg Tyr Ser Pro Thr Gly His Tyr Tyr Gly Met Asp Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: VH CDR1

<400> SEQUENCE: 4

Asn Ser Tyr Trp Ser
1               5

<210> SEQ ID NO 5
<211> LENGTH: 16
<212> TYPE: PRT
<213> ORGANISM: Artificial Sequence
<220> FEATURE:
<223> OTHER INFORMATION: VH CDR2

<400> SEQUENCE: 5

Tyr Leu Tyr Ser Ser Gly Arg Thr Asn Tyr Thr Pro Ser Leu Lys Ser
1               5                   10                  15

<210> SEQ ID NO 6
<211> LENGTH: 16
<212> TYPE: PRT
<213> ORGANISM: Artificial Sequence
```

```
<220> FEATURE:
<223> OTHER INFORMATION: VH CDR3

<400> SEQUENCE: 6

Thr His Leu Gly Gly Phe His Tyr Gly Gly Phe Trp Phe Asp Pro
1               5                   10                  15

<210> SEQ ID NO 7
<211> LENGTH: 5
<212> TYPE: PRT
<213> ORGANISM: Artificial Sequence
<220> FEATURE:
<223> OTHER INFORMATION: VH CDR1

<400> SEQUENCE: 7

Thr Tyr Ala Met His
1               5

<210> SEQ ID NO 8
<211> LENGTH: 17
<212> TYPE: PRT
<213> ORGANISM: Artificial Sequence
<220> FEATURE:
<223> OTHER INFORMATION: VH CDR2

<400> SEQUENCE: 8

Val Thr Ser Phe Asp Gly Ser Asn Glu Tyr Tyr Ile Asp Ser Val Lys
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: VH CDR3

<400> SEQUENCE: 9

Asp Glu Tyr Thr Gly Gly Trp Tyr Ser Val Gly Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: VL CDR1

<400> SEQUENCE: 10

Arg Ala Ser Gln Ser Ile Ser Ser Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: VL CDR2

<400> SEQUENCE: 11

Lys Ala Ser Ser Leu Glu Ser
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: VL CDR3

<400> SEQUENCE: 12

Lys Gln Tyr Ala Asp Tyr Trp Thr
1               5

<210> SEQ ID NO 13
<211> LENGTH: 11
<212> TYPE: PRT
<213> ORGANISM: Artificial Sequence
<220> FEATURE:
<223> OTHER INFORMATION: VL CDR1

<400> SEQUENCE: 13

Arg Ala Ser Gln Ser Ile Thr Ser Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: VL CDR2

<400> SEQUENCE: 14

Ala Ser Ser Ser Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: VL CDR3

<400> SEQUENCE: 15

Gln Glu Ser Tyr Ser Thr Pro Pro Thr
1               5

<210> SEQ ID NO 16
<211> LENGTH: 13
<212> TYPE: PRT
<213> ORGANISM: Artificial Sequence
<220> FEATURE:
<223> OTHER INFORMATION: VL CDR1

<400> SEQUENCE: 16

Ser Gly Ser Ser Tyr Asn Ile Gly Ser Asn Tyr Val Tyr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: VL CDR2

<400> SEQUENCE: 17

Arg Ser Ile Gln Arg Pro Ser
1               5
```

```
<210> SEQ ID NO 18
<211> LENGTH: 11
<212> TYPE: PRT
<213> ORGANISM: Artificial Sequence
<220> FEATURE:
<223> OTHER INFORMATION: VL CDR3

<400> SEQUENCE: 18

Ala Ala Trp Asp Asp Ser Leu Arg Ala Trp Val
1               5                   10

<210> SEQ ID NO 19
<211> LENGTH: 122
<212> TYPE: PRT
<213> ORGANISM: Artificial Sequence
<220> FEATURE:
<223> OTHER INFORMATION: VH Amino Acid Sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: VH Amino Acid Sequence

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Asn Ser
            20                  25                  30

Tyr Trp Ser Trp Ile Arg Gln Pro Pro Gly Lys Gly Leu Glu Trp Ile
        35                  40                  45

Gly Tyr Leu Tyr Ser Ser Gly Arg Thr Asn Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr His Leu Gly Gly Phe His Tyr Gly Gly Phe Trp Phe Asp
            100                 105                 110

Pro Trp Gly Gln Gly Thr Leu Val Thr Val Ser Ser
        115                 120
```

```
<210> SEQ ID NO 21
<211> LENGTH: 126
<212> TYPE: PRT
<213> ORGANISM: Artificial Sequence
<220> FEATURE:
<223> OTHER INFORMATION: VH Amino Acid Sequence

<400> SEQUENCE: 21

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Ser Phe Arg Asn Ala
            20                  25                  30

Leu Met Ser Trp Val Arg Gln Ala Pro Gly Lys Gly Leu Glu Trp Val
        35                  40                  45

Gly Arg Ser Lys Thr Asp Gly Thr Thr Asp Tyr Ala Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Pro Gly Gly Pro Pro Gly Asp Tyr Tyr Tyr Asp Gly
            100                 105                 110

Met Asp Val Trp Gly Gln Gly Thr Thr Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: VH Amino Acid Sequence

<400> SEQUENCE: 22

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Thr Trp Val Arg Gln Ala Pro Gly Lys Gly Leu Glu Trp Val
        35                  40                  45

Gly Arg Ile Arg Ser Lys Thr Ala Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Thr Ser Leu Lys Ile Glu Asp Thr Ala Leu Tyr
                85                  90                  95

Tyr Cys Met Thr Asp Gly Leu Gly Leu Leu Asn Phe Gly Asp Ser Asp
            100                 105                 110

Pro His His Tyr Trp Gly Gln Gly Thr Arg Val Thr Val Ser Ser
        115                 120                 125

<210> SEQ ID NO 23
<211> LENGTH: 122
<212> TYPE: PRT
<213> ORGANISM: Artificial Sequence
<220> FEATURE:
<223> OTHER INFORMATION: VH Amino Acid Sequence
<220> FEATURE:
<221> NAME/KEY: misc_feature
<222> LOCATION: (25)..(25)
<223> OTHER INFORMATION: Xaa can be any naturally occurring amino acid
```

```
<220> FEATURE:
<221> NAME/KEY: misc_feature
<222> LOCATION: (28)..(28)
<223> OTHER INFORMATION: Xaa can be any naturally occurring amino acid

<400> SEQUENCE: 23

Glu Val Gln Leu Val Gln Ser Gly Ala Glu Val Lys Lys Pro Gly Glu
1               5                   10                  15

Ser Leu Lys Ile Ser Cys Lys Ala Xaa Gly Tyr Xaa Phe Thr Ser Tyr
                20                  25                  30

Trp Ile Gly Trp Val Arg Gln Val Pro Gly Lys Gly Leu Glu Trp Met
            35                  40                  45

Gly Ile Ile Tyr Pro Gly Asp Ser Asp Thr Arg His Ser Pro Ser Phe
        50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Ser Ala Met Tyr Tyr Cys
                85                  90                  95

Ala Arg His Gln Ser Gly Ser His Gly Phe Asp Ala Phe Glu Ile Trp
            100                 105                 110

Gly Gln Gly Thr Met Val Thr Val Ser Ser
            115                 120

<210> SEQ ID NO 24
<211> LENGTH: 119
<212> TYPE: PRT
<213> ORGANISM: Artificial Sequence
<220> FEATURE:
<223> OTHER INFORMATION: VH Amino Acid Sequence

<400> SEQUENCE: 24

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Ser Gly Asp Ser Asp Thr Arg Tyr Ser Pro Ser Phe
        50                  55                  60

Leu Gly Gln Val Ser Ile Ser Val Asp Lys Ser Phe Thr Thr Ala Tyr
65                  70                  75                  80

Leu Gln Trp Arg Ser Leu Lys Ala Ser Asp Thr Ala Met Tyr Tyr Cys
                85                  90                  95

Ala Arg Arg Pro Gly Gly Gln Lys Pro Tyr Asp Tyr Trp Gly Gln Gly
            100                 105                 110

Thr Leu Val Thr Val Ser Ser
        115

<210> SEQ ID NO 25
<211> LENGTH: 136
<212> TYPE: PRT
<213> ORGANISM: Artificial Sequence
<220> FEATURE:
<223> OTHER INFORMATION: VH Amino Acid Sequence
```

<400> SEQUENCE: 25

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asn Ala
            20                  25                  30

Trp Met Ser Trp Val Arg Gln Ala Pro Gly Lys Gly Leu Glu Trp Val
        35                  40                  45

Gly Arg Ile Lys Ser Glu Thr Ala Gly Gly Thr Thr Asp Tyr Ala Ala
    50                  55                  60

Pro Val Lys Gly Arg Phe Ser Ile Ser Arg Asp Asp Ser Arg Asn Thr
65                  70                  75                  80

Leu Tyr Leu Glu Met Asn Ser Leu Lys Thr Glu Asp Thr Ala Val Tyr
                85                  90                  95

Tyr Cys Thr Thr Asp Ser Tyr Thr Pro Leu Glu Pro Cys Pro Asn
            100                 105                 110

Gly Val Cys Tyr Thr Tyr Tyr Tyr Gly Met Asp Val Trp Gly Gln
            115                 120                 125

Gly Thr Thr Val Thr Val Ser Ser
        130                 135
```

<210> SEQ ID NO 26
<211> LENGTH: 119
<212> TYPE: PRT
<213> ORGANISM: Artificial Sequence
<220> FEATURE:
<223> OTHER INFORMATION: VH Amino Acid Sequence

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Asn Arg Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Pro Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Ser Arg Val Thr Leu Gly Leu Glu Phe Asp Phe Trp Gly Gln Gly
            100                 105                 110

Thr Leu Val Thr Val Ser Ser
        115
```

<210> SEQ ID NO 27
<211> LENGTH: 120
<212> TYPE: PRT
<213> ORGANISM: Artificial Sequence
<220> FEATURE:
<223> OTHER INFORMATION: VH Amino Acid Sequence

<400> SEQUENCE: 27

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30
```

```
Gly Met Cys Val Gly Trp Ile Arg Gln Pro Pro Gly Lys Ala Leu Glu
            35                  40                  45

Trp Leu Ala Leu Ile Glu Trp Asp Asp Lys Tyr Tyr Asn Thr Ser
 50                  55                  60

Leu Lys Thr Arg Leu Ser Ile Ser Lys Asp Thr Ser Lys Asn Gln Val
 65                  70                  75                  80

Val Leu Thr Met Thr Asn Met Asp Pro Val Asp Thr Gly Thr Tyr Tyr
                 85                  90                  95

Cys Ala Arg His Ser Ser Ser Arg Gly Phe Asp Tyr Trp Gly Gln
                100                 105                 110

Gly Ala Leu Val Thr Val Ser Ser
            115                 120

<210> SEQ ID NO 28
<211> LENGTH: 121
<212> TYPE: PRT
<213> ORGANISM: Artificial Sequence
<220> FEATURE:
<223> OTHER INFORMATION: VH Amino Acid Sequence

<400> SEQUENCE: 28

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Thr Tyr
                 20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Thr Ala Thr Ala Tyr
 65                  70                  75                  80

Leu Gln Trp Ser Ser Leu Asn Ala Ser Asp Ser Ala Met Tyr Tyr Cys
                 85                  90                  95

Ala Arg Gln Gly Gly Ser His Gly Tyr Asp Ala Phe His Met Trp Gly
                100                 105                 110

Gln Gly Thr Met Val Thr Val Ser Ser
            115                 120

<210> SEQ ID NO 29
<211> LENGTH: 112
<212> TYPE: PRT
<213> ORGANISM: Artificial Sequence
<220> FEATURE:
<223> OTHER INFORMATION: VH Amino Acid Sequence

<400> SEQUENCE: 29

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Ser Thr Tyr
                 20                  25                  30

Ala Leu Asn Trp Val Arg Gln Ala Pro Gly Lys Gly Leu Glu Trp Val
            35                  40                  45

Ala Gly Ile Asn Gly Thr Gly Tyr Asn Thr Tyr Tyr Ala Asp Ser Val
 50                  55                  60

Arg Gly Arg Phe Thr Ile Ser Arg Asp Asn Ser Lys Asn Thr Val Thr
 65                  70                  75                  80
```

```
Leu Glu Met Asn Ser Leu Arg Val Glu Asp Thr Ala Thr Tyr Tyr Cys
                85                  90                  95

His Lys Val Pro Trp Trp Gly Gln Gly Thr Leu Val Thr Val Ser Ser
            100                 105                 110
```

<210> SEQ ID NO 30
<211> LENGTH: 128
<212> TYPE: PRT
<213> ORGANISM: Artificial Sequence
<220> FEATURE:
<223> OTHER INFORMATION: VH Amino Acid Sequence

<400> SEQUENCE: 30

```
Gln Val Gln Leu Gln Glu Ser Gly Pro Arg Leu Val Lys Pro Ser Glu
1               5                   10                  15

Thr Leu Ser Leu Thr Cys Phe Val Ser Gly Gly Ser Ile Asn Asn Ser
            20                  25                  30

Tyr Trp Thr Trp Ile Arg Gln Pro Pro Gly Gln Gly Leu Glu Trp Ile
        35                  40                  45

Gly Phe Val Phe Ser Ser Gly Arg Thr Asn Tyr Ser Pro Ser Leu Lys
    50                  55                  60

Ser Arg Val Thr Ile Ser Val Asp Thr Ser Lys Asn Leu Phe Ser Leu
65                  70                  75                  80

Arg Leu Thr Ser Val Thr Ala Ala Asp Thr Ala Val Tyr Phe Cys Ala
                85                  90                  95

Arg Gln Val His Tyr Asp Phe Trp Ser Gly Tyr Ser Leu Thr Lys Thr
            100                 105                 110

Asn Trp Phe Asp Pro Trp Gly Gln Gly Thr Leu Val Thr Val Ser Ser
            115                 120                 125
```

<210> SEQ ID NO 31
<211> LENGTH: 128
<212> TYPE: PRT
<213> ORGANISM: Artificial Sequence
<220> FEATURE:
<223> OTHER INFORMATION: VH Amino Acid Sequence

<400> SEQUENCE: 31

```
Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Asn Asn Ser
            20                  25                  30

Tyr Trp Thr Trp Ile Arg Gln Pro Pro Gly Gln Gly Leu Glu Trp Ile
        35                  40                  45

Gly Phe Val Tyr Ser Ser Gly Arg Thr Tyr Tyr Ser Pro Ser Leu Lys
    50                  55                  60

Ser Arg Val Thr Ile Ser Val Asp Thr Ser Lys Asn Phe Phe Ser Leu
65                  70                  75                  80

Arg Leu Asn Ser Val Thr Ala Ala Asp Thr Ala Val Tyr Phe Cys Ala
                85                  90                  95

Arg Gln Val His Tyr Asp Leu Trp Ser Gly Tyr Ser Leu Thr Lys Thr
            100                 105                 110

Asn Trp Phe Asp Pro Trp Gly Gln Gly Thr Leu Val Thr Val Ser Ser
            115                 120                 125
```

<210> SEQ ID NO 32
<211> LENGTH: 121
<212> TYPE: PRT
<213> ORGANISM: Artificial Sequence

```
<220> FEATURE:
<223> OTHER INFORMATION: VH Amino Acid Sequence

<400> SEQUENCE: 32

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
                85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser
        115                 120

<210> SEQ ID NO 33
<211> LENGTH: 106
<212> TYPE: PRT
<213> ORGANISM: Artificial Sequence
<220> FEATURE:
<223> OTHER INFORMATION: VL Amino Acid Sequence

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45
```

Tyr Ala Ser Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Glu Ser Tyr Ser Thr Pro Pro
                 85                  90                  95

Thr Phe Gly Gln Gly Thr Lys Val Glu Ile Lys
                100                 105

<210> SEQ ID NO 35
<211> LENGTH: 106
<212> TYPE: PRT
<213> ORGANISM: Artificial Sequence
<220> FEATURE:
<223> OTHER INFORMATION: VL Amino Acid Sequence

<400> SEQUENCE: 35

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Val Pro Lys Lys Tyr Ala
                 20                  25                  30

Tyr Trp Tyr Gln Gln Lys Ser Gly Gln Ala Pro Val Leu Val Ile Tyr
             35                  40                  45

Glu Asp Lys Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Glu Gly Val
                 85                  90                  95

Phe Gly Gly Gly Thr Lys Leu Thr Val Leu
                100                 105

<210> SEQ ID NO 36
<211> LENGTH: 106
<212> TYPE: PRT
<213> ORGANISM: Artificial Sequence
<220> FEATURE:
<223> OTHER INFORMATION: VL Amino Acid Sequence

<400> SEQUENCE: 36

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
                 20                  25                  30

Tyr Trp Tyr Gln Gln Lys Ser Gly Gln Ala Pro Val Leu Val Ile His
             35                  40                  45

Glu Asp Thr Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr His Cys Tyr Ser Thr Asp Ser Ser Gly Val Val
                 85                  90                  95

Phe Gly Gly Gly Thr Lys Leu Thr Val Leu
                100                 105

<210> SEQ ID NO 37
<211> LENGTH: 113
<212> TYPE: PRT
<213> ORGANISM: Artificial Sequence

```
<220> FEATURE:
<223> OTHER INFORMATION: VL Amino Acid Sequence

<400> SEQUENCE: 37

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Gly Val Leu Ser Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Asn Leu Arg Thr Phe Gly Gln Gly Thr Lys Val Glu Ile
            100                 105                 110

Arg

<210> SEQ ID NO 38
<211> LENGTH: 106
<212> TYPE: PRT
<213> ORGANISM: Artificial Sequence
<220> FEATURE:
<223> OTHER INFORMATION: VL Amino Acid Sequence

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Arg Ile Ser Asn Trp
            20                  25                  30

Leu Ala Trp Tyr Gln Lys Lys Pro Gly Lys Ala Pro Lys Leu Leu Ile
        35                  40                  45

Tyr Lys Ala Ser Thr Leu Glu Ser Glu Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Leu Ala Thr Tyr Tyr Cys His Gln Tyr Ile Ser Tyr Tyr Thr
                85                  90                  95

Phe Gly Gln Gly Thr Lys Leu Glu Ile Lys
            100                 105

<210> SEQ ID NO 39
<211> LENGTH: 111
<212> TYPE: PRT
<213> ORGANISM: Artificial Sequence
<220> FEATURE:
<223> OTHER INFORMATION: VL Amino Acid Sequence

<400> SEQUENCE: 39

Gln Ser Val Leu Thr Gln Pro Pro Ser Val Ser Ala Ala Pro Gly Glu
1               5                   10                  15

Lys Val Thr Ile Ser Cys Ser Gly Ser Ser Asn Ile Gly Ala Asn
            20                  25                  30

Ser Val Ser Trp Tyr Gln Gln Phe Pro Gly Thr Ala Pro Lys Leu Leu
        35                  40                  45
```

```
Ile Tyr Asp Asn Asp Lys Arg Pro Ser Gly Val Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Val Gly Ile Leu
                 85                  90                  95

Ser Ala Gly Trp Val Phe Gly Gly Thr Lys Leu Thr Val Leu
            100                 105                 110

<210> SEQ ID NO 40
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 40

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Asp Arg Phe Ser Gly
 50                  55                  60

Ser Gly Ser Gly Thr Asp Phe Thr Leu Thr Ile Ser Ser Leu Lys Pro
 65                  70                  75                  80

Glu Asp Phe Ala Val Tyr Tyr Cys Gln Leu Arg Ser Asn Trp Ala Tyr
                 85                  90                  95

Thr Phe Gly Gln Gly Thr Lys Leu Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 41

Ser Tyr Gly Leu Thr Gln Pro Pro Ser Val Ser Val Ser Pro Gly Gln
 1               5                  10                  15

Thr Ala Arg Ile Thr Cys Ser Gly Asp Ala Leu Ala Lys Gln Tyr Val
                20                  25                  30

Tyr Trp Tyr Gln Gln Lys Pro Gly Gln Ala Pro Val Leu Val Ile Asp
             35                  40                  45

Lys Asp Arg Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Arg Thr Tyr
                 85                  90                  95

Val Phe Gly Thr Gly Thr Lys Val Thr Val Leu
            100                 105

<210> SEQ ID NO 42
<211> LENGTH: 112
<212> TYPE: PRT
<213> ORGANISM: Artificial Sequence
```

```
<220> FEATURE:
<223> OTHER INFORMATION: VL Amino Acid Sequence

<400> SEQUENCE: 42

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Leu Thr Trp Thr Phe Gly Gln Gly Thr Lys Val Glu Ile Lys
            100                 105                 110

<210> SEQ ID NO 43
<211> LENGTH: 113
<212> TYPE: PRT
<213> ORGANISM: Artificial Sequence
<220> FEATURE:
<223> OTHER INFORMATION: VL Amino Acid Sequence

<400> SEQUENCE: 43

Asp Ile Val Leu Thr Gln Ser Pro Glu Ser Leu Ala Val Ser Leu Gly
1               5                   10                  15

Glu Arg Ala Thr Ile Ser Cys Lys Ser Ser Gln Ser Leu Phe Phe Lys
            20                  25                  30

Ser Asn Asn Lys Asn Tyr Leu Ala Trp Tyr Gln Gln Lys Pro Gly Gln
        35                  40                  45

Pro Pro Lys Val Ile Ile Tyr Trp Ala Ser Thr Arg Glu Ser Gly Val
    50                  55                  60

Pro Ala Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys His Gln
                85                  90                  95

Tyr Tyr Ser Thr Gln Tyr Ser Phe Gly Gln Gly Thr Lys Leu Glu Ile
            100                 105                 110

Lys

<210> SEQ ID NO 44
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 44

Asp Ile Gln Met Thr Gln Ser Pro Ser Ser Leu Ser Ala Ser Val Gly
1               5                   10                  15

Asp Thr Val Thr Ile Thr Cys Arg Ser Gln Ser Ile Ser Asn Phe
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Val Asn Gly
        50                  55                  60

Ser Thr Ser Gly Thr Glu Phe Thr Leu Thr Leu Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
                100                 105

<210> SEQ ID NO 45
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 45

Asp Ile Gln Met Thr Gln Ser Pro Ser Ser Leu Ser Ala Ser Val Gly
1               5                   10                  15

Asp Thr Val Thr Ile Thr Cys Arg Thr Ser Gln Ser Ile Ser Asn Phe
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Asn Gly
        50                  55                  60

Ser Thr Ser Gly Thr Asp Phe Thr Leu Thr Leu Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
                100                 105

<210> SEQ ID NO 46
<211> LENGTH: 110
<212> TYPE: PRT
<213> ORGANISM: Artificial Sequence
<220> FEATURE:
<223> OTHER INFORMATION: VL Amino Acid Sequence

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Ser Gly Ser Ser Tyr Asn Ile Gly Ser Asn
                20                  25                  30

Tyr Val Tyr Trp Tyr Gln Gln Phe Pro Gly Thr Ala Pro Lys Leu Leu
            35                  40                  45

Ile Ser Arg Ser Ile Gln Arg Pro Ser Gly Val Pro Asp Arg Phe Ser
        50                  55                  60

Gly Ser Lys Ser Val Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Arg Ala Trp Val Phe Gly Gly Gly Thr Lys Leu Thr Val Leu
                100                 105                 110

<210> SEQ ID NO 47
<211> LENGTH: 452
<212> TYPE: PRT
<213> ORGANISM: Artificial Sequence
<220> FEATURE:
<223> OTHER INFORMATION: Full-Length Heavy Chain Amino Acid Sequence

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

-continued

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 48
<211> LENGTH: 452
<212> TYPE: PRT
<213> ORGANISM: Artificial Sequence
<220> FEATURE:
<223> OTHER INFORMATION: Full-Length Heavy Chain Amino Acid Sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 49
<211> LENGTH: 454
<212> TYPE: PRT
<213> ORGANISM: Artificial Sequence
<220> FEATURE:
<223> OTHER INFORMATION: Full-Length Heavy Chain Amino Acid Sequence

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Asn Ser
            20                  25                  30

Tyr Trp Ser Trp Ile Arg Gln Pro Pro Gly Lys Gly Leu Glu Trp Ile
        35                  40                  45

Gly Tyr Leu Tyr Ser Ser Gly Arg Thr Asn Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr His Leu Gly Gly Phe His Tyr Gly Gly Gly Phe Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Cys Ser Tyr His Leu Cys Gln Lys Ser Leu
            435                 440                 445

Ser Leu Ser Pro Gly Lys
            450

<210> SEQ ID NO 50
<211> LENGTH: 451
<212> TYPE: PRT
<213> ORGANISM: Artificial Sequence
<220> FEATURE:
<223> OTHER INFORMATION: Full-Length Heavy Chain Amino Acid Sequence

<400> SEQUENCE: 50

Gln Leu Gln Leu Val Glu Ser Gly Gly Gly Ala Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
            35                  40                  45

Ala Val Thr Ser Phe Asp Gly Ser Asn Glu Tyr Tyr Ile Asp Ser Val
50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
            85                  90                  95

Ala Arg Asp Glu Tyr Thr Gly Gly Trp Tyr Ser Val Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 51
<211> LENGTH: 451
<212> TYPE: PRT
<213> ORGANISM: Artificial Sequence
<220> FEATURE:
<223> OTHER INFORMATION: Full-Length Heavy Chain Amino Acid Sequence

<400> SEQUENCE: 51

```
Gln Leu Gln Leu Val Glu Ser Gly Gly Gly Val Gln Pro Gly Arg
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Thr Ser Phe Asp Gly Ser Asn Glu Tyr Tyr Ile Asp Ser Val
    50                  55                  60

Lys Gly Arg Phe Thr Ile Ser Arg Asp Asn Thr Lys Asn Thr Leu Tyr
65                  70                  75                  80

Leu Gln Met Thr Gly Leu Arg Val Glu Asp Thr Ala Leu Tyr Phe Cys
            85                  90                  95

Ala Arg Asp Glu Tyr Thr Gly Gly Trp Tyr Ser Val Gly Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 52
<211> LENGTH: 212
<212> TYPE: PRT
<213> ORGANISM: Artificial Sequence
<220> FEATURE:
<223> OTHER INFORMATION: Full-Length Light Chain Amino Acid Sequence

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 53
<211> LENGTH: 214
<212> TYPE: PRT
<213> ORGANISM: Artificial Sequence
<220> FEATURE:
<223> OTHER INFORMATION: Full-Length Light Chain Amino Acid Sequence

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45
```

```
Tyr Ala Ser Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Glu Ser Tyr Ser Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 54
<211> LENGTH: 216
<212> TYPE: PRT
<213> ORGANISM: Artificial Sequence
<220> FEATURE:
<223> OTHER INFORMATION: Full-Length Light Chain Amino Acid Sequence

<400> SEQUENCE: 54

Gln Ser Val Leu Thr Gln Pro Pro Ser Ala Ser Gly Thr Pro Gly Gln
1               5                   10                  15

Arg Val Thr Ile Ser Cys Ser Gly Ser Ser Tyr Asn Ile Gly Ser Asn
             20                  25                  30

Tyr Val Tyr Trp Tyr Gln Gln Phe Pro Gly Thr Ala Pro Lys Leu Leu
         35                  40                  45

Ile Ser Arg Ser Ile Gln Arg Pro Ser Gly Val Pro Asp Arg Phe Ser
 50                  55                  60

Gly Ser Lys Ser Val Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Arg Ala Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 55
<211> LENGTH: 6
<212> TYPE: PRT
<213> ORGANISM: Artificial Sequence
<220> FEATURE:
<223> OTHER INFORMATION: Fc region

<400> SEQUENCE: 55

Cys Ser Tyr His Leu Cys
1               5

<210> SEQ ID NO 56
<211> LENGTH: 17
<212> TYPE: PRT
<213> ORGANISM: Artificial Sequence
<220> FEATURE:
<223> OTHER INFORMATION: heavy chain constant domain

<400> SEQUENCE: 56

Met His Glu Ala Cys Ser Tyr His Leu Cys Gln Lys Ser Leu Ser Leu
1               5                   10                  15

Ser

<210> SEQ ID NO 57
<211> LENGTH: 293
<212> TYPE: PRT
<213> ORGANISM: Artificial Sequence
<220> FEATURE:
<223> OTHER INFORMATION: S. aureus alpha toxin

<400> SEQUENCE: 57

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190
```

```
Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 58
<211> LENGTH: 293
<212> TYPE: PRT
<213> ORGANISM: Artificial Sequence
<220> FEATURE:
<223> OTHER INFORMATION: S. aureus alpha toxin H35L mutant

<400> SEQUENCE: 58

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

```
Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 59
<211> LENGTH: 300
<212> TYPE: PRT
<213> ORGANISM: Artificial Sequence
<220> FEATURE:
<223> OTHER INFORMATION: S. aureus HlgB

<400> SEQUENCE: 59

```
Gly Glu Gly Lys Ile Thr Pro Val Ser Val Lys Val Asp Asp Lys
1               5                   10                  15

Val Thr Leu Tyr Lys Thr Thr Ala Thr Ala Asp Ser Asp Lys Phe Lys
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Thr Gly Asn Ile Asn Ser Gly Phe
    50                  55                  60

Val Lys Pro Asn Pro Asn Asp Tyr Asp Phe Ser Lys Leu Tyr Trp Gly
65                  70                  75                  80

Ala Lys Tyr Asn Val Ser Ile Ser Ser Gln Ser Asn Asp Ser Val Asn
                85                  90                  95

Val Val Asp Tyr Ala Pro Lys Asn Gln Asn Glu Glu Phe Gln Val Gln
            100                 105                 110

Asn Thr Leu Gly Tyr Thr Phe Gly Gly Asp Ile Ser Ile Ser Asn Gly
        115                 120                 125

Leu Ser Gly Gly Leu Asn Gly Asn Thr Ala Phe Ser Glu Thr Ile Asn
    130                 135                 140

Tyr Lys Gln Glu Ser Tyr Arg Thr Thr Leu Ser Arg Asn Thr Asn Tyr
145                 150                 155                 160

Lys Asn Val Gly Trp Gly Val Glu Ala His Lys Ile Met Asn Asn Gly
                165                 170                 175

Trp Gly Pro Tyr Gly Arg Asp Ser Phe His Pro Thr Tyr Gly Asn Glu
            180                 185                 190

Leu Phe Leu Ala Gly Arg Gln Ser Ser Ala Tyr Ala Gly Gln Asn Phe
        195                 200                 205

Ile Ala Gln His Gln Met Pro Leu Leu Ser Arg Ser Asn Phe Asn Pro
    210                 215                 220

Glu Phe Leu Ser Val Leu Ser His Arg Gln Asp Gly Ala Lys Lys Ser
225                 230                 235                 240

Lys Ile Thr Val Thr Tyr Gln Arg Glu Met Asp Leu Tyr Gln Ile Arg
                245                 250                 255

Trp Asn Gly Phe Tyr Trp Ala Gly Ala Asn Tyr Lys Asn Phe Lys Thr
            260                 265                 270

Arg Thr Phe Lys Ser Thr Tyr Glu Ile Asp Trp Glu Asn His Lys Val
        275                 280                 285

Lys Leu Leu Asp Thr Lys Glu Thr Glu Asn Asn Lys
    290                 295                 300
```

<210> SEQ ID NO 60
<211> LENGTH: 302
<212> TYPE: PRT
<213> ORGANISM: Artificial Sequence
<220> FEATURE:
<223> OTHER INFORMATION: S. aureus LukF

<400> SEQUENCE: 60

```
Gly Ala Gln His Ile Thr Pro Val Ser Glu Lys Val Asp Asp Lys
1               5                   10                  15

Ile Thr Leu Tyr Lys Thr Thr Ala Thr Ser Asp Ser Asp Lys Leu Lys
                20                  25                  30

Ile Ser Gln Ile Leu Thr Phe Asn Phe Ile Lys Asp Lys Ser Tyr Asp
            35                  40                  45

Lys Asp Thr Leu Ile Leu Lys Ala Ala Gly Asn Ile Tyr Ser Gly Tyr
        50                  55                  60

Thr Lys Pro Asn Pro Lys Asp Thr Ile Ser Ser Gln Phe Tyr Trp Gly
65                  70                  75                  80

Ser Lys Tyr Asn Ile Ser Ile Asn Ser Asp Ser Asn Asp Ser Val Asn
                85                  90                  95

Val Val Asp Tyr Ala Pro Lys Asn Gln Asn Glu Glu Phe Gln Val Gln
                100                 105                 110

Gln Thr Val Gly Tyr Ser Tyr Gly Gly Asp Ile Asn Ile Ser Asn Gly
            115                 120                 125

Leu Ser Gly Gly Gly Asn Gly Ser Lys Ser Phe Ser Glu Thr Ile Asn
130                 135                 140

Tyr Lys Gln Glu Ser Tyr Arg Thr Ser Leu Asp Lys Arg Thr Asn Phe
145                 150                 155                 160

Lys Lys Ile Gly Trp Asp Val Glu Ala His Lys Ile Met Asn Asn Gly
                165                 170                 175

Trp Gly Pro Tyr Gly Arg Asp Ser Tyr His Ser Thr Tyr Gly Asn Glu
            180                 185                 190

Met Phe Leu Gly Ser Arg Gln Ser Asn Leu Asn Ala Gly Gln Asn Phe
        195                 200                 205

Leu Glu Tyr His Lys Met Pro Val Leu Ser Arg Gly Asn Phe Asn Pro
210                 215                 220

Glu Phe Ile Gly Val Leu Ser Arg Lys Gln Asn Ala Ala Lys Lys Ser
225                 230                 235                 240

Lys Ile Thr Val Thr Tyr Gln Arg Glu Met Asp Arg Tyr Thr Asn Phe
                245                 250                 255

Trp Asn Gln Leu His Trp Ile Gly Asn Asn Tyr Lys Asp Glu Asn Arg
            260                 265                 270

Ala Thr His Thr Ser Ile Tyr Glu Val Asp Trp Glu Asn His Thr Val
        275                 280                 285

Lys Leu Ile Asp Thr Gln Ser Lys Glu Lys Asn Pro Met Ser
290                 295                 300
```

<210> SEQ ID NO 61
<211> LENGTH: 302
<212> TYPE: PRT
<213> ORGANISM: Artificial Sequence
<220> FEATURE:
<223> OTHER INFORMATION: S. aureus LukD

<400> SEQUENCE: 61

Gly Ala Gln His Ile Thr Pro Val Ser Glu Lys Lys Val Asp Asp Lys
1               5                   10                  15

Ile Thr Leu Tyr Lys Thr Thr Ala Thr Ser Asp Asn Asp Lys Leu Asn
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Ala Gly Asn Ile Asn Ser Gly Tyr
    50                  55                  60

Lys Lys Pro Asn Pro Lys Asp Tyr Asn Tyr Ser Gln Phe Tyr Trp Gly
65                  70                  75                  80

Gly Lys Tyr Asn Val Ser Val Ser Ser Glu Ser Asn Asp Ala Val Asn
                85                  90                  95

Val Val Asp Tyr Ala Pro Lys Asn Gln Asn Glu Glu Phe Gln Val Gln
                100                 105                 110

Gln Thr Leu Gly Tyr Ser Tyr Gly Gly Asp Ile Asn Ile Ser Asn Gly
            115                 120                 125

Leu Ser Gly Gly Leu Asn Gly Ser Lys Ser Phe Ser Glu Thr Ile Asn
130                 135                 140

Tyr Lys Gln Glu Ser Tyr Arg Thr Thr Ile Asp Arg Lys Thr Asn His
145                 150                 155                 160

Lys Ser Ile Gly Trp Gly Val Glu Ala His Lys Ile Met Asn Asn Gly
                165                 170                 175

Trp Gly Pro Tyr Gly Arg Asp Ser Tyr Asp Pro Thr Tyr Gly Asn Glu
            180                 185                 190

Leu Phe Leu Gly Gly Arg Gln Ser Ser Ser Asn Ala Gly Gln Asn Phe
        195                 200                 205

Leu Pro Thr His Gln Met Pro Leu Leu Ala Arg Gly Asn Phe Asn Pro
    210                 215                 220

Glu Phe Ile Ser Val Leu Ser His Lys Gln Asn Asp Thr Lys Lys Ser
225                 230                 235                 240

Lys Ile Lys Val Thr Tyr Gln Arg Glu Met Asp Arg Tyr Thr Asn Gln
                245                 250                 255

Trp Asn Arg Leu His Trp Val Gly Asn Asn Tyr Lys Asn Gln Asn Thr
            260                 265                 270

Val Thr Phe Thr Ser Thr Tyr Glu Val Asp Trp Gln Asn His Thr Val
        275                 280                 285

Lys Leu Ile Gly Thr Asp Ser Lys Glu Thr Asn Pro Gly Val
    290                 295                 300

<210> SEQ ID NO 62
<211> LENGTH: 5
<212> TYPE: PRT
<213> ORGANISM: Artificial Sequence
<220> FEATURE:
<223> OTHER INFORMATION: VH CDR1

<400> SEQUENCE: 62

Ser Phe Ala Met Ser
1               5

<210> SEQ ID NO 63
<211> LENGTH: 17
<212> TYPE: PRT
<213> ORGANISM: Artificial Sequence
<220> FEATURE:
<223> OTHER INFORMATION: VH CDR2

```
<400> SEQUENCE: 63

Ala Ile Ser Gly Ser Gly Gly Asn Thr Tyr Tyr Ala Asp Ser Val Lys
1               5                   10                  15

Gly

<210> SEQ ID NO 64
<211> LENGTH: 5
<212> TYPE: PRT
<213> ORGANISM: Artificial Sequence
<220> FEATURE:
<223> OTHER INFORMATION: VH CDR3

<400> SEQUENCE: 64

Ile Ala Phe Asp Ile
1               5

<210> SEQ ID NO 65
<211> LENGTH: 11
<212> TYPE: PRT
<213> ORGANISM: Artificial Sequence
<220> FEATURE:
<223> OTHER INFORMATION: VL CDR1

<400> SEQUENCE: 65

Arg Ala Ser Gln Gly Ile Arg Asn Asp Leu Gly
1               5                   10

<210> SEQ ID NO 66
<211> LENGTH: 7
<212> TYPE: PRT
<213> ORGANISM: Artificial Sequence
<220> FEATURE:
<223> OTHER INFORMATION: VL CDR2

<400> SEQUENCE: 66

Val Ala Ser Ser Leu Gln Ser
1               5

<210> SEQ ID NO 67
<211> LENGTH: 9
<212> TYPE: PRT
<213> ORGANISM: Artificial Sequence
<220> FEATURE:
<223> OTHER INFORMATION: VL CDR3

<400> SEQUENCE: 67

Leu Gln His Asn Ser Tyr Pro Phe Thr
1               5

<210> SEQ ID NO 68
<211> LENGTH: 114
<212> TYPE: PRT
<213> ORGANISM: Artificial Sequence
<220> FEATURE:
<223> OTHER INFORMATION: VH Amino Acid Sequence

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ala Met Ser Trp Val Arg Gln Ala Pro Gly Lys Gly Leu Glu Trp Val
            35                  40                  45
```

```
Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ala Phe Asp Ile Trp Gly Gln Gly Thr Met Val Thr Val
            100                 105                 110

Ser Ser

<210> SEQ ID NO 69
<211> LENGTH: 107
<212> TYPE: PRT
<213> ORGANISM: Artificial Sequence
<220> FEATURE:
<223> OTHER INFORMATION: VL Amino Acid Sequence

<400> SEQUENCE: 69

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Val Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Lys Val Asp Ile Lys
            100                 105

<210> SEQ ID NO 70
<211> LENGTH: 454
<212> TYPE: PRT
<213> ORGANISM: Artificial Sequence
<220> FEATURE:
<223> OTHER INFORMATION: Full-length light chain amino acid sequecne

<400> SEQUENCE: 70

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Gln Asn Ser
             20                  25                  30

Tyr Trp Ser Trp Ile Arg Gln Pro Pro Gly Lys Gly Leu Glu Trp Ile
         35                  40                  45

Gly Tyr Leu Tyr Ser Ser Gly Arg Thr Asn Tyr Thr Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Thr His Leu Gly Gly Phe His Tyr Gly Gly Gly Phe Trp Phe Asp
            100                 105                 110

Pro Trp Gly Gln Gly Thr Leu Val Thr Val Ser Ser Ala Ser Thr Lys
        115                 120                 125
```

-continued

```
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Lys
    450
```

COMBINATIONS OF ANTI-*STAPHYLOCOCCUS AUREUS* ANTIBODIES

CROSS REFERENCE TO RELATED APPLICATIONS

This application claims the priority benefit of U.S. Provisional Application No. 62/833,297, filed Apr. 12, 2019, and U.S. Provisional Application No. 62/743,490, filed Oct. 9, 2018, each of which is hereby incorporated by reference herein in its entirety.

SEQUENCE LISTING

The content of the electronically submitted sequence listing (Name: 2943_1020002_SeqListing_ST25.txt; Size: 81,662 bytes; and Date of Creation: Oct. 8, 2019) is hereby incorporated by reference.

BACKGROUND

Infections caused by antimicrobial resistant (AMR) bacterial pathogens are an increasing threat to public health. The ongoing AMR epidemic has been fueled, in part, by empiric broad spectrum antibiotic therapy. This has led to the exploration of pathogen specific methods, including monoclonal antibodies (mAbs), to prevent or treat serious bacterial infections. Numerous monoclonal antibodies are currently in development for the prevention or treatment of antibiotic resistant bacterial infections (see, e.g., DiGiandomenico, A., and B. R. Sellman, *Curr. Opin. Microbiol.*, 27: 78-85 (2015)). Such passive immunization strategies provide an immediate and potent immunoglobulin response against the target pathogen. Ideally, the monoclonal antibody or monoclonal antibody cocktail provides multiple mechanisms of action to neutralize key bacterial virulence mechanisms and augment the host innate immune response, thus providing the greatest opportunity for clinical success.

*Staphylococcus aureus* is a bacterial pathogen that causes a wide array of diseases including skin and soft tissue infections, endocarditis, osteomyelitis, pneumonia, and bacteremia (Lowy, F. D., *N. Engl. J. Med.*, 339(8): 520-32 (1998)). Preclinical studies indicate monoclonal antibody-based approaches hold promise for prophylaxis and adjunctive therapy against *S. aureus* infections (see, e.g., Hazenbos et al., *PLoS Pathog.*, 9(10):e1003653. doi: 10.1371/journal.ppat.10036532013 (2013); Rouha, H., *MAbs*, 7(1): 243-254 (2015); Foletti et al., *J. Mol. Biol.*, 425(10): 1641-1654 (2013); Karauzum et al., *J Biol Chem.*, 287(30): 25203-15 (2012); and Hua et al., *Antimicrob Agents Chemother.*, 58(2): 1108-17 (2014)). However, treatment with individual antibodies may not be sufficient to address all *Staphylococcus aureus* infections. Thus, there remains a need for compositions and methods for treating *Staphylococcus aureus* infections, particularly infections that are resistant to currently-available antibiotics and that provide broad disease and strain coverage. The present disclosure provides such compositions and methods.

BRIEF SUMMARY OF THE INVENTION

As demonstrated herein, combinations of antibodies that target several different bacterial virulence factors via complementary mechanism of action can provide broad strain coverage and broad disease coverage. Exemplary animal models supporting the breadth of strain and disease coverage encompassed by the combinations of antibodies provided herein is provided in FIG. 1.

Provided herein are methods of treating or preventing a *Staphylococcus aureus* (*S. aureus*) infection in a subject comprising administering to the subject (a) an antibody or antigen-binding fragment thereof that binds to *S. aureus* alpha toxin (AT), (b) an antibody or antigen-binding fragment thereof that binds to *S. aureus* clumping factor A (ClfA), and (c) an antibody or antigen-binding fragment thereof that binds to at least one *S. aureus* leukotoxin.

Provided herein are also methods of treating or preventing a *S. aureus* infection in a subject comprising administering to the subject an antibody or antigen-binding fragment thereof that binds to at least one *S. aureus* leukotoxin and (a) an antibody or antigen-binding fragment thereof that binds to *S. aureus* alpha toxin (AT) or (b) an antibody or antigen-binding fragment thereof that binds to *S. aureus* clumping factor A (ClfA).

Provided herein are also compositions comprising (a) an antibody or antigen-binding fragment thereof that binds to *S. aureus* AT, (b) an antibody or antigen-binding fragment thereof that binds to *S. aureus* ClfA, and (c) an antibody or antigen-binding fragment thereof that binds to at least one *S. aureus* leukotoxin.

Provided herein are also compositions comprising an antibody or antigen-binding fragment thereof that binds to at least one *S. aureus* leukotoxin and (a) an antibody or antigen-binding fragment thereof that binds to *S. aureus* AT or (b) an antibody or antigen-binding fragment thereof that binds to *S. aureus* ClfA.

In certain instances, the composition is for use in treating or preventing a *S. aureus* infection in a subject.

Provided herein are also antibodies and antigen-binding fragments thereof that bind to *S. aureus* AT for use in treating or preventing a *S. aureus* infection in a subject in combination with an antibody or antigen-binding fragment thereof that binds to *S. aureus* ClfA and an antibody or antigen-binding fragment thereof that binds to at least one *S. aureus* leukotoxin.

Provided herein are also antibodies and antigen-binding fragments thereof that bind to *S. aureus* ClfA for use in treating or preventing a *S. aureus* infection in a subject in combination with an antibody or antigen-binding fragment thereof that binds to *S. aureus* AT and an antibody or antigen-binding fragment thereof that binds to at least one *S. aureus* leukotoxin.

Provided herein are also antibodies and antigen-binding fragments thereof that bind to at least one *S. aureus* leukotoxin for use in treating or preventing a *S. aureus* infection in a subject in combination with an antibody or antigen-binding fragment thereof that binds to *S. aureus* AT and/or an antibody or antigen-binding fragment thereof that binds to *S. aureus* ClfA.

In certain instances, the composition is used in the preparation of a medicament for treating or preventing a *S. aureus* infection in a subject.

Provided herein are also uses of an antibody or antigen-binding fragment thereof that binds to *S. aureus* AT in the preparation of a medicament for treating or preventing a *S. aureus* infection in a subject in combination with an antibody or antigen-binding fragment thereof that binds to *S. aureus* ClfA and an antibody or antigen-binding fragment thereof that binds to at least one *S. aureus* leukotoxin.

Provided herein are also uses of an antibody or antigen-binding fragment thereof that binds to *S. aureus* ClfA in the preparation of a medicament for treating or preventing a *S. aureus* infection in a subject in combination with an antibody or antigen-binding fragment thereof that binds to *S. aureus* AT and an antibody or antigen-binding fragment thereof that binds to at least one *S. aureus* leukotoxin.

Provided herein are also uses of an antibody or antigen-binding fragment thereof that binds to at least one *S. aureus* leukotoxin in the preparation of a medicament for treating or preventing a *S. aureus* infection in a subject in combination with an antibody or antigen-binding fragment thereof that binds to *S. aureus* AT and/or an antibody or antigen-binding fragment thereof that binds to *S. aureus* ClfA.

In certain instances of the method, composition, antibody or antigen-binding fragment thereof, or use provided herein, the antibody or antigen-binding fragment thereof that binds to *S. aureus* AT binds to the same *S. aureus* AT epitope as an antibody comprising a VH comprising the amino acid sequence of SEQ ID NO:19 and a VL comprising the amino acid sequence of SEQ ID NO:33. In certain instances, the antibody or antigen-binding fragment thereof that binds to *S. aureus* AT competitively inhibits binding of an antibody comprising a VH comprising the amino acid sequence of SEQ ID NO:19 and a VL comprising the amino acid sequence of SEQ ID NO:33 to *S. aureus* AT. In certain instances, the antibody or antigen-binding fragment thereof that binds to *S. aureus* AT comprises a variable heavy chain (VH) complementarity determining region (CDR) 1 comprising the amino acid sequence of SEQ ID NO:1, a VH CDR2 comprising the amino acid sequence of SEQ ID NO:2, a VH CDR3 comprising the amino acid sequence of SEQ ID NO:3, a variable light chain (VL) CDR1 comprising the amino acid sequence of SEQ ID NO:10, a VL CDR2 comprising the amino acid sequence of SEQ ID NO:11, and a VL CDR3 comprising the amino acid sequence of SEQ ID NO:12. In certain instances, the antibody or antigen-binding fragment thereof that binds to *S. aureus* AT comprises a VH comprising the amino acid sequence of SEQ ID NO:19. In certain instances, the antibody or antigen-binding fragment thereof that binds to *S. aureus* AT comprises a VL comprising the amino acid sequence of SEQ ID NO:33. In certain instances, the antibody or antigen-binding fragment thereof that binds to *S. aureus* AT comprises a heavy chain comprising the amino acid sequence of SEQ ID NO:47. In certain instances, the antibody or antigen-binding fragment thereof that binds to *S. aureus* AT comprises a light chain comprising the amino acid sequence of SEQ ID NO:52. In certain instances, the antibody or antigen-binding fragment thereof that binds to *S. aureus* AT comprises the VH CDR1, VH CDR2, VH CDR3, VL CDR1, VL CDR2, and VL CDR3 of MEDI4893. In certain instances, the CDRs are the Kabat-defined CDRs, the Chothia-defined CDRs, or the AbM-defined CDRs. In certain instances, the antibody or antigen-binding fragment that binds to *S. aureus* AT further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region. In certain instances, the antibody or antigen-binding fragment that binds to *S. aureus* AT further comprises a light chain constant region. In certain instances, the light chain constant region is selected from the group consisting of human immunoglobulin IgGκ and IgGλ light chain constant regions. In certain instances, the light chain constant region is a human IgGκ light chain constant region. In certain instances, the antibody or antigen-binding fragment thereof that binds to *S. aureus* AT is an IgG antibody or antigen-binding fragment thereof. In certain instances, the antibody or antigen-binding fragment thereof that binds to *S. aureus* AT comprises an Fc region that has been engineered to improve half-life. In certain instances, the antibody or antigen-binding fragment thereof that binds to *S. aureus* AT comprises an Fc region with a YTE mutation. In certain instances, the antibody or antigen-binding fragment that binds to *S. aureus* AT is a monoclonal antibody or antigen-binding fragment. In certain instances, the antibody or antigen-binding fragment that binds to *S. aureus* AT is a full-length antibody. In certain instances, the antibody or antigen-binding the antigen-binding fragment comprises a Fab, Fab', $F(ab')_2$, single chain Fv (scFv), disulfide linked Fv, intrabody, IgGΔCH2, minibody, $F(ab')_3$, tetrabody, triabody, diabody, DVD-Ig, Fcab, $mAb^2$, $(scFv)_2$, or scFv-Fc. In certain instances, the antibody or antigen-binding fragment thereof that binds to *S. aureus* AT has an affinity of 80-100 pM for *S. aureus* AT.

In certain instances of the method, composition, antibody or antigen-binding fragment thereof, or use provided herein, the antibody or antigen-binding fragment thereof that binds to *S. aureus* ClfA binds to the same *S. aureus* ClfA epitope as an antibody comprising a VH comprising the amino acid sequence of SEQ ID NO:20 and a VL comprising the amino acid sequence of SEQ ID NO:34. In certain instances, the antibody or antigen-binding fragment thereof that binds to *S. aureus* ClfA competitively inhibits binding of an antibody comprising a VH comprising the amino acid sequence of SEQ ID NO:20 and a VL comprising the amino acid sequence of SEQ ID NO:34 to *S. aureus* ClfA. In certain instances, the antibody or antigen-binding fragment thereof that binds to *S. aureus* ClfA comprises a VH CDR1 comprising the amino acid sequence of SEQ ID NO:4, a VH CDR2 comprising the amino acid sequence of SEQ ID NO:5, a VH CDR3 comprising the amino acid sequence of SEQ ID NO:6, a VL CDR1 comprising the amino acid sequence of SEQ ID NO:13, a VL CDR2 comprising the amino acid sequence of SEQ ID NO:14, and a VL CDR3 comprising the amino acid sequence of SEQ ID NO:15. In certain instances, the antibody or antigen-binding fragment thereof that binds to *S. aureus* ClfA comprises a VH comprising the amino acid sequence of SEQ ID NO:20. In certain instances, the antibody or antigen-binding fragment thereof that binds to *S. aureus* ClfA comprises a VL comprising the amino acid sequence of SEQ ID NO:34. In certain instances, the antibody or antigen-binding fragment thereof that binds to *S. aureus* ClfA comprises a heavy chain constant domain comprising the amino acid sequence of CSYHLC (SEQ ID NO:55). In certain instances, the heavy chain constant domain comprises the amino acid sequence of MHEACSYHLCQKSLSLS (SEQ ID NO:56). In certain instances, the antibody or antigen-binding fragment thereof that binds to *S. aureus* ClfA comprises a heavy chain comprising the amino acid sequence of SEQ ID NO:49. In certain instances, the antibody or antigen-binding fragment thereof that binds to *S. aureus* ClfA comprises a light chain comprising the amino acid sequence of SEQ ID NO:53. In certain instances, the antibody or antigen-binding fragment thereof that binds to *S. aureus* ClfA comprises the VH CDR1, VH CDR2, VH CDR3, VL CDR1, VL CDR2, and VL CDR3 of SAR114-N3Y. In certain instances, the antibody or antigen-binding fragment thereof that binds to *S. aureus* ClfA comprises the VH CDR1, VH CDR2, VH CDR3, VL CDR1, VL CDR2, and VL CDR3 of 11H10, SAR72, SAR80, SAR113, SAR132, SAR352, SAR372, SAR510, SAR547, SAS1, SAS19, or SAS203. In certain instances, the CDRs are the Kabat-defined CDRs, the Chothia-defined CDRs, or the AbM-defined CDRs. In certain instances, the antibody or antigen-binding fragment thereof that binds to *S. aureus* ClfA comprises a VH and a VL, wherein the VH comprises the amino acid sequence set forth in any one of SEQ ID NOs:21-31 and 68. In certain instances, the antibody or antigen-binding fragment thereof that binds to *S. aureus* ClfA comprises a VH and a VL, wherein the VL comprises the amino acid sequence set forth in any one of SEQ ID NOs: 35-45 and 69. In certain instances, the antibody or antigen-binding fragment thereof that binds to *S. aureus* ClfA comprises VH and VL sequences comprising the amino acid sequences set forth in (a) SEQ ID NOs:21 and 35, respectively (b) SEQ ID NOs:22 and 36, respectively, (c) SEQ ID NOs:23 and 37, respectively, (d) SEQ ID NOs:24 and 38, respectively, (e) SEQ ID NOs:25 and 39, respectively, (f) SEQ ID NOs:26 and 40, respectively, (g) SEQ ID NOs:27 and 41, respectively, (h) SEQ ID NOs:28 and 42, respectively (i) SEQ ID NOs:29 and 43, respectively, (j) SEQ ID NOs:30 and 44, respectively, (k) SEQ ID NOs:31 and 45, respectively, or (1) SEQ ID NOs: 68 and 69, respectively. In certain instances, the antibody or antigen-binding fragment that binds to *S. aureus* ClfA further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region. In certain instances, the antibody or antigen-binding fragment that binds to *S. aureus* ClfA further comprises a light chain constant region. In certain instances, the light chain constant region is selected from the group consisting of human immunoglobulin IgGκ and IgGλ light chain constant regions. In certain instances, the light chain constant region is a human IgGκ light chain constant region. In certain instances, the antibody or antigen-binding fragment that binds to *S. aureus* ClfA comprises a mutation that extends half-life relative to the same antibody without the mutation in human FcRn mice. In certain instances, the antibody or antigen-binding fragment that binds to *S. aureus* ClfA comprises a mutation that extends half-life relative to the same antibody without the mutation, and wherein the mutation does not inhibit OPK activity relative to the same antibody or antigen-binding fragment the mutation. In certain instances, the antibody or antigen-binding fragment that binds to *S. aureus* ClfA is a monoclonal antibody or antigen-binding fragment. In certain instances, the antibody or antigen-binding fragment that binds to *S. aureus* ClfA is a full-length antibody. In certain instances, the antibody or antigen-binding fragment that binds to *S. aureus* ClfA is an antigen-binding fragment. In certain instances, the antigen-binding fragment comprises a Fab, Fab', F(ab')$_2$, single chain Fv (scFv), disulfide linked Fv, intrabody, IgGACH2, minibody, F(ab')$_3$, tetrabody, triabody, diabody, DVD-Ig, Fcab, mAb$^2$, (scFv)$_2$, or scFv-Fc. In certain instances, the antibody or antigen-binding fragment thereof that binds to *S. aureus* ClfA has IC50s for ClfA001, ClfA002, and ClfA004 in a fibrinogen binding inhibition assay that are within 2 μg/ml of each other. In certain instances, the antibody or antigen-binding fragment thereof that binds to *S. aureus* ClfA has IC50s for ClfA001, ClfA002, and ClfA004 in a fibrinogen binding inhibition assay that are all between 1 μg/ml and 5 μg/ml. In certain instances, the antibody or antigen-binding fragment thereof that binds to *S. aureus* ClfA has binding affinities ($K_D$) for ClfA001, ClfA002, and ClfA004 that are all between 200 and 350 pM. In certain instances, the antibody or antigen-binding fragment thereof that binds to *S. aureus* ClfA has binding affinities ($K_D$) of less than 1 nM for all ClfA genotypes. In certain instances, the antibody or antigen-binding fragment that binds to *S. aureus* ClfA has a monomer purity that decreases by no more than 5% after exposure of the antibody or antigen-binding fragment to conventional white light at 2 kLux/hr at 23° C. for 14 days.

In certain instances of the method, composition, antibody or antigen-binding fragment thereof, or use provided herein, the antibody or antigen-binding fragment thereof that binds to at least one *S. aureus* leukotoxin binds to LukF, LukD, and/or HlgB, and/or wherein the antibody or antigen-binding fragment thereof neutralizes LukF, LukD, and/or HlgB. In certain instances, the antibody or antigen-binding fragment thereof that binds to at least one *S. aureus* leukotoxin binds to LukF, LukD, and HlgB, and/or wherein the antibody or antigen-binding fragment thereof neutralizes LukF, LukD, and HlgB. In certain instances, the antibody or antigen-binding fragment thereof that binds to at least one *S. aureus* leukotoxin binds to the same *S. aureus* leukotoxin epitope as an antibody comprising a VH comprising the amino acid sequence of SEQ ID NO:32 and a VL comprising the amino acid sequence of SEQ ID NO:46. In certain instances, the antibody or antigen-binding fragment thereof that binds to at least one *S. aureus* leukotoxin competitively inhibits binding of an antibody comprising a VH comprising the amino acid sequence of SEQ ID NO:32 and a VL comprising the amino acid sequence of SEQ ID NO:46 to the *S. aureus* leukotoxin. In certain instances, the antibody or antigen-binding fragment thereof that binds to at least one *S. aureus* leukotoxin comprises a VHCDR1 comprising the amino acid sequence of SEQ ID NO:7, a VH CDR2 comprising the amino acid sequence of SEQ ID NO:8, a VH CDR3 comprising the amino acid sequence of SEQ ID NO:9, a VL CDR1 comprising the amino acid sequence of SEQ ID NO:16, a VL CDR2 comprising the amino acid sequence of SEQ ID NO:17, and a VL CDR3 comprising the amino acid sequence of SEQ ID NO:18. In certain instances, the antibody or antigen-binding fragment thereof that binds to at least one *S. aureus* leukotoxin comprises a VH comprising the amino acid sequence of SEQ ID NO:32. In certain instances, the antibody or antigen-binding fragment thereof that binds to at least one *S. aureus* leukotoxin comprises a VL comprising the amino acid sequence of SEQ ID NO:46. In certain instances, the antibody or antigen-binding fragment thereof that binds to at least one *S. aureus* leukotoxin comprises a heavy chain comprising the amino acid sequence of SEQ ID NO:50. In certain instances, the antibody or antigen-binding fragment thereof that binds to at least one *S. aureus* leukotoxin comprises a light chain comprising the amino acid sequence of SEQ ID NO:54. In certain instances, the antibody or antigen-binding fragment thereof that binds to at least one *S. aureus* leukotoxin comprises the VH CDR1, VH CDR2, VH CDR3, VL CDR1, VL CDR2, and VL CDR3 of SAN481-SYT. In certain instances, the CDRs are the Kabat-defined CDRs, the Chothia-defined CDRs, or the AbM-defined CDRs. In certain instances, the antibody or antigen-binding fragment that binds to at least one *S. aureus* leukotoxin further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region. In certain instances, the antibody or antigen-binding fragment that binds at least one *S. aureus* leukotoxin further comprises a light chain constant region. In certain instances, the light chain constant region is selected from the group consisting of human immunoglobulin IgGκ and IgGλ light chain constant regions. In certain instances, the light chain constant region is a human IgGκ light chain constant region. In certain instances, the antibody or antigen-binding fragment thereof that binds to at least one S. aureus leukotoxin is an IgG antibody or antigen-binding fragment thereof. In certain instances, the antibody or antigen-binding fragment thereof that binds to at least one S. aureus leukotoxin comprises an Fc region that has been engineered to improve half-life. In certain instances, the antibody or antigen-binding fragment thereof that binds to at least one S. aureus leukotoxin comprises an Fc region with a YTE mutation. In certain instances, the antibody or antigen-binding fragment that binds to at least one S. aureus leukotoxin is a monoclonal antibody or antigen-binding fragment. In certain instances, the antibody or antigen-binding fragment that binds to at least one S. aureus leukotoxin is a full-length antibody. In certain instances, the antibody or antigen-binding fragment that binds to at least one S. aureus leukotoxin is an antigen-binding fragment. In certain instances, the antigen-binding fragment comprises a Fab, Fab', F(ab')$_2$, single chain Fv (scFv), disulfide linked Fv, intrabody, IgGΔCH2, minibody, F(ab')$_3$, tetrabody, triabody, diabody, DVD-Ig, Fcab, mAb$^2$, (scFv)$_2$, or scFv-Fc. In certain instances, the antibody or antigen-binding fragment thereof that binds to at least one S. aureus leukotoxin has an affinity of less than 75 pM for S. aureus LukF, LukD, and HlgAB. In certain instances, the antibody or antigen-binding fragment thereof that binds to at least one S. aureus leukotoxin has similar binding affinities for LukF, LukD, and HlgB.

In certain instances of a method, composition, antibody or antigen-binding fragment thereof, or use provided herein, the S. aureus infection is sepsis. In certain instances of a method, composition, antibody or antigen-binding fragment thereof, or use provided herein, the S. aureus infection is bacteremia. In certain instances of a method, composition, antibody or antigen-binding fragment thereof, or use provided herein, the S. aureus infection is pneumonia. In certain instances of a method, composition, antibody or antigen-binding fragment thereof, or use provided herein, the S. aureus infection is pneumonia the S. aureus infection is ICU pneumonia. In certain instances of a method, composition, antibody or antigen-binding fragment thereof, or use provided herein, the S. aureus infection is a skin or soft tissue infection (SSTI). In certain instances of a method, composition, antibody or antigen-binding fragment thereof, or use provided herein, the S. aureus infection is a diabetic infection of the lower limbs. In certain instances of a method, composition, antibody or antigen-binding fragment thereof, or use provided herein, the S. aureus infection is a diabetic foot ulcer (DFU). In certain instances, the DFU is uninfected. In certain instances, the DFU is infected. In certain instances, the DFU is a grade 1, 2 or 3 DFU. In certain instances of a method, composition, antibody or antigen-binding fragment thereof, or use provided herein, the S. aureus infection is a bone or joint infection. In certain instances of a method, composition, antibody or antigen-binding fragment thereof, or use provided herein, the S. aureus infection is a joint infection, a device infection, a wound infection, a surgical site infection, or osteomyelitis.

In certain instances of a method, composition, antibody or antigen-binding fragment thereof, or use provided herein, the subject is a surgical subject.

In certain instances of a method, composition, antibody or antigen-binding fragment thereof, or use provided herein, the S. aureus infection comprises antibiotic-resistant S. aureus.

In certain instances of a method, composition, antibody or antigen-binding fragment thereof, or use provided herein, the subject has diabetes. In certain instances of a method, composition, antibody or antigen-binding fragment thereof, or use provided herein, the subject is human.

In certain instances of a method, composition, antibody or antigen-binding fragment thereof, or use provided herein, the treating or preventing an S. aureus infection comprises inhibiting S. aureus agglutination, toxin neutralization, inducing opsonophagocytosis, inhibiting S. aureus fibrinogen binding, inhibiting S. aureus agglutination, inhibiting thromboembolic lesion formation, inhibiting S. aureus-associated sepsis, or any combination of the foregoing.

In certain instances of a method, composition, antibody or antigen-binding fragment thereof, or use provided herein, the antibody or antigen-binding fragment thereof that binds to S. aureus AT and the antibody or antigen-binding fragment thereof that binds to S. aureus ClfA are administered in the same pharmaceutical composition. In certain instances of a method, composition, antibody or antigen-binding fragment thereof, or use provided herein, the antibody or antigen-binding fragment thereof that binds to S. aureus AT and the antibody or antigen-binding fragment thereof that binds to S. aureus ClfA are administered in the separate pharmaceutical compositions. In certain instances of a method, composition, antibody or antigen-binding fragment thereof, or use provided herein, the antibody or antigen-binding fragment thereof that binds to S. aureus AT and the antibody or antigen-binding fragment thereof that binds to at least one S. aureus leukotoxin are administered in the same pharmaceutical composition. In certain instances of a method, composition, antibody or antigen-binding fragment thereof, or use provided herein, the antibody or antigen-binding fragment thereof that binds to S. aureus AT and the antibody or antigen-binding fragment thereof that binds to at least one S. aureus leukotoxin are administered in the separate pharmaceutical compositions. In certain instances of a method, composition, antibody or antigen-binding fragment thereof, or use provided herein, the antibody or antigen-binding fragment thereof that binds to S. aureus ClfA and the antibody or antigen-binding fragment thereof that binds to at least one S. aureus leukotoxin are administered in the same pharmaceutical composition. In certain instances of a method, composition, antibody or antigen-binding fragment thereof, or use provided herein, the antibody or antigen-binding fragment thereof that binds to S. aureus ClfA and the antibody or antigen-binding fragment thereof that binds to at least one S. aureus leukotoxin are administered in the separate pharmaceutical compositions. In certain instances of a method, composition, antibody or antigen-binding fragment thereof, or use provided herein, the separate pharmaceutical compositions are administered simultaneously. In certain instances of a method, composition, antibody or antigen-binding fragment thereof, or use provided herein, the separate pharmaceutical compositions are administered sequentially. In certain instances of a method, composition, antibody or antigen-binding fragment thereof, or use provided herein, the antibody or antigen-binding fragment thereof that binds to S. aureus AT, the antibody or antigen-binding fragment thereof that binds to S. aureus ClfA, and the antibody or antigen-binding fragment thereof that binds to at least one S. aureus leukotoxin are administered in the same pharmaceutical composition.

Provided herein are also methods of treating or preventing a S. aureus infection in a subject with diabetes comprising administering to the subject an antibody or antigen-binding fragment thereof that binds to S. aureus AT.

Provided herein are also antibodies or antigen-binding fragments thereof that bind to *S. aureus* AT for use in treating or preventing a *S. aureus* infection in a subject with diabetes.

Provided herein are also uses of an antibody or antigen-binding fragment thereof that binds to *S. aureus* AT in the preparation of a medicament for treating or preventing a *S. aureus* infection in a subject with diabetes.

In certain instances of a method, antibody or antigen-binding fragment thereof, or use provided herein, the antibody or antigen-binding fragment thereof that binds to *S. aureus* AT binds to the same *S. aureus* AT epitope as an antibody comprising a VH comprising the amino acid sequence of SEQ ID NO:19 and a VL comprising the amino acid sequence of SEQ ID NO:33.

In certain instances of a method, antibody or antigen-binding fragment thereof, or use provided herein, the antibody or antigen-binding fragment thereof that binds to *S. aureus* AT competitively inhibits binding of an antibody comprising a VH comprising the amino acid sequence of SEQ ID NO:19 and a VL comprising the amino acid sequence of SEQ ID NO:33 to *S. aureus* AT.

In certain instances of a method, antibody or antigen-binding fragment thereof, or use provided herein, the antibody or antigen-binding fragment thereof that binds to *S. aureus* AT comprises a VH CDR1 comprising the amino acid sequence of SEQ ID NO:1, a VH CDR2 comprising the amino acid sequence of SEQ ID NO:2, a VH CDR3 comprising the amino acid sequence of SEQ ID NO:3, a VL CDR1 comprising the amino acid sequence of SEQ ID NO:10, a VL CDR2 comprising the amino acid sequence of SEQ ID NO:11, and a VL CDR3 comprising the amino acid sequence of SEQ ID NO:12.

In certain instances of a method, antibody or antigen-binding fragment thereof, or use provided herein, the antibody or antigen-binding fragment thereof that binds to *S. aureus* AT comprises a VH comprising the amino acid sequence of SEQ ID NO:19.

In certain instances of a method, antibody or antigen-binding fragment thereof, or use provided herein, the antibody or antigen-binding fragment thereof that binds to *S. aureus* AT comprises a VL comprising the amino acid sequence of SEQ ID NO:33.

In certain instances of a method, antibody or antigen-binding fragment thereof, or use provided herein, the antibody or antigen-binding fragment thereof that binds to *S. aureus* AT comprises a heavy chain comprising the amino acid sequence of SEQ ID NO:47.

In certain instances of a method, antibody or antigen-binding fragment thereof, or use provided herein, the antibody or antigen-binding fragment thereof that binds to *S. aureus* AT comprises a light chain comprising the amino acid sequence of SEQ ID NO:52.

In certain instances of a method, antibody or antigen-binding fragment thereof, or use provided herein, the antibody or antigen-binding fragment thereof that binds to *S. aureus* AT comprises the VH CDR1, VH CDR2, VH CDR3, VL CDR1, VL CDR2, and VL CDR3 of MEDI4893. In certain instances, the CDRs are the Kabat-defined CDRs, the Chothia-defined CDRs, or the AbM-defined CDRs.

In certain instances of a method, antibody or antigen-binding fragment thereof, or use provided herein, the antibody or antigen-binding fragment that binds to *S. aureus* AT further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region.

In certain instances of a method, antibody or antigen-binding fragment thereof, or use provided herein, the antibody or antigen-binding fragment that binds to *S. aureus* AT further comprises a light chain constant region. In certain instances, the light chain constant region is selected from the group consisting of human immunoglobulin IgGκ and IgGλ light chain constant regions. In certain instances, the light chain constant region is a human IgGκ light chain constant region.

In certain instances of a method, antibody or antigen-binding fragment thereof, or use provided herein, the antibody or antigen-binding fragment thereof that binds to *S. aureus* AT is an IgG antibody or antigen-binding fragment thereof.

In certain instances of a method, antibody or antigen-binding fragment thereof, or use provided herein, the antibody or antigen-binding fragment thereof that binds to *S. aureus* AT comprises an Fc region that has been engineered to improve half-life.

In certain instances of a method, antibody or antigen-binding fragment thereof, or use provided herein, the antibody or antigen-binding fragment thereof that binds to *S. aureus* AT comprises an Fc region with a YTE mutation.

In certain instances of a method, antibody or antigen-binding fragment thereof, or use provided herein, the antibody or antigen-binding fragment that binds to *S. aureus* AT is a monoclonal antibody or antigen-binding fragment.

In certain instances of a method, antibody or antigen-binding fragment thereof, or use provided herein, the antibody or antigen-binding fragment that binds to *S. aureus* AT is a full-length antibody.

In certain instances of a method, antibody or antigen-binding fragment thereof, or use provided herein, the antibody or antigen-binding fragment that binds to *S. aureus* AT is an antigen-binding fragment. In certain instances, the antigen-binding fragment comprises a Fab, Fab', $F(ab')_2$, single chain Fv (scFv), disulfide linked Fv, intrabody, IgGΔCH2, minibody, $F(ab')_3$, tetrabody, triabody, diabody, DVD-Ig, Fcab, $mAb^2$, $(scFv)_2$, or scFv-Fc.

In certain instances of a method, antibody or antigen-binding fragment thereof, or use provided herein, the antibody or antigen-binding fragment thereof that binds to *S. aureus* AT has an affinity of 80-100 pM for *S. aureus* AT.

In certain instances of a method, antibody or antigen-binding fragment thereof, or use provided herein, the *S. aureus* infection is sepsis. In certain instances of a method, antibody or antigen-binding fragment thereof, or use provided herein, the *S. aureus* infection is bacteremia. In certain instances of a method, antibody or antigen-binding fragment thereof, or use provided herein, the *S. aureus* infection is pneumonia. In certain instances of a method, antibody or antigen-binding fragment thereof, or use provided herein, the *S. aureus* infection is ICU pneumonia. In certain instances of a method, antibody or antigen-binding fragment thereof, or use provided herein, the *S. aureus* infection is a SSTI. In certain instances of a method, antibody or antigen-binding fragment thereof, or use provided herein, the *S. aureus* infection is a diabetic infection of the lower limbs. In certain instances of a method, antibody or antigen-binding fragment thereof, or use provided herein, the *S. aureus* infection is a DFU. In certain instances, the DFU is uninfected. In certain instances, the DFU is infected. In certain instances, the DFU is a grade 1, 2 or 3 DFU. In certain instances of a method, antibody or antigen-binding fragment thereof, or use provided herein, the *S. aureus* infection is a bone or joint infection.

BRIEF DESCRIPTION OF THE SEVERAL VIEWS OF THE DRAWING(S)

FIG. 1 is a schematic showing that a range of animal models supports the use of the combination of antibodies directed against alpha toxin (AT), clumping factor A (ClfA), and leukotoxins to achieve broad strain and disease coverage.

Figure 2:
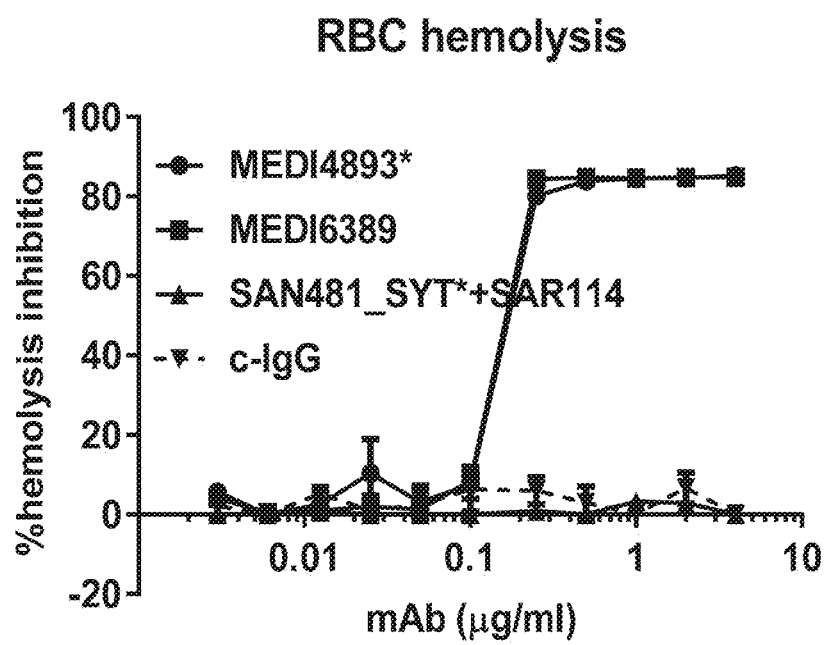
FIG. 2 is a graph showing the efficacy of the combination of antibodies directed against AT, ClfA, and leukotoxins (MEDI6389) in inhibiting red blood cell (RBC) hemolysis as compared to the efficacy of an antibody directed against AT (MEDI4893*) alone and the efficacy of a combination of antibodies directed against ClfA (SAR114) and leukotoxins (SAN481-SYT*). (See Example 1.)

FIG. 5 provides a graph and images showing that the combination of SAN481-SYT* and MEDI4893* is superior to the activity of either SAN481-SYT* or MEDI4893* alone in a dermonecrosis model with a *S. aureus* wound isolate. (See Example 2.)

FIG. 6 provides graphs showing that neutralization of AT, ClfA, and leukotoxins are necessary for protection in the rabbit bacteremia model. (See Example 3.)

FIG. 7 provides graphs comparing the efficacy of the combination of antibodies directed against AT, ClfA, and leukotoxins (MEDI6389) against two different bacterial bloodstream infections: HA-MRSA NRS382 (top panel) and CA-MRSA SF8300 (bottom panel). (See Example 4).

FIG. 8 provides a graph and images showing that a mixed infection of *S. aureus* (SA), *Pseudomonas aeruginosa* (PA), and *Streptococcus pyogenese* (SP) resulted in delayed closure of skin lesions in a diabetic mouse dermonecrosis model compared to an infection by SA alone. The images show lesions at Day 43 post intra-dermal challenge. (See Example 5.)

FIG. 9 provides graphs and images showing that the combination of antibodies directed against AT, ClfA, and leukotoxins (MEDI6389) improves the healing of wounds resulting from mixed-bacteria infections. (See Example 5).

FIG. 10 provides a sequence alignment of HlgB (SEQ ID NO:59), LukF (SEQ ID NO:60), and LukD (SEQ ID NO:61).

FIGS. 11A-G show that elevated glucose levels correlate with more severe *S. aureus* infections. (A and B) After infection with *S. aureus*, diabetic db/db (A) and STZ (B) mice had increased mortality as compared to non-diabetic controls. (C) After infection with *S. aureus*, diabetic db/db mice had similar levels of *S. aureus* in their kidneys as non-diabetic controls. (D) After infection with *S. aureus*, diabetic STZ mice had similar levels of *S. aureus* in their kidneys as non-diabetic controls. (E, F, and G) Treatment with Rosiglitazone for 1 week prior to infection with *S. aureus* reduced circulating glucose (E) and increased survival (F), but did not affect the bacterial burden in the kidney (G). (See Example 7.)

FIGS. 12A-D show that systemic infection of the diabetic host lead to an AT-dependent increase in circulating NETs. (A) After infection with *S. aureus*, ELISA detected increased serum NETs in diabetic mice as compared to non-diabetic controls. (B) Neutralization of *S. aureus* alpha toxin (AT) with the anti-alpha toxin monoclonal antibody MEDI4893* significantly reduced the number of NE-DNA complexes in the serum 48 hours post-infection in diabetic mice. (C) After infection with *S. aureus*, Western blot showed increased citrinulated Histone H3 (H3cit) in diabetic mice as compared to non-diabetic controls. (D) Neutralization of *S. aureus* AT increased survival of diabetic mice infected with *S. aureus*. (See Example 8.)

FIGS. 13A-D show that diabetic db/db mice have increased low density neutrophils (LDNs). (A) After infection with *S. aureus*, the amount of LDNs in the blood of infected diabetic db/db mice was significantly increased as compared to uninfected db/db mice or non-diabetic controls. (B) Treatment with Rosiglitazone for 1 week prior to infection with *S. aureus* reduced LDNs 48 hours post-infection. (C and D) Neutralization of *S. aureus* AT prior to infection reduced LDNs (C) but did not affect overall numbers of neutrophils (D) in diabetic db/db mice. (See Example 9.)

Figure 14:
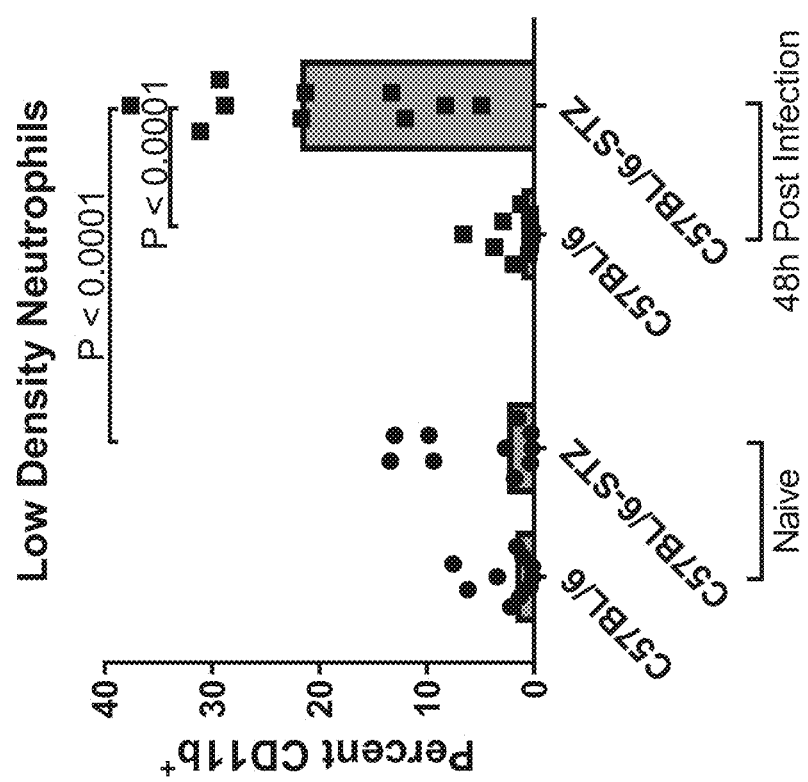

FIG. 14 shows that, after infection with *S. aureus*, diabetic STZ mice had increased low density neutrophils LDNs. (See Example 9.)

FIG. 15A-D shows that delivery of a TGFβ neutralizing antibody prior to infection is protective in diabetic mice (A) TGFβ significantly increased the number of LDNs in diabetic db/db blood, but not in non-diabetic control blood. (B and C) Delivery of a TGFβ neutralizing antibody provided prior to *S. aureus* infection reduced LDNs in blood (B), but did not affect the amount of bacteria in the kidney (C). (D) Delivery of a TGFβ neutralizing antibody provided prior to infection increased survival of diabetic db/db mice. (See Example 10.)

FIGS. 16A-E show that blocking the αVβ6/8 pathway prior to infection is protective in diabetic mice. (A) β8 positive inflammatory monocytes and dendritic cells (DCs) increased in the livers of diabetic db/db mice, not C57BKS mice, following infection. (B) Integrin expression increased on the surface of monocytes, and the overall number of DCs (not the density of β8 on DCs) increased. (C) Neutralizing αVβ6/8 prior to infection decreased LDNs in the blood stream as compared to administration of an anti-αVβ6 antibody or a control antibody (c-IgG). (D) Neutralizing αVβ6/8 prior to infection did not affect the amount of bacteria in the kidney. (E) Neutralizing αVβ6/8 prior to infection increased survival as compared to administration of a control antibody (c-IgG). (See Example 10.)

Figure 17A:
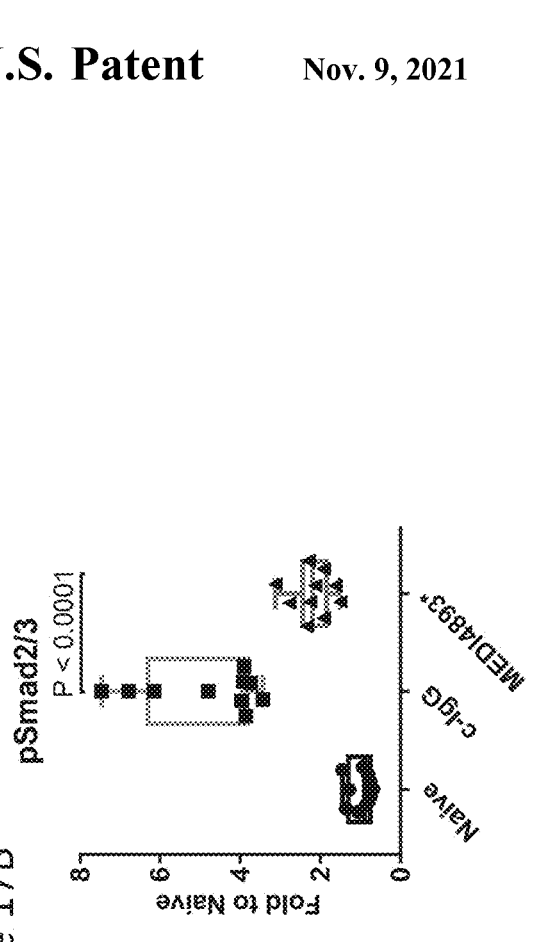
Figure 17B:
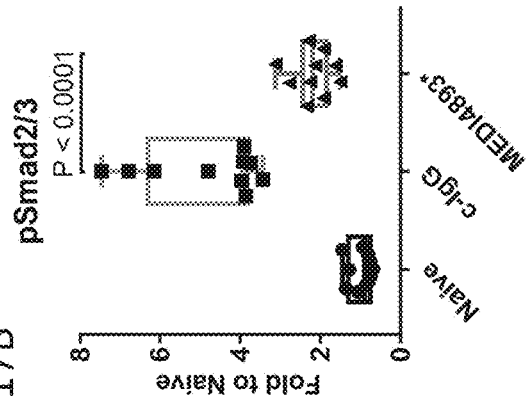
Figure 17C:
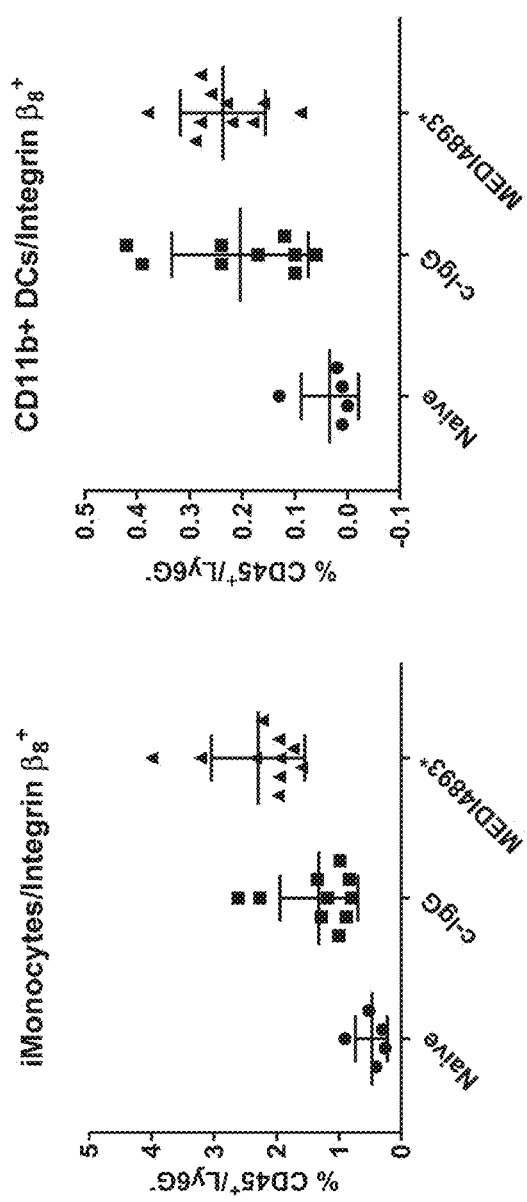

FIGS. 17A-C show that AT influences activation of TGFβ independently of αVβ8 expression on innate immune cells. (A) pSMAD levels were higher in the livers of infected diabetic mice as compared with naïve diabetic mice and infected non-diabetic mice. (B) Neutralizing AT significantly reduced pSMAD levels in the liver. (C) Neutralizing AT did not alter the numbers of αVβ8 expressing innate immune cells. (See Example 11.)

DETAILED DESCRIPTION OF THE INVENTION

The present disclosure provides combinations of antibodies and antigen-binding fragments thereof (e.g., monoclonal antibodies and antigen-binding fragments thereof) that bind to *Staphylococcus aureus* (*S. aureus*) alpha toxin (AT), clumping factor A (ClfA), and at least one leukotoxin. The present disclosure also provides methods of using such combinations, for example, in the treatment or prevention of *S. aureus* infections.

I. Definitions

As used herein, the term "alpha toxin" or "AT" refers to bacterial alpha toxin polypeptides including, but not limited to, native alpha toxin polypeptides and isoforms of alpha toxin polypeptides. "Alpha toxin" encompasses full-length, unprocessed alpha toxin polypeptides as well as forms of alpha toxin polypeptides that result from processing within the cell. As used herein, the term "*S. aureus* alpha toxin" refers to a polypeptide comprising the amino acid sequence of adsdiniktgttdigsnttvktgdlvtydkengmhkkvfysfiddknhnkkl lvirtkgtiagqyrvyseeganksglawpsafkvqlqlpdnevaqisdyyprnsi dtkeymstltygfngnvtgddtgkiggliganvsightlkyvqpdfktilesptd kkvgwkvifnnmvnqnwgpydrdswnpvygnqlfmktrngsmkaadn fldpnkasslIssgfspdfatvitmdrkaskqqtnidviyervrddyqlhwtstn wkgtntkdkwtdrsserykidwekeemtn (SEQ ID NO:57). The *S. aureus* alpha toxin H35L mutant has the sequence ads-diniktgttdigsnttvktgdlvtydkengmlkkvfysfiddknhnkkllvirtkg tiagqyrvyseeganksglawpsafkvqlqlpdnevaqisdyyprnsidtkey mstltygfngnvtgddtgkiggliganvsightlkyvqpdfktilesptdkkvg wkvifnnmvnqnwgpydrdswnpvygnqlfmktrngsmkaadnfldpn kasslIssgfspdfatvitmdrkaskqqtnidviyervrddyqlhwtstnwkgtn tkdkwtdrsserykidwekeemtn (SEQ ID NO:58).

A "alpha toxin polynucleotide," "alpha toxin nucleotide," or "alpha toxin nucleic acid" refer to a polynucleotide encoding alpha toxin.

As used herein, the term "clumping factor A" or "ClfA" refers to bacterial clumping factor A polypeptides including, but not limited to, native clumping factor A polypeptides and isoforms of clumping factor A polypeptides. "Clumping factor A" encompasses full-length, unprocessed clumping factor A polypeptides as well as forms of clumping factor A polypeptides that result from processing within the cell. A "clumping factor A polynucleotide," "clumping factor A nucleotide," or "clumping factor A nucleic acid" refer to a polynucleotide encoding alpha toxin.

As used herein, the term "leukotoxin" refers to bacterial leukotoxin polypeptides including, but not limited to, native leukotoxin polypeptides and isoforms of leukotoxin polypeptides. "Leukotoxin" encompasses a full-length, unprocessed leukotoxin polypeptides as well as forms of leukotoxin polypeptides that result from processing within the cell. Leukotoxins include LukSF, leukotoxin ED (LukED), HlgAB, HlgCB), and leukotoxin AB (LukAB, also known as LukGH). As used herein, the term "*S. aureus* HlgB" refers to a polypeptide comprising the amino acid sequence of SEQ ID NO:59. As used herein, the term "*S. aureus* LukF" refers to a polypeptide comprising the amino acid sequence of SEQ ID NO:60. As used herein, the term "*S. aureus* LukD" refers to a polypeptide comprising the amino acid sequence of SEQ ID NO:61. As used herein, the term "*S. aureus* HlgB" refers to a polypeptide comprising the amino acid sequence of SEQ ID NO:59. (See FIG. 10.) A "leukotoxin polynucleotide," "leukotoxin nucleotide," or "leukotoxin nucleic acid" refer to a polynucleotide encoding a leukotoxin.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or sub-classes (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "monoclonal antibodies," as used herein, refers to antibodies that are produced by a single clone of B-cells and bind to the same epitope. In contrast, the term "polyclonal antibodies" refers to a population of antibodies that are produced by different B-cells and bind to different epitopes of the same antigen.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CHI, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)). The three CDRs, known as CDR1, CDR2, and CDR3, form the "hypervariable region" of an antibody, which is responsible for antigen binding.

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H25-H35B | H26-H32 ... 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\varepsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

A "chimeric" antibody refers to an antibody or fragment thereof comprising both human and non-human regions. A "humanized" antibody is a antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. A fully human antibody does not contain any amino acid residues obtained or derived from a non-human animal. It will be appreciated that fully human and humanized antibodies carry a lower risk for inducing immune responses in humans than mouse or chimeric antibodies (see, e.g., Harding et al., *mAbs,* 2(3): 256-26 (2010)).

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody that "binds to the same epitope" as a reference antibody refers to an antibody that binds to the same amino acid residues as the reference antibody. The ability of an antibody to bind to the same epitope as a reference antibody can determined by a hydrogen/deuterium exchange assay (see Coales et al. Rapid Commun. Mass Spectrom. 2009; 23: 639-647) or x-ray crystallography.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, for example, an antibody that "specifically binds" to a first *S. aureus* leukotoxin may also bind to other *S. aureus* leukotoxins, but the extent of binding to an un-related, non-leukotoxin protein is less than about 10% of the binding of the antibody to the first *S. aureus* leukotoxin as measured, e.g., by a radioimmunoassay (RIA), enzyme-linked immunosorbent assay (ELISA), BiaCore or an octet binding assay.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

An *S. aureus* infection can occur, for example, as a skin or soft tissue infection (SSTI) or bacteremia. *S. aureus* bacteria can travel through the bloodstream and infect a site in the body, resulting in pneumonia, ICU pneumonia, a diabetic infection of the lower limbs, diabetic foot ulcer (DFU), a bone or joint infection, a device infection, a wound infection, a surgical site infection, or osteomyelitis.

"Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al, *Mol. Cell Biol.*, 7: 2031-2034 (1987)). Phage or viral vectors can be introduced into host cells, after growth of infectious particles in suitable packaging cells, many of which are commercially available.

As used herein, the terms "treatment," "treating," and the like, refer to obtaining a desired pharmacologic and/or physiologic effect. In one embodiment, the effect is therapeutic, i.e., the effect partially or completely cures a disease and/or adverse symptom attributable to the disease.

A "therapeutically effective amount" refers to an amount effective, at dosages and for periods of time necessary, to achieve a desired therapeutic result (e.g., treatment of *S. aureus* infection). The therapeutically effective amount may vary according to factors such as the disease state, age, sex, and weight of the individual, and the ability of the antibody or antigen-binding fragment to elicit a desired response in the individual.

A "prophylactically effective amount" refers to an amount effective, at dosages and for periods of time necessary, to achieve a desired prophylactic result (e.g., prevention of *S. aureus* infection or disease onset).

The terms "administer", "administering", "administration", and the like, as used herein, refer to methods that may be used to enable delivery of a drug, e.g., a combination of anti-*S. aureus* antibodies or antigen-binding fragments thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

Administration "in combination with" one or more further therapeutic agents includes simultaneous (concurrent) or consecutive administration in any order.

As used in the present disclosure and claims, the singular forms "a," "an," and "the" include plural forms unless the context clearly dictates otherwise.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-*Staphylococcus aureus* Antibodies and Combinations Thereof

As provided herein, antibodies and antigen-binding fragments thereof (e.g., monoclonal antibodies and fragments) that bind to *S. aureus* proteins can be used in combination. In particular, antibodies and antigen-binding fragments thereof that bind to *S. aureus* alpha toxin (AT) protein, antibodies and antigen-binding fragments thereof that bind to *S. aureus* clumping factor A (ClfA) protein, and antibodies an antigen-binding fragments thereof that bind to at least one *S. aureus* leukotoxin protein can advantageously be used in combination.

Alpha toxin (AT) is a key virulence factor in several *S. aureus* diseases, including pneumonia, skin and soft tissue infections (SSTI), and bacteremia (Bubeck Wardenburg, J. and O. Schneewind, *J. Exp. Med.*, 205: 287-294 (2008); Inoshima et al., *J. Invest. Dermatol.*, 132: 1513-1516 (2012); and Foletti et al., supra). Passive immunization with anti-AT monoclonal antibodies reduced disease severity in pneumonia and dermonecrosis models (Hua et al., *Antimicrob. Agents Chemother.*, 58: 1108-1117 (2014); Tkaczyk et al., *Clin. Vaccine Immunol.*, 19: 377-385 (2012); and Ragle, B. E. and J. Wardenburg Bubeck, *Infect. Immun.*, 77: 2712-2718 (2009)), and vaccination with an AT toxoid containing an H35L mutation (ATH35L) protected against death in mouse lethal bacteremia and pneumonia models (Bubeck Wardenburg, supra, Foletti et al., supra, Hua et al., supra, Ragle, supra, Menzies, B. E. and D. S Kernodle, *Infect. Immun.*, 77: 2712-2718 (2009); and Adhikari et al., *PLoS One*, 7: e38567 (2012)). AT contributes to multiple aspects of *S. aureus* pathogenesis during bacteremia and sepsis, including stimulating a hyperinflammatory response characteristic of sepsis and activating ADAM10-mediated cleavage of endothelial tight junctions, leading to a loss in vascular integrity (Powers et al., *J Infect. Dis.*, 206: 352-356 (2012); Wilke, G. A. and J. Bubeck Wardenburg, *Proc. Natl. Acad. Sci. USA*, 107: 13473-13478 (2010); and Becker et al., *J Innate Immun.*, 6: 619-631 (2014)). AT also has been demonstrated to target platelets, which prevents repair of the injured endothelial barrier and promotes organ dysfunction through platelet-neutrophil aggregate formation (Powers et al., *Cell Host Microbe*, 17: 775-787 (2015)). Alpha toxin structure and function is described in detail in, for example, Bhakdi, S. and J. Tranum-Jensen, *Microbiol. Mol. Biol. Rev.*, 55(4): 733-751 (1991).

Monoclonal and polyclonal antibodies that bind AT are known in the art (see, e.g., Hua et al., *Antimicrob. Agents Chemother.*, 58(2): 1108-1117 (2014); and Oganesyan et al., *J. Biol. Chem.*, 289: 29874-29880 (2014)) and are commercially available from sources such as, for example, Sigma Aldrich (St. Louis, Mo.) and AbCam (Cambridge, Mass.). Exemplary antibodies that bind to AT are disclosed, for example, in WO 2012/109285 and WO 2014/074540 (both of which are herein incorporated by reference in their entireties).

In one instance, an antibody or antigen-binding fragment (e.g., monoclonal antibody or fragment) that specifically binds to *S. aureus* alpha toxin (AT) comprises, consists essentially of, or consists of (i) a heavy chain polypeptide comprising a CDR1 amino acid sequence of SEQ ID NO:1, a CDR2 amino acid sequence of SEQ ID NO:2, and a CDR3 amino acid sequence of SEQ ID NO:3, and (ii) a light chain polypeptide comprising a CDR1 amino acid sequence of SEQ ID NO:10, a CDR2 amino acid sequence of SEQ ID NO:11, and a CDR3 amino acid sequence of SEQ ID NO:12. In another instance, the heavy chain polypeptide of an antibody or antigen-binding fragment (e.g., monoclonal antibody or fragment) that specifically binds to *S. aureus* AT comprises, consists essentially of, or consists of a variable region amino acid sequence of SEQ ID NO:19. In another instance, the light chain polypeptide of an antibody or antigen-binding fragment (e.g., monoclonal antibody or fragment) that specifically binds to *S. aureus* AT comprises, consists essentially of, or consists of a variable region amino acid sequence of SEQ ID NO:33. In another instance, an antibody or antigen-binding fragment (e.g., monoclonal antibody or fragment) that specifically binds to *S. aureus* AT comprises, consists essentially of, or consists of a variable heavy chain comprising, consisting essentially of, or consisting of the amino acid sequence of SEQ ID NO:19 and a light chain variable region comprising, consisting essentially of, or consisting of the amino acid sequence of SEQ ID NO:33. In another instance, an antibody or antigen-binding fragment (e.g., monoclonal antibody or fragment) that specifically binds to *S. aureus* AT comprises, consists essentially of, or consists of a heavy chain comprising, consisting essentially of, or consisting of the amino acid sequence of SEQ ID NO:47 and/or a light chain variable region comprising, consisting essentially of, or consisting of the amino acid sequence of SEQ ID NO:52.

Among the many *S. aureus* surface adhesins, clumping factor A (ClfA) has been demonstrated to play an important role in serious bloodstream infections (Foster et al., *Nat. Rev. Microbiol.*, 12: 49-62 (2014); and Murphy et al., *Hum. Vaccin.*, 7(Suppl): 51-59 (2011)). ClfA binds fibrinogen and facilitates both bacterial adherence to fibrinogen and bacterial clumping, both of which are key attributes in the development of an *S. aureus* bloodstream infection (Vaudaux et al., *Infect. Immun.*, 63: 585-590 (1995); McDevitt et al., *Mol. Microbiol.*, 11: 237-248 (1994); and McDevitt et al., *Eur. J. Biochem.*, 247: 416-424 (1997)). ClfA bound to fibrin or fibrinogen at a site of injury or coated on an indwelling device can facilitate bacterial colonization (Foster et al., supra) and bacterial clumping, which is thought to enhance bacterial invasiveness (McDevitt et al., *Eur. J. Biochem.*, 247: 416-424 (1997); McAdow et al., *PLoS Pathog.*, 7:e1002307 (2011); Flick et al., *Blood*, 121: 1783-1794 (2013); and Rothfork et al., *J. Immunol.*, 171: 5389-5395 (2003)). ClfA also has been reported to impair complement deposition required for opsonophagocytic bacterial killing (OPK) (Hair et al., *Infect. Immun.*, 78: 1717-1727 (2010)). Consistent with these observations, isogenic ΔclfA mutants exhibited reduced virulence in infection models (McAdow et al., supra; Josefsson et al., *PLoS One*, 3: e2206 (2008); and Josefsson et al., *J Infect. Dis.*, 184: 1572-1580 (2001)). In addition, passive immunization with human anti-ClfA-enriched intravenous (i.v.) immunoglobulin (Ig) (INH-A21 or Veronate) or a monoclonal antibody (tefibazumab or Aurexis) improved disease outcomes for patients with *S. aureus* bloodstream infections (Vernachio et al., *Antimicrob. Agents Chemother.*, 47: 3400-3406 (2003); and Vernachio et al., *Antimicrob. Agents Chemother.*, 50: 511-518 (2006)). However, these antibody preparations failed to improve outcomes in clinical studies of prophylaxis or adjunctive therapy with vancomycin to prevent or treat *S. aureus* bacteremia in very-low-birth-weight infants (DeJonge et al., *J. Pediatr.*, 151: 260-265 (2007); Capparelli et al., Antimicrob. Agents Chemother., 49: 4121-4127 (2005); and Bloom et al., *Pediatr. Infect. Dis.*, 24: 858-866 (2005)). ClfA structure and function is described in detail in, for example, McDevitt et al., *Mol. Microbiol.*, 11: 237-248 (1994)).

Monoclonal and polyclonal antibodies which bind ClfA are known in the art (see, e.g., U.S. Pat. No. 7,364,738; Hall et al., *Infect. Immun.*, 71(12): 6864-6870 (2003); and Vernachio et al., *Antimicrob. Agents Chemother.*, 47(11): 3400-3406 (2003)) and are commercially available from sources such as, for example, Creative Biolabs (Shirley, N.Y.). Exemplary antibodies that bind to ClfA are disclosed, for example, in WO 2014/074540 and U.S. 62/702,762 (both of which are herein incorporated by reference in their entireties).

In one instance, an antibody or antigen-binding fragment (e.g., monoclonal antibody or fragment) that specifically binds to *S. aureus* clumping factor A (ClfA) comprises, consists essentially of, or consists of (i) a heavy chain polypeptide comprising a CDR1 amino acid sequence of SEQ ID NO:4, a CDR2 amino acid sequence of SEQ ID NO:5, and a CDR3 amino acid sequence of SEQ ID NO:6, and (ii) a light chain polypeptide comprising a CDR1 amino acid sequence of SEQ ID NO:13, a CDR2 amino acid sequence of SEQ ID NO:14, and a CDR3 amino acid sequence of SEQ ID NO:15. In another instance, the heavy chain polypeptide of an antibody or antigen-binding fragment (e.g., monoclonal antibody or fragment) that specifically binds to *S. aureus* ClfA comprises, consists essentially of, or consists of a variable region amino acid sequence of SEQ ID NO:20. In another instance, the light chain polypeptide of an antibody or antigen-binding fragment (e.g., monoclonal antibody or fragment) that specifically binds to S. aureus ClfA comprises, consists essentially of, or consists of a variable region amino acid sequence of SEQ ID NO:34. In another instance, an antibody or antigen-binding fragment (e.g., monoclonal antibody or fragment) that specifically binds to S. aureus ClfA comprises, consists essentially of, or consists of a variable heavy chain comprising, consisting essentially of, or consisting of the amino acid sequence of SEQ ID NO:20 and a light chain variable region comprising, consisting essentially of, or consisting of the amino acid sequence of SEQ ID NO:34. In certain instances, an antibody or antigen-binding fragment (e.g., monoclonal antibody or fragment) that specifically binds to S. aureus ClfA comprises a heavy chain constant domain comprising the amino acid sequence of CSYHLC (SEQ ID NO:55), MHEACSYHLCQKSLSLS (SEQ ID NO:56), or amino acids 233-454 of SEQ ID NO:49. In another instance, an antibody or antigen-binding fragment (e.g., monoclonal antibody or fragment) that specifically binds to S. aureus ClfA comprises, consists essentially of, or consists of a heavy chain comprising, consisting essentially of, or consisting of the amino acid sequence of SEQ ID NO:49 and/or a light chain variable region comprising, consisting essentially of, or consisting of the amino acid sequence of SEQ ID NO:53.

In another instance, an antibody or antigen-binding fragment (e.g., monoclonal antibody or fragment) that specifically binds to S. aureus ClfA (e.g., an antibody with the CDR, VH and/or VL, or heavy and or light chains of SAR114-N3Y) has IC50's for ClfA001, ClfA002, and ClfA004 in a fibrinogen binding inhibition assay that are within 2 µg/ml of each other. For example, the $IC_{50}$'s of the antibody or antigen-binding fragment thereof for ClfA001, ClfA002, and ClfA004 can all be between 1 µg/ml and 5 µg/ml. The binding affinities ($K_D$) of the antibody or antigen-binding fragment thereof for ClfA001, ClfA002, and ClfA004 can all be all between 200 and 350 pM.

In another instance, an antibody or antigen-binding fragment (e.g., monoclonal antibody or fragment) that specifically binds to S. aureus ClfA (e.g., an antibody with the CDR, VH and/or VL, or heavy and or light chains of SAR114-N3Y) has a monomeric purity that decreases by no more than 5% after exposure to conventional white light at 2 kLux/hr at 23° C. for 14 days.

Leukotoxins are another type of S. aureus virulence factor. Leukotoxins target a broad range of immune cells for destruction. Leukotoxins include Panton-Valentine leukocidin (LukSF-PV also known as LukSF), leukotoxin ED (LukED), gamma hemolysin (which exists as two toxins: HlgAB and HlgCB), and leukotoxin AB (LukAB, also known as LukGH). In certain instances, an antibody or antigen-binding fragment thereof that binds to at least one leukotoxin binds to LukF, LukD, and/or HlgAB. In certain instances, an antibody or antigen-binding fragment thereof that binds to at least one leukotoxin binds to LukF, LukD, and HlgB.

In one instance, an antibody or antigen-binding fragment (e.g., monoclonal antibody or fragment) that specifically binds to at least one S. aureus leukotoxin comprises, consists essentially of, or consists of (i) a heavy chain polypeptide comprising a CDR1 amino acid sequence of SEQ ID NO:7, a CDR2 amino acid sequence of SEQ ID NO:8, and a CDR3 amino acid sequence of SEQ ID NO:9, and (ii) a light chain polypeptide comprising a CDR1 amino acid sequence of SEQ ID NO:16, a CDR2 amino acid sequence of SEQ ID NO:17, and a CDR3 amino acid sequence of SEQ ID NO:18. In another instance, the heavy chain polypeptide of an antibody or antigen-binding fragment (e.g., monoclonal antibody or fragment) that specifically binds to at least one S. aureus leukotoxin comprises, consists essentially of, or consists of a variable region amino acid sequence of SEQ ID NO:32. In another instance, the light chain polypeptide of an antibody or antigen-binding fragment (e.g., monoclonal antibody or fragment) that specifically binds to at least one S. aureus leukotoxin comprises, consists essentially of, or consists of a variable region amino acid sequence of SEQ ID NO:46. In another instance, an antibody or antigen-binding fragment (e.g., monoclonal antibody or fragment) that specifically binds to at least one S. aureus leukotoxin comprises, consists essentially of, or consists of a variable heavy chain comprising, consisting essentially of, or consisting of the amino acid sequence of SEQ ID NO:32 and a light chain variable region comprising, consisting essentially of, or consisting of the amino acid sequence of SEQ ID NO:46. In another instance, an antibody or antigen-binding fragment (e.g., monoclonal antibody or fragment) that specifically binds to at least one S. aureus leukotoxin comprises, consists essentially of, or consists of a heavy chain comprising, consisting essentially of, or consisting of the amino acid sequence of SEQ ID NO:50 and/or a light chain variable region comprising, consisting essentially of, or consisting of the amino acid sequence of SEQ ID NO:54.

Sequences of exemplary anti-AT, anti-ClFA, and anti-leukotoxin antibodies are provided below. Additional anti-AT antibodies are provided, for example, in U.S. Pat. No. 9,527,905, which is herein incorporated by reference in its entirety.) In certain instances, an antibody or antigen-binding fragment thereof described herein binds to AT, ClfA, or at lease one leukotoxin and comprises the six CDRs of an antibody listed in the two tables below (i.e., the three VH CDRs of the antibody listed in the first table and the three VL CDRs of the same antibody listed in the second table).

The anti-AT antibody MEDI4893 is the half-life extended (YTE) version of MEDI4893* or "LC10" described previously in International Patent Application Publications WO 2012/109285 and WO 2014/074540 (both of which are herein incorporated by reference in their entireties). The anti-ClfA antibody SAR114-N3Y is described in U.S. Provisional Application No. 62/702,762. The anti-leukotoxin antibody SAN481-SYT is the half-life extended (YTE) version of SAN481-SYT*. SAN481-SYT* does not contain the YTE mutation.

| VH CDR Amino Acid Sequences | | | | |
|---|---|---|---|---|
| Antibody Name | Antibody Target | VH CDR1 (SEQ ID NO:) | VH CDR2 (SEQ ID NO:) | VH CDR3 (SEQ ID NO:) |
| MEDI4893 and MEDI4893* | AT | SHDMH (SEQ ID NO: 1) | GIGTAGDTYYPD SVKG (SEQ ID NO: 2) | DRYSPTGHYYGMDV (SEQ ID NO: 3) |

| | | VH CDR Amino Acid Sequences | | |
|---|---|---|---|---|
| Antibody Name | Antibody Target | VH CDR1 (SEQ ID NO:) | VH CDR2 (SEQ ID NO:) | VH CDR3 (SEQ ID NO:) |
| SAR114 and SAR114-N3Y | ClfA | NSYWS (SEQ ID NO: 4) | YLYSSGRTNYTPSLKS (SEQ ID NO: 5) | THLGGFHYGGGFWFDP (SEQ ID NO: 6) |
| 11H10 | ClfA | SFAMS (SEQ ID NO: 62) | AISGSGGNTYYADSVKG (SEQ ID NO: 63) | IAFDI (SEQ ID NO: 64) |
| SAN481-SYT and SAN481-SYT* | Leukotoxin | TYAMH (SEQ ID NO: 7) | VTSFDGSNEYYIDSVKG (SEQ ID NO: 8) | DEYTGGWYSVGY (SEQ ID NO: 9) |

| | | VL CDR Amino Acid Sequences | | |
|---|---|---|---|---|
| Antibody | Antibody Target | VL CDR1 (SEQ ID NO:) | VL CDR2 (SEQ ID NO:) | VL CDR3 (SEQ ID NO:) |
| MEDI4893 and MEDI4893* | AT | RASQSISSWLA (SEQ ID NO: 10) | KASSLES (SEQ ID NO: 11) | KQYADYWT (SEQ ID NO: 12) |
| SAR114 and SAR114-N3Y | ClfA | RASQSITSYLN (SEQ ID NO: 13) | ASSSLQS (SEQ ID NO: 14) | QESYSTPPT (SEQ ID NO 15) |
| 11H10 | ClfA | RASQGIRNDLG (SEQ ID NO: 65) | VASSLQS (SEQ ID NO: 66) | LQHNSYPFT (SEQ ID NO: 67) |
| SAN481-SYT and SAN481-SYT* | Leukotoxin | SGSSYNIGSNYVY (SEQ ID NO: 16) | RSIQRPS (SEQ ID NO: 17) | AAWDDSLRAWV (SEQ ID NO: 18) |

In certain instances, an antibody or antigen-binding fragment thereof described herein binds to AT, ClfA, or at least one leukotoxin and comprises the VH of an antibody listed in the following table, e.g., in combination with a VL.

| | | Variable Heavy Chain (VH) Amino Acid Sequence |
|---|---|---|
| Antibody Target | Antibody | VH Amino Acid Sequence (SEQ ID NO) |
| MEDI4893 and MEDI4893* | AT | EVQLVESGGGLVQPGGSLRLSCAASGFTFSSHDMEIWVRQATGKGLEWVSGIGTAGDTYYPDSVKGRFTISRENAKNSLYLQMNSLRAGDTAVYYCARDRYSPTGHYYGMDVWGQGTTVTVSS (SEQ ID NO: 19) |
| SAR114 and SAR114-N3Y | ClfA | QVQLQESGPGLVKPSETLSLTCTVSGGSIQNSYWSWIRQPPGKGLEWIGYLYSSGRTNYTPSLKSRVTISVDTSKNQFSLKLSSVTAADTAVYYCARTHLGGFHYGGGFWFDPWGQGTLVTVSS (SEQ ID NO: 20) |
| 11H10 | ClfA | EVQLLESGGGLVQPGGSLRLSCAASGFTFSSFAMSWVRQAPGKGLEWVSAISGSGGNTYYADSVKGRFTISRDNSKNTLYLQMNSLRAEDTAVYYCAKIAFDIWGQGTMVTVSS (SEQ ID NO: 68) |
| SAR72 | ClfA | EVQLVESGGGLVKPGGSLRVSCAASGFSFRNALMSWVRQAPGKGLEWVGRSKTDGGTTDYAAPVKGRFTISRDDSKNTLYLQMNSLKTEDTAVYYCTTGPGGGPPGDYYYDGMDVWGQGTTVTVSS (SEQ ID NO: 21) |
| SAR80 | ClfA | EVQLVESGGDLVKPGGSLRLSCAASGFTFSDAWMTWVRQAPGKGLEWVGRIRSKTAGGTTDYAAPVKGRFTISRDDSKNTLYLQMTSLKIEDTALYYCMTDGLGLLNFGDSDPHEYWGQGTRVTVSS (SEQ ID NO: 22) |

-continued

Variable Heavy Chain (VH) Amino Acid Sequence

| Antibody Target | Antibody | VH Amino Acid Sequence (SEQ ID NO) |
| --- | --- | --- |
| SAR113 | ClfA | EVQLVQSGAEVKKPGESLKISCKAXGYXFTSYWIGWVRQV PGKGLEWMGIIYPGDSDTRHSPSFQGQVTISVDKSISTAYLQ WSSLKASDSAMYYCARHQSGSHGFDAFEIWGQGTMVTVSS (SEQ ID NO: 23) |
| SAR132 | ClfA | EVQLVQSGAEVKKPGESLKISCKGSGYNFTNYWIAWVRQM PGKGLEWMGIIYSGDSDTRYSPSFLGQVSISVDKSFTTAYLQ WRSLKASDTAMYYCARRPGGQKPYDYWGQGTLVTVSS (SEQ ID NO: 24) |
| SAR352 | ClfA | EVQLVESGGGLVKPGGSLRLSCAASGFTFNNAWMSWVRQA PGKGLEWVGRIKSETAGGTTDYAAPVKGRFSISRDDSRNTL YLEMNSLKTEDTAVYYCTTDSYTPLEEPCPNGVCYTYYYY GMDVWGQGTTVTVSS (SEQ ID NO: 25) |
| SAR372 | ClfA | EVQLVESGGGLVQPGGSLRLSCAASGFIFNRYSMNWVRQA PGKGLEWVSYISSSSSPIYYADSVKGRFTISRDNAKNSLYLQ MNSLRDEDTAVYYCASRVTLGLEFDFWGQGTLVTVSS (SEQ ID NO: 26) |
| SAR510 | ClfA | QVTLRESGPALVKPTQTLTLTCTFSGFSLSTSGMCVGWIRQP PGKALEWLALIEWDDDKYYNTSLKTRLSISKDTSKNQVVLT MTNMDPVDTGTYYCARHSSSSRGFDYWGQGALVTVSS (SEQ ID NO: 27) |
| SAR547 | ClfA | EVQLVQSGAEVKKPGESLKISCKGSGYSFTTYWIAWVRQMP GKGLEWMGIIYPGDSDTRYSPSFQGQVTISADKSTATAYLQ WSSLNASDSAMYYCARQGGSHGYDAFHMWGQGTMVTVS S (SEQ ID NO: 28) |
| SAS1 | ClfA | EVQLLESGGGLVQPGGSLRLSCTASGFTFSTYALNWVRQAP GKGLEWVAGINGTGYNTYYADSVRGRFTISRDNSKNTVTLE MNSLRVEDTATYYCHKVPWWGQGTLVSVSS (SEQ ID NO: 29) |
| SAS19 | ClfA | QVQLQESGPRLVKPSETLSLTCFVSGGSINNSYWTWIRQPPG QGLEWIGFVFSSGRTNYSPSLKSRVTISVDTSKNLFSLRLTSV TAADTAVYFCARQVHYDFWSGYSLTKTNWFDPWGQGTLV TVSS (SEQ ID NO: 30) |
| SAS203 | ClfA | QVQLQESGPGLVKPSETLSLTCVVSGGSINNSYWTWIRQPPG QGLEWIGFVYSSGRTYYSPSLKSRVTISVDTSKNFFSLRLNS VTAADTAVYFCARQVHYDLWSGYSLTKTNWFDPWGQGTL VTVSS (SEQ ID NO: 31) |
| SAN481-SYT and SAN481-SYT* | Leukotoxin | QLQLVESGGGAVQPGRSLKLSCAASGFTFSTYAMHWVRQA PGRGLEWVAVTSFDGSNEYYIDSVKGRFTISRDNTKNTLYL QMTGLRVEDTALYFCARDEYTGGWYSVGYWGQGTLVTVS S (SEQ ID NO: 32) |

In certain instances, an antibody or antigen-binding fragment thereof described herein binds to AT, ClfA, or at least one leukotoxin and comprises the VL of an antibody listed in the following table, e.g., in combination with a VH, optionally the VH of the same antibody listed in the preceding table.

Variable Light Chain (VL) Amino Acid Sequence

| Antibody Target | Antibody | VL Amino Acid Sequence (SEQ ID NO) |
| --- | --- | --- |
| MEDI4893 and MEDI4893* | AT | DIQMTQSPSTLSASVGDRVTITCRASQSISSWLAWYQQKPG KAPKLLIYKASSLESGVPSRFSGSGSGTEFTLTISSLQPDDFAT YYCKQYADYWTFGQGTKVEIK (SEQ ID NO: 33) |
| SAR114 and SAR114-N3Y | ClfA | DIQMTQSPSSLSASVGDRVTITCRASQSITSYLNWYQQKPGK APKLLIYASSSLQSGVPSRFSGSGSGTDFTLTISSLQPEDFATY YCQESYSTPPTFGQGTKVEIK (SEQ ID NO: 34) |
| 11H10 | ClfA | DIQMTQSPSSLSASVGDRVTITCRASQGIRNDLGWYQQ KPGKAPKRLIYVASSLQSGVPSRFSGSGSGTEFTLTISSL QPEDFATYYCLQHNSYPFTFGPGTKVDIK (SEQ ID NO: 69) |

Variable Light Chain (VL) Amino Acid Sequence

| Antibody Target | Antibody | VL Amino Acid Sequence (SEQ ID NO) |
|---|---|---|
| SAR72 | ClfA | SYELTQPPSVSVSPGQTARITCSGDAVPKKYAYWYQQKSGQAPVLVIYEDKKRPSGIPERFSGSSSGTMATLTISGAQVEDEADYYCYSTDSSEGVFGGGTKLTVL (SEQ ID NO: 35) |
| SAR80 | ClfA | SYELTQPPSVSVSPGQTARITCSGDALPKKYAYWYQQKSGQAPVLVIHEDTKRPSGIPERFSGSSSGTMATLTISGAQVEDEADYHCYSTDSSGVVFGGGTKLTVL (SEQ ID NO: 36) |
| SAR113 | ClfA | DIVLTQSPDSLAVSLGERATINCKSSQGVLSRSNNKNYLAWYQQKPGQPPKLLIYWASTRESGVPDRFSGSGSGTDFTLTISSLQAEDVAVYYCQQYYNNLRTFGQGTKVEIR (SEQ ID NO: 37) |
| SAR132 | ClfA | DIQMTQSPSTLSASVGDRVTITCRASQRISNWLAWYQKKPGKAPKLLIYKASTLESEVPSRFSGSGSGTEFTLTISSLQPDDLATYYCHQYISYYTFGQGTKLEIK (SEQ ID NO: 38) |
| SAR352 | ClfA | QSVLTQPPSVSAAPGEKVTISCSGSSSNIGANSVSWYQQFPGTAPKLLIYDNDKRPSGVPDRFSGSKSGTSATLGITGLQTGDEADYYCGTWVGILSAGWVFGGGTKLTVL (SEQ ID NO: 39) |
| SAR372 | ClfA | EIVLTQSPATLSLSPGERATLSCRASQSVSSNLAWYQQKPGQAPRLLIYDASNRATGIPDRFSGSGSGTDFTLTISSLKPEDFAVYYCQLRSNWAYTFGQGTKLEIK (SEQ ID NO: 40) |
| SAR510 | ClfA | SYGLTQPPSVSVSPGQTARITCSGDALAKQYVYWYQQKPGQAPVLVIDKDRERPSGIPERFSGSSSGTTVTLTISGVQAEDEADYYCQSADSSRTYVFGTGTKVTVL (SEQ ID NO: 41) |
| SAR547 | ClfA | DVVMTQSPLSLPVTLGQPASISCRSSQSLVHSDGNTYLNWFQQRPGQSPRRLIYKVSNRDSGVPDRFSGSGSGTDFTLKISRVEAEDVGVYYCMQGTHLTWTFGQGTKVEIK (SEQ ID NO: 42) |
| SAS1 | ClfA | DIVLTQSPESLAVSLGERATISCKSSQSLFFKSNNKNYLAWYQQKPGQPPKVIIYWASTRESGVPARFSGSGSGTDFTLTISSLQAEDVAVYFCHQYYSTQYSFGQGTKLEIK (SEQ ID NO: 43) |
| SAS19 | ClfA | DIQMTQSPSSLSASVGDTVTITCRTSQSISNFLNWYQQKPGKAPKLLIYAASSLQSGVPSRVNGSTSGTEFTLTLSSLQPEDFATYYCQQSYSTPWTFGQGTKVEIK (SEQ ID NO: 44) |
| SAS203 | ClfA | DIQMTQSPSSLSASVGDTVTITCRTSQSISNFLNWYQQKPGKAPKLLIYAASSLQSGVPSRFNGSTSGTDFTLTLSSLQPEDFATYYCQQSYSTPWTFGQGTKVEIK (SEQ ID NO: 45) |
| SAN481-SYT and SAN481-SYT* | Leukotoxin | QSVLTQPPSASGTPGQRVTISCSGSSYNIGSNYVYWYQQFPGTAPKLLISRSIQRPSGVPDRFSGSKSVTSASLAISGLRSEDEADYYCAAWDDSLRAWVFGGGTKLTVL (SEQ ID NO: 46) |

In certain instances, an antibody or antigen-binding fragment thereof described herein binds to AT, ClfA, or at least one leukotoxin and comprises the heavy chain of an antibody listed in the following table, e.g., in combination with a light chain.

Full-length heavy chain amino acid sequences

| Antibody Target | Antibody | Full-Length Heavy Chain Amino Acid Sequence (SEQ ID NO) |
|---|---|---|
| MEDI4893 | AT | EVQLVESGGGLVQPGGSLRLSCAASGFTFSSHDMEIWVRQATGKGLEWVSGIGTAGDTYYPDSVKGRFTISRENAKNSLYLQMNSLRAGDTAVYYCARDRYSPTGHYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGK |

Full-length heavy chain amino acid sequences

| Antibody Target | Antibody | Full-Length Heavy Chain Amino Acid Sequence (SEQ ID NO) |
|---|---|---|
| | | EYKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHYT QKSLSLSPGK (SEQ ID NO: 47) |
| MEDI4893* | AT | EVQLVESGGGLVQPGGSLRLSCAASGFTFSSHDMEIWVRQA TGKGLEWVSGIGTAGDTYYPDSVKGRFTISRENAKNSLYLQ MNSLRAGDTAVYYCARDRYSPTGHYYGMDVWGQGTTVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKRVEPKSCDKTHTCPPCPAPELLGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTKN QVSLTCLVKGFYPSDIAVEWESNGQPENNYKTTPPVLDSDG SFFLYSKLTVDKSRWQQGNVFSCSVMHEALHNHYTQKSLS LSPGK (SEQ ID NO: 48) |
| SAR114-N3Y | ClfA | QVQLQESGPGLVKPSETLSLTCTVSGGSIQNSYWSWIRQPPG KGLEWIGYLYSSGRTNYTPSLKSRVTISVDTSKNQFSLKLSS VTAADTAVYYCARTHLGGFHYGGGFWFDPWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEACSYHLCQKSLSLSP GK (SEQ ID NO: 49) |
| SAR114 | ClfA | QVQLQESGPGLVKPSETLSLTCTVSGGSIQNSYWSWIRQPPG KGLEWIGYLYSSGRTNYTPSLKSRVTISVDTSKNQFSLKLSS VTAADTAVYYCARTHLGGFHYGGGFWFDPWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEALHNHYTQKSLSLSP GK (SEQ ID NO: 70) |
| SAN481-SYT | Leukotoxin | QLQLVESGGGAVQPGRSLKLSCAASGFTFSTYAMHWVRQA PGRGLEWVAVTSFDGSNEYYIDSVKGRFTISRDNTKNTLYL QMTGLRVEDTALYFCARDEYTGGWYSVGYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLYITREPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEALHNHYTQKSLSLSP GK (SEQ ID NO: 50) |
| SAN481-SYT* | Leukotoxin | QLQLVESGGGAVQPGRSLKLSCAASGFTFSTYAMHWVRQA PGRGLEWVAVSFDGSNEYYIDSVKGRFTISRDNTKNTLYL QMTGLRVEDTALYFCARDEYTGGWYSVGYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEALHNHYTQKSLSLSP GK (SEQ ID NO: 51) |

In certain instances, an antibody or antigen-binding fragment thereof described herein binds to AT, ClfA, or at least one leukotoxin and comprises the light chain of an antibody listed in the following table, e.g., in combination with a heavy chain, optionally the heavy chain of the same antibody listed in the preceding table.

| Full-length light chain amino acid sequences | | |
|---|---|---|
| Antibody Target | Antibody | Full-Length Light Chain Amino Acid Sequence (SEQ ID NO) |
| MEDI4893 and MEDI4893* | AT | DIQMTQSPSTLSASVGDRVTITCRASQSISSWLAWYQQK PGKAPKLLIYKASSLESGVPSRFSGSGSGTEFTLTISSLQP DDFATYYCKQYADYWTFGQGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGE (SEQ ID NO: 52) |
| SAR114-N3Y | ClfA | DIQMTQSPSSLSASVGDRVTITCRASQSITSYLNWYQQK PGKAPKLLIYASSSLQSGVPSRFSGSGSGTDFTLTISSLQP EDFATYYCQESYSTPPTFGQGTKVEIKRTVAAPSVFIFPP SDEQLKSGTASVVCLLNNFYPREAKVQWKVDNALQSG NSQESVTEQDSKDSTYSLSSTLTLSKADYEKHKVYACE VTHQGLSSPVTKSFNRGEC (SEQ ID NO: 53) |
| SAN481-SYT and SAN481-SYT* | Leuko-toxin | QSVLTQPPSASGTPGQRVTISCSGSSYNIGSNYVYWYQQ FPGTAPKLLISRSIQRPSGVPDRFSGSKSVTSASLAISGLR SEDEADYYCAAWDDSLRAWVFGGGTKLTVLGQPKAA PSVTLFPPSSEELQANKATLVCLISDFYPGAVTVAWKAD SSPVKAGVETTTPSKQSNNKYAASSYLSLTPEQWKSHR SYSCQVTHEGSTVEKTVAPTECS (SEQ ID NO: 54) |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are combinations of antibodies and antigen-binding fragments thereof that comprise the Chothia VH and VL CDRs of the MEDI4893, SAR114-N3Y, and/or SAN481-SYT antibodies. In certain embodiments, antibodies or antigen-binding fragments thereof comprise one or more CDRs, in which the Chothia and Kabat CDRs have the same amino acid sequence. In certain embodiments, provided herein are antibodies and antigen-binding fragments thereof comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are combinations of antibodies and antigen-binding fragments thereof that comprise the IMGT VH and VL CDRs of MEDI4893, SAR114-N3Y, and/or SAN481-SYT antibodies, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, provided herein are combinations of antibodies or antigen-binding fragments thereof comprise the VH and VL CDRs of the MEDI4893, SAR114-N3Y, and/or SAN481-SYT antibodies determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are combinations of antibodies or antigen-binding fragments that and comprise VH and VL CDRs of the MEDI4893, SAR114-N3Y, and/or SAN481-SYT antibodies as determined by the AbM numbering scheme.

In another aspect, the antibody or antigen-binding fragment thereof (e.g., monoclonal antibody or fragment) described herein can comprise a constant region (Fc) of any suitable class (e.g., IgG, IgA, IgD, IgM, and IgE) that has been modified in order to improve the half-life of the antibody or antigen-binding fragment (e.g., monoclonal antibody or fragment). For example, the antibody or antigen-binding fragment thereof (e.g., monoclonal antibody or fragment) described herein can comprise an Fc that comprises a mutation that extends half-life relative to the same antibody without the mutation.

Fc region engineering is widely used in the art to extend the half-life of therapeutic antibodies and protect from degradation in vivo. In some embodiments, the Fc region of an IgG antibody or antigen-binding fragment can be modified in order to increase the affinity of the IgG molecule for the Fc Receptor-neonate (FcRn), which mediates IgG catabolism and protects IgG molecules from degradation. Suitable Fc region amino acid substitutions or modifications are known in the art and include, for example, the triple substitution M252Y/S254T/T256E (referred to as "YTE") (see, e.g., U.S. Pat. No. 7,658,921; U.S. Patent Application Publication 2014/0302058; and Yu et al., *Antimicrob. Agents Chemother.*, 61(1): e01020-16 (2017)). In certain aspects, an antibody or antigen-binding binding fragment (e.g., monoclonal antibody or fragment) that binds to *S. aureus* AT comprises an Fc region comprising the YTE mutation. In certain aspects, an antibody or antigen-binding binding fragment (e.g., monoclonal antibody or fragment) that binds to at least one *S. aureus* leukotoxin comprises an Fc region comprising the YTE mutation. In certain aspects, an antibody or antigen-binding binding fragment (e.g., monoclonal antibody or fragment) that binds to *S. aureus* AT comprises an Fc region comprising the YTE mutation and an antibody or antigen-binding binding fragment (e.g., monoclonal antibody or fragment) that binds to at least one *S. aureus* leukotoxin comprises an Fc region comprising the YTE mutation.

In another aspect, the Fc region can comprise the sequence CSYHLC (referred to as "N3Y"; SEQ ID NO:55). In certain aspects, an antibody or antigen-binding binding fragment (e.g., monoclonal antibody or fragment) that binds to *S. aureus* ClfA comprises an Fc region comprising the N3Y Fc variant.

In another aspect, the antibody or antigen-binding fragment thereof (e.g., monoclonal antibody or fragment) described herein can comprise a constant region (Fc) of any suitable class (IgG, IgA, IgD, IgM, and IgE) that has been modified in order to improve effector functions (e.g., opsonophagocytic bacterial killing (OPK)), optionally wherein the half-life of the antibody or antigen-binding fragment (e.g., monoclonal antibody or fragment) is also improved. For example, the antibody or antigen-binding fragment thereof (e.g., monoclonal antibody or fragment) described herein may comprise an Fc that comprises a mutation that extends half-life relative to the same antibody without the mutation, and wherein the mutation does not inhibit OPK activity relative to the same antibody or antigen-binding fragment without the mutation. The N3Y Fc variant, in particular, exhibits enhanced pharmacokinetic (PK) properties (e.g., serum persistence) and effector functions (e.g., opsonophagocytic bacterial killing (OPK)) in certain antibodies as compared to the YTE variants.

An antibody or antigen-binding fragment (e.g. monoclonal antibody or fragment) described herein can be, or can be obtained from, a human antibody, a humanized antibody, a non-human antibody, or a chimeric antibody. In one aspect, an antibody described herein, or antigen-binding fragment thereof, is a fully human antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents, human tonsils). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In one embodiment, a humanized antibody can be produced using the methods described in, e.g., U.S. Patent Application Publication 2011/0287485 A1.

III. Nucleic Acids, Vectors, and Host Cells

Also provided herein are one or more isolated nucleic acid sequences that encode the antibody or antigen-binding fragment thereof that binds to AT, the antibody or antigen-binding fragment thereof that binds to ClfA, or the antibody or antigen-binding fragment thereof that binds to at least one leukotoxin (optionally wherein one or more of the antibodies or antigen-binding fragments thereof is a monoclonal antibody or fragment).

The disclosure further provides one or more vectors comprising one or more nucleic acid sequences encoding antibody or antigen-binding fragment thereof that binds to AT, the antibody or antigen-binding fragment thereof that binds to ClfA, and/or the antibody or antigen-binding fragment thereof that binds to at least one leukotoxin (optionally wherein one or more of the antibodies or antigen-binding fragments thereof is a monoclonal antibody or fragment). The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual, 3rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the antibody or antigen-binding fragment thereof that binds to AT, the antibody or antigen-binding fragment thereof that binds to ClfA, and/or the antibody or antigen-binding fragment thereof that binds to at least one leukotoxin (optionally wherein one or more of the antibodies or antigen-binding fragments thereof is a monoclonal antibody or fragment), the vector desirably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

The vector(s) comprising the nucleic acid(s) encoding the antibody or antigen-binding fragment thereof that binds to AT, the antibody or antigen-binding fragment thereof that binds to ClfA, or the antibody or antigen-binding fragment thereof that binds to at least one leukotoxin (optionally wherein one or more of the antibodies or antigen-binding fragments thereof is a monoclonal antibody or fragment) can be introduced into a host cell that is capable of expressing the polypeptides encoded thereby, including any suitable prokaryotic or eukaryotic cell. As such, the present disclosure provides an isolated cell comprising the vector. Host cells that may be used include those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102). Suitable eukaryotic cells are known in the art and include, for example, yeast cells, insect cells, and mammalian cells. In one embodiment, the vector is expressed in mammalian cells. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR– cells (Urlaub et al, *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). The mammalian cell desirably is a human cell. For example, the mammalian cell can be a human lymphoid or lymphoid derived cell line, such as a cell line of pre-B lymphocyte origin, a PER.C6® cell line (Crucell Holland B.V., The Netherlands), or human embryonic kidney (HEK) 293 or 293T cells (ATCC No. CRL1573).

A nucleic acid sequence encoding amino acids of any of the antibodies or antigen-binding fragments (optionally monoclonal antibodies or fragments) described herein can be introduced into a cell by transfection, transformation, or transduction.

IV. Pharmaceutical Compositions and Methods of Using Combinations of Anti-*Staphylococcus aureus* Antibodies The present disclosure provides a composition comprising an effective amount of any one or combination of the antibodies or antigen-binding fragments thereof described herein and a pharmaceutically acceptable carrier. In one embodiment, for example, the composition may comprise a first antibody or antigen-binding fragment thereof (optionally monoclonal) that specifically binds to *S. aureus* alpha toxin protein, as described above, a second antibody or antigen-binding fragment thereof (optionally monoclonal) that specifically binds to *S. aureus* ClfA protein, and a third antibody or antigen-binding fragment thereof (optionally monoclonal) that specifically binds to at least one *S. aureus* leukotoxin, as described above, and a pharmaceutically acceptable carrier. Alternatively, the composition can comprise a pharmaceutically acceptable carrier and any one or any two of (i) an antibody or antigen-binding fragment thereof that specifically binds to *S. aureus* AT, (ii) an antibody or antigen-binding fragment thereof that specifically binds to *S. aureus* ClfA, (iii) an antibody or antigen-binding fragment thereof that specifically binds to at least one *S. aureus* leukotoxin.

In another aspect, the composition may comprise the nucleic acid sequences encoding the AT-binding antibody or antigen-binding fragment, the ClfA-binding antibody or antigen-binding fragment, and/or the leukotoxin-binding antibody or antigen-binding fragment, or one or more vectors comprising such nucleic acid sequences. In one aspect, the composition is a pharmaceutically acceptable (e.g., physiologically acceptable) composition, which comprises a carrier, such as a pharmaceutically acceptable (e.g., physiologically acceptable) carrier and the AT-binding antibody or antigen-binding fragment, the ClfA-binding antibody or antigen-binding fragment, and/or the anti-leukotoxin antibody or antigen-binding fragment nucleic acid sequence(s), or vector(s).

Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

The composition desirably comprises the AT-binding antibody or antigen-binding fragment, the ClfA-binding antibody or antigen-binding fragment, and the leukotoxin-binding antibody or antigen-binding fragment in an amount that is effective to treat or prevent a *S. aureus* infection. In another aspect, the composition comprises the AT-binding antibody or antigen-binding fragment in an amount that is effective to treat or prevent a *S. aureus* infection in combination with the ClfA-binding antibody or antigen-binding fragment, and the leukotoxin-binding antibody or antigen-binding fragment. In another aspect, the composition comprises the ClfA-binding antibody or antigen-binding fragment in an amount that is effective to treat or prevent a *S. aureus* infection in combination with the AT-binding antibody or antigen-binding fragment, and the leukotoxin-binding antibody or antigen-binding fragment. In another aspect, the composition comprises the leukotoxin-binding antibody or antigen-binding fragment in an amount that is effective to treat or prevent a *S. aureus* infection in combination with the AT-binding antibody or antigen-binding fragment, and the ClfA-binding antibody or antigen-binding fragment. In another aspect, the composition comprises the AT-binding antibody or antigen-binding fragment and the ClfA-binding antibody or antigen-binding fragment in an amount that is effective to treat or prevent a *S. aureus* infection in combination with the leukotoxin-binding antibody or antigen-binding fragment. In another aspect, the composition comprises the AT-binding antibody or antigen-binding fragment and the leukotoxin-binding antibody or antigen-binding fragment in an amount that is effective to treat or prevent a *S. aureus* infection in combination with the ClfA-binding antibody or antigen-binding fragment. In another aspect, the composition comprises the ClfA-binding antibody or antigen-binding fragment and the leukotoxin-binding antibody or antigen-binding fragment in an amount that is effective to treat or prevent a *S. aureus* infection in combination with the AT-binding antibody or antigen-binding fragment.

To this end, the disclosed method comprises administering a therapeutically effective amount or prophylactically effective amount of an AT-binding antibody or antigen-binding fragment thereof, a ClfA-binding antibody or antigen-binding fragment thereof, and a leukotoxin-binding antibody or antigen-binding fragment thereof or a composition comprising any one or any combination of the aforementioned antibodies or fragments (including monoclonal antibodies or fragments).

The disclosure provides a method of treating or preventing a *Staphylococcus aureus* (*S. aureus*) infection in a subject (e.g., a human), which comprises administering the AT-binding antibody or antigen-binding fragment, the ClfA-binding antibody or antigen-binding fragment, and/or the leukotoxin-binding antibody or antigen-binding fragment described herein to a subject in need thereof, whereupon the *S. aureus* infection is treated or prevented in the subject. The disclosure also provides use of the AT-binding antibody or antigen-binding fragment, the ClfA-binding antibody or antigen-binding fragment, and/or the leukotoxin-binding antibody or antigen-binding fragment, described herein, or the composition comprising any one or combination of the antibodies or fragments thereof described herein, in the manufacture of a medicament for treating or preventing a *S. aureus* infection.

As discussed herein, *Staphylococcus aureus* is a major human pathogen that causes a wide range of clinical infections. *S. aureus* is a leading cause of bacteremia and infective endocarditis as well as osteoarticular, skin and soft tissue, pleuropulmonary, and device-related infections. Approximately 30% of the human population is colonized with *S. aureus* (Wertheim et al., *Lancet Infect. Dis.*, 5: 751-762 (2005)). The symptoms of *S. aureus* skin infections include, for example, boils, cellulits, and impetigo. *S. aureus* also may cause food poisoning, blood poisoning (also known as bacteremia), toxic shock syndrome, and septic arthritis. The epidemiology, pathophysiology, and clinical manifestations of *S. aureus* infections are described in detail in, e.g., Tong et al., *Clin. Microbiol. Rev.*, 28(3): 603-661 (2015), and the genomes of several different *S. aureus* strains have been sequenced (see, e.g., GenBank/EMBL Accession Nos. BX571856, BX571857, BX571858, FN433596, FN433597, FN433598, HE681097, FR821777, FR821778, FR821779, and FR821780). As discussed herein, the subject (e.g., human subject) can have diabetes.

In certain instances, a therapeutically effective amount of the AT-binding antibody or antigen-binding fragment, the ClfA-binding antibody or antigen-binding fragment, and/or the leukotoxin-binding antibody or antigen-binding fragment, is an amount which inhibits *S. aureus*-associated sepsis, inhibits *S. aureus* agglutination, inhibits thromboembolic lesion formation, neutralizes alpha toxin, neutralizes LukSF, HlgAB, HlgCB and LukED, induces opsonophagocytosis, inhibits *S. aureus* fibrinogen binding, inhibits *S. aureus* agglutination, or any combination of the foregoing, in a human.

Alternatively, the pharmacologic and/or physiologic effect may be prophylactic, i.e., the effect completely or partially prevents a disease or symptom thereof. In this respect, the disclosed method comprises administering a "prophylactically effective amount" of the AT-binding antibody or antigen-binding fragment, the ClfA-binding antibody or antigen-binding fragment, and/or the leukotoxin-binding antibody or antigen-binding fragment, (including monoclonal antibodies or fragments).

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the present disclosure. The desired dosage can be delivered by a single bolus administration of the composition, by multiple bolus administrations of the composition, or by continuous infusion administration of the composition.

The method of treating or preventing a *S. aureus* infection can comprise administering the AT-binding antibody or antigen-binding fragment, the ClfA-binding antibody or antigen-binding fragment, and/or the leukotoxin-binding antibody or antigen-binding fragment in the same composition or in separate compositions. When separate compositions are administered to the subject, each of the compositions can be administered simultaneously or sequentially in any order.

The composition(s) comprising an effective amount of any one or combination of the antibodies described herein, or antigen-binding fragments thereof, the nucleic acid sequence(s) encoding any of the foregoing, or the vector comprising the nucleic acid sequence can be administered to a subject, such as a human, using standard administration techniques, including intravenous, intraperitoneal, subcutaneous, and intramuscular administration routes. The composition may be suitable for parenteral administration. The term "parenteral," as used herein, includes intravenous, intramuscular, subcutaneous, and intraperitoneal administration. In some embodiments, the composition is administered to a subject using peripheral systemic delivery by intravenous, intraperitoneal, or subcutaneous injection.

The AT-binding antibody or antigen-binding fragment, the ClfA-binding antibody or antigen-binding fragment, and/or the leukotoxin-binding antibody or antigen-binding fragment or composition(s) comprising same, can be administered alone or in combination with other drugs (e.g., as an adjuvant) conventionally used for treating *S. aureus* infections. The composition(s) comprising the AT-binding antibody or antigen-binding fragment, the ClfA-binding antibody or antigen-binding fragment, and/or the leukotoxin-binding antibody or antigen-binding fragment can be used in combination with, for example, one or more antibiotics, such as a penicillinase-resistant β-lactam antibiotic (e.g., oxacillin or flucloxacillin). Gentamicin can be used to treat serious infections, such as endocarditis. Most strains of *S. aureus*, however, are now resistant to penicillin, and two in 100 people carry methicillin-resistant strains of *S. aureus* (MRSA). MRSA infections typically are treated with vancomycin, and minor skin infections can be treated with triple antibiotic ointment.

The following examples further illustrate the invention but, of course, should not be construed as in any way limiting its scope.

Example 1

This example demonstrates that antibodies that bind to alpha toxin (AT), clumping factor A (ClfA), and leukotoxins do not interfere with each other's in vitro activities when used in combination.

Several experiments were conducted to determine if using antibodies that bind to AT, ClfA, and leukotoxins in combination would interfere with the activity of any of these individual assays. In these experiments, the MEDI4893*, SAR114, and SAN481-SYT* antibodies were used in combination and are collectively referred to as "MEDI6389."

A red blood cell (RBC) hemolysis inhibition assay was performed to determine if the anti-ClfA SAR114 or the anti-leukotoxin SAN481-SYT* antibodies interfered with the activity of MEDI4893*. Washed rabbit red blood cells (50 µl) were incubated with native alpha toxin (0.1 µg/ml in 25 µl) and serial dilution of 25 µl of MEDI4893*, SAN481 SYT*+SAR114 or mAb trio combination (MEDI6389) as indicated on FIG. 2. Irrelevant mAb c-IgG was used as negative control. After 2 hrs incubation at 37° C., hemoglobin release was measured in 50 ml supernatants at OD450 nm. % hemolysis inhibition was measured as: $100*[(OD_{AT+mAb})/(OD_{AT\,alone})]$. The results, shown in FIG. 2 and in Table 1, below, demonstrate that the use of the three antibodies in combination (MED6389) was about equally effective in inhibiting RBC hemolysis as MEDI4893* alone.

Figure 3:
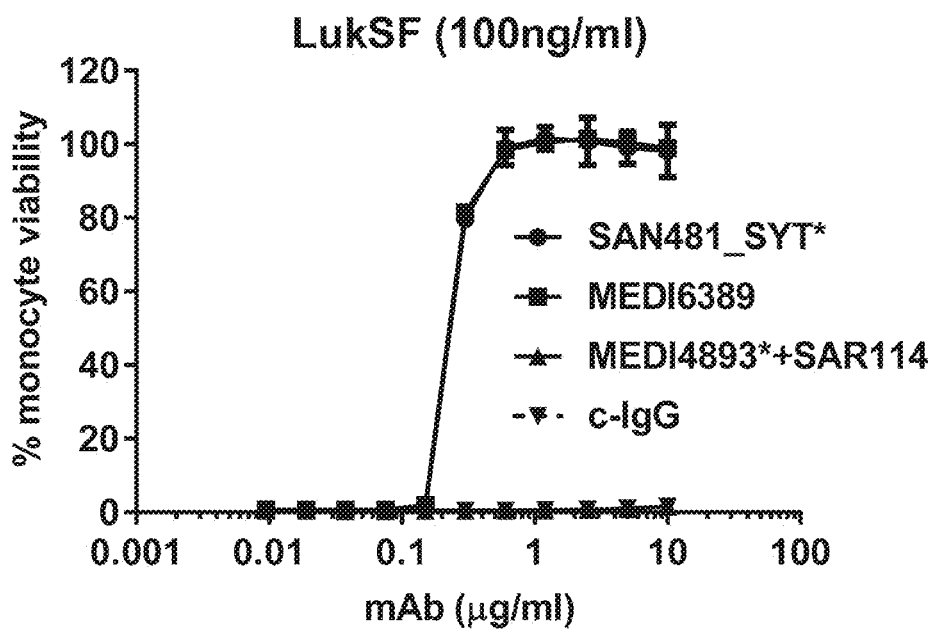
FIG. 3 is a graph showing the efficacy of the combination of antibodies directed against AT, ClfA, and leukotoxins (MEDI6389) in maintaining monocyte viability as compared to the efficacy an antibody directed against leukotoxins (SAN481-SYT*) alone and the efficacy of a combination of antibodies directed against AT (MEDI4893*) and ClfA (SAR114). (See Example 1.)

A monocyte viability assay was performed to determine if the anti-AT MEDI4893* or the anti-ClfA SAR114 antibodies interfered with the activity of SAN481-SYT*. Human monocytic cell line HL-60 (5e4/well/25 µl) were incubated for 2 hrs at 37° C. with a mix of LukS+LukF (100 ng/ml each) and serial dilution as indicated on Figure 3 of SAN481_SYT*, MEDI4893*+SAR114, or mAb trio combination (MEDI6389). Irrelevant mAb c-IgG was used as negative control. Cell viability was quantified by measuring luminescent signal in a Cell Glo assay (Promega) following company instructions. % viability was calculated as followed: $100*[(OD_{cells+LukSF+mAb})/(OD_{cells\,alone})]$. The results, shown in FIG. 3 and in Table 1, below, demonstrate that the use of the three antibodies in combination (MED6389) was about equally effective in maintaining monocyte viability as SAN481-SYT* alone.

Figure 4:
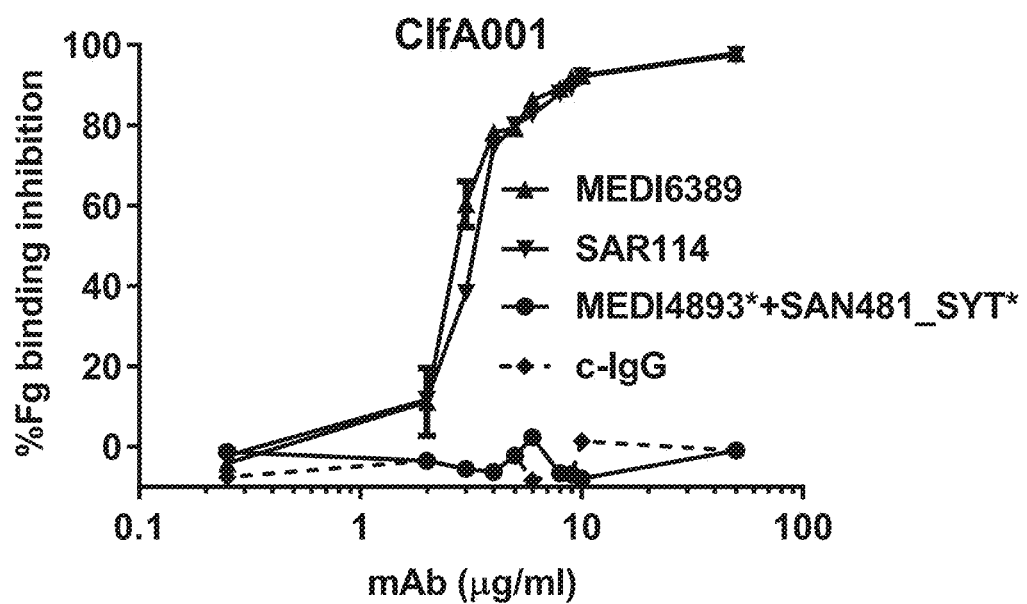
FIG. 4 is a graph showing the efficacy of the combination of antibodies directed against AT, ClfA, and leukotoxins (MEDI6389) in inhibiting fibrinogen (Fg) binding as compared to the efficacy of an antibody directed against ClfA (SAR114) alone and the efficacy of a combination of antibodies directed against AT (MEDI4893*) and leukotoxins (SAN481-SYT*). (See Example 1.)

A fibrinogen-binding inhibition assay was performed to determine if the anti-AT MEDI4893* or the anti-leukotoxin SAN481-SYT* antibodies interfered with the activity of SAR114. Fibrinogen coated 96 well plate (4 µg/ml) was blocked with PBS 2% BSA, and after washes incubated for 1 hr at room temperature with a biotinylated ClfA001 (2 µg/ml) and serial dilution of SAR114, MEDI4893*+ SAN481_SYT*, or mAb trio combination (MEDI6389) as indicated on FIG. 4. After 3 washes, plates were incubated with streptavidin-phycoerythrin at 1:10 000 for 1 hr, and $OD_{450\,nm}$ read following addition of 100 µl TMB, and then 100 µl of $H_2SO_4$ 0.2M. Irrelevant mAb c-IgG was used as negative control. The percentage (%) of fibrinogen binding inhibition was calculated as: $100*[(OD_{ClfA+mAb})/(OD_{ClfA\,alone})]$. The results, shown in FIG. 4 and in Table 1, below, demonstrate that the use of the three antibodies in combination (MED6389) was about equally effective in inhibiting fibrinogen binding as SAR114 alone.

TABLE 1

| IC50 (µg/ml) | MEDI4893* | SAN481-SYT* | SAR114 | MEDI6389 |
|---|---|---|---|---|
| RBC assay | 0.1731 | | | 0.1635 |
| Monocyte viability | | 0.225 | | 0.2246 |
| Fg binding | | | 3.02 | 2.63 |

The use of the combination of the three antibodies (MEDI6389) did not inhibit the activity of MEDI4893 in the RBC assay, the activity of SAN481* in the monocyte viability assay, or the Fg binding of SAR114.

Example 2

This example demonstrates that the combination of antibodies that bind to alpha toxin (AT) and leukotoxins is superior to either antibody alone in a wound healing model.

In these experiments, 6-7 week old female Balb/c mice (n=5) were immunized intra-peritoneally with (i) 0.5 mg/kg a control antibody (c-IgG), (ii) 0.1 mg/kg of the anti-AT antibody MEDI4893*, (iii) 0.5 mg/kg of the anti-leukotoxin antibody SAN481-SYT*, or (iv) both MEDI4893* (0.1 mg/kg) and SAN481-SYT* (0.5 mg/kg). The mice were then intradermally infected 24 hrs later with a wound isolate 1447526 (5e7cfu in 50 µl PBS).

Lesions were monitored over 17 days, and the results are shown in FIG. 5. Lesion sizes were significantly smaller in mice treated with the combination of anti-AT and anti-leukotoxin antibodies than in mice treated with either antibody alone (p<0.05 and indicated with a (*). Pictures on FIG. 5 shows lesions at day 7 post-infection.

Example 3

This example demonstrates that neutralization of alpha toxin (AT), clumping factor A (ClfA), and leukotoxins are all necessary for in vivo protection in the rabbit bacteremia model.

In these experiments, 3-month old female rabbits (n=7) received intravenous administration of (i) a control IgG antibody, (ii) the anti-leukotoxin antibody SAN481-SYT*, (iii) SAN481-SYT* and the anti-ClfA antibody SAR114, (iv) SAR114 and the anti-AT antibody MEDI4893*, (v) SAN481-SYT* and MEDI4893*, or (vi) SAN481-SYT*, SAR114 and MEDI4893*, i.e., MEDI6389. All antibodies were administered at 5 mg/kg, other than the control antibody, which was administered at 15 mg/kg. The rabbits were then infected 12 hours later with intravenous CA-MRSA SF8300.

Survival was monitored over four days after challenge, and the combination of SAN481-SYT*, SAR114 and MEDI4893* (MEDI6389) or MEDI4893*+SAN481_SYT* significantly improved survival over c-IgG as showed by a Log Rank Mantel-Cox statistical test (p=0.0001). The results are shown in FIG. 6. Notably, neither targeting AT and ClfA nor targeting leukotoxins is sufficient for protection in this rabbit lethal bacteremia model.

Example 4

This example demonstrates that neutralization of alpha toxin (AT), clumping factor A (ClfA), and leukotoxins are all necessary for in vivo protection in the rabbit bloodstream infection model.

In these experiments, 3-month old female rabbits (n=12) received intravenous administration of 15 mg/kg of (i) a control IgG antibody, (ii) the anti-leukotoxin antibody SAN481-SYT*, (iii) the anti-ClfA antibody SAR114 and the anti-AT antibody MEDI4893*, (iv) SAN481-SYT* and MEDI4893*, or (vi) SAN481-SYT*, SAR114 and MEDI4893*, i.e., MEDI6389. The rabbits were then infected 12 hours later with intravenous HA-MRSA NRS382 or CA-MRSA SF8300.

Survival was monitored over four days after challenge, and the results are shown in FIG. 7. The combination of SAN481-SYT*, SAR114 and MEDI4893*(MEDI6389) or MEDI4893*+SAN481_SYT* significantly improved survival over c-IgG as showed by a Log Rank Mantel-Cox statistical test (p=0.0015 for NRS382 and p=0.0001 for SF8300) was most effective in increasing survival as a result with either HA-MRSA NRS382 or CA-MRSA SF8300 bacteria.

Example 5

This example demonstrates that a combination of antibodies that bind to alpha toxin (AT), clumping factor A (ClfA), and leukotoxins (MEDI6389) improves wound healing resulting from mixed-bacterial infections in a diabetic mouse dermonecrosis model.

Mixed-bacterial infections were compared to infections caused by a single bacteria in seven week male (n=10) type 2 diabetic mice (BKS.Cg-m+/+Lepr$^{db}$) mice. The mice were infected intra-dermally with a mixture of *S. aureus* (SA; 5e6cfu), *Pseudomonas aeruginosa* (A; 5 cfu) and *Streptococcus pyogenese* (SP; 1e1 cfu) under 50 µl in PBS, or with SA (5e6cfu). The lesion sizes were monitored over 43 days. The results, shown in FIG. 8, demonstrate that the mixed infections result in delay in the time of wound closure in this diabetic mouse dermonecrosis model as compared to infections that result from SA alone.

The effect of the MEDI6389 combination (comprising anti-AT mAb MEDI4893*, anti-ClfA mAb SAR114, and anti-leukotoxin mAb SAN481_SYT*) on the time of wound closure and bacteria load was examined. Mice were passively immunized intra-peritoneally with MEDI6389 (each mAb at 15 mg/kg) or control IgG c-IgG (15 mg/kg) and infected intra-dermally 24 hrs later with SA/SP/PA. Lesions were followed over 43 days, and bacteria counts were enumerated at days 7, 14, and 21 in skin lesions. The results, shown in FIG. 9, demonstrate that MED6389 increases wound healing and decreases bacteria counts in mixed-bacterial skin lesions in this diabetic mouse dermonecrosis model.

Example 6

This example provides the materials and methods used in Examples 7-11.

In vivo Model of Systemic Infection

Frozen stock cultures of *S. aureus* USA300 strain SF8300 were thawed and diluted to the appropriate inoculum in sterile PBS, pH 7.2 (Invitrogen) (Hua et al., *Antimicrob Agents Chemother.* 58:1108-17 (2014)). Specific-pathogen-free 7- to 8-week-old female BKS.Cg-Dok7<m>+/+Lepr, db>/J (db/db), C57BKS, C57BL/6J–STZ, and C57BL/6J mice (The Jackson Laboratory) were briefly anesthetized and maintained in 3% isoflurane (Butler Schein™ Animal Health) with oxygen at 3 L/min and infected intravenously. All bacterial suspensions were administered in 100 µL of PBS. In select experiments, neutralizing antibodies MEDI4893*, anti-αVβ6/8, anti-αVβ6, c-IgG (MedImmune antibodies), anti-TGFβ (clone 1D11.16.8, BioXcell), or control mouse IgG1 were administered (15 mg/kg) in 0.5 mL intraperitoneally (IP) 24 hours prior to infection. Rosiglitazone (Sigma-Aldrich) was administered (10 mg/kg) orally for 7 days. Mice were infected 24 hours following the final dose of rosiglitazone. Animals were euthanized with $CO_2$ at the indicated time points, and blood, liver, or kidneys were collected for analysis. The bacterial load in kidneys was determined by plating serial dilutions on TSA.

NET ELISA

To measure NETs, a hybrid of 2 different ELISA kits were used. Plates were initially coated with anti-elastase capture antibody (R&D Systems). Fresh serum samples were added to the coated wells, then incubated, and washed. Next, anti-DNA-POD antibody (Roche) was used to detect DNA in the captured proteins in the wells. Plates were developed with ABTS solution and ABTS stop solution. Absorbances were measured at 405 nm on a plate reader using SoftMax Pro software.

HDN and LDN Purification

High and low density neutrophils (HDN and LDN) were isolated from whole blood. Following sacrifice, blood was collected and layered over with histopaque 1077 (Sigma-Aldrich). Cells were separated by centrifugation (500 g, 30 minutes). The lower fraction was treated with ACK lysis buffer (Thermo Fisher Scientific) to remove red blood cells from the high density neutrophils. The upper (PBMC) fraction was washed 2× with PBS, and low density neutrophils were isolated with the EasySep Mouse Neutrophil Enrichment Kit (Stemcell Technologies). Purified cell populations were lysed for protein or RNA analysis.

Flow Cytometry

Either whole blood or purified low density cells, were washed twice in ice-cold FACs buffer (PBS with 5% fetal bovine serum, and 0.1% sodium azide). Fc receptors were blocked with anti-mouse CD16/CD32 (eBioscience), and cells were stained with antibodies against mouse CD45 (PE conjugated, clone FA-11), CD11c (APC-Cy5.5 or FITC conjugated, clone N418), CD11b (BV605 conjugated, clone M1/70), Ly6-G (BV421 or PE-Cy7 conjugated, clone 1A8), and Ly6-C. Cells were imaged using the LSR II Flow Cytometer (BD Biosciences) and analyzed with FlowJo. A known concentration of counting beads (Bangs Laboratories) was added to each sample to calculate the number of cells.

Western Blotting

Cells were lysed with Ripa buffer (ThermoFisher Scientific) containing complete protease inhibitor (Sigma) and frozen. In select experiments, IP3R was immunoprecipitated using anti-IP3R (Abcam cat #ab5804) and the Dynabeads protein G immunoprecipitation kit (ThermoFisher Scientific). Equal amounts of protein were separated on 4-12% bis-Tris NuPage gels and transferred to PVDF membranes (ThermoFisher Scientific). Immunodetection was performed using anti-H3Cit (Abcam cat #ab5103), anti-lactoferrin (Abcam cat #ab77705), anti-MMP9 (Abcam cat #ab38898), anti-IP3R (Abcam cat #ab5804), anti-P-Ser/Thr (Abcam cat #ab17464), and anti-actin (Sigma cat #A3854). Proteins were visualized with the Odyssey imaging system (Li-COR).

Example 7

This example demonstrates that elevated glucose levels correlate with more severe *S. aureus* infections.

Figure 11A:
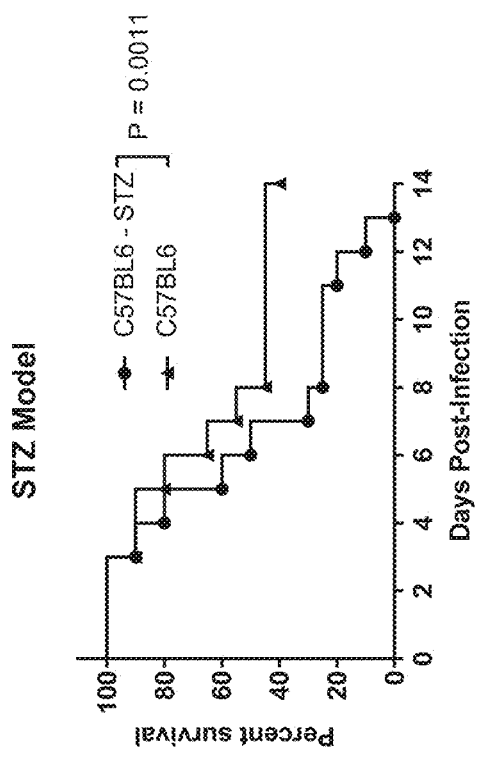
Figure 11C:
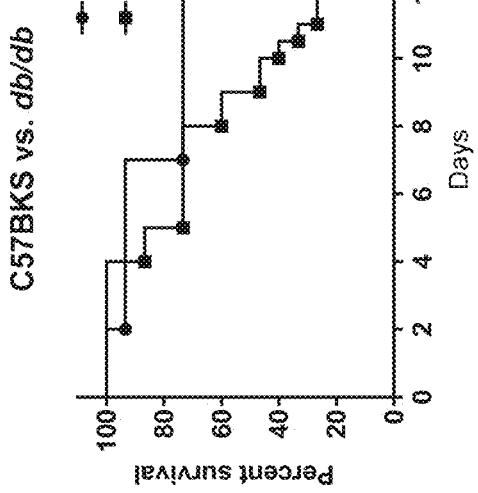
Figure 11B:
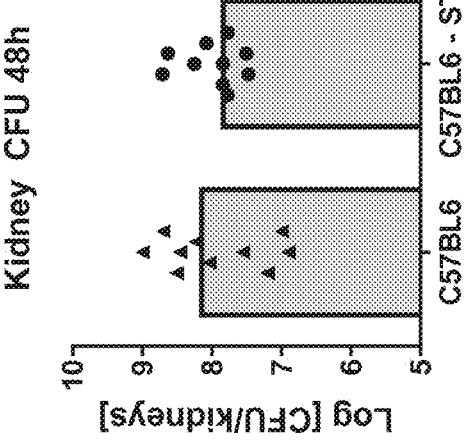
Figure 11D:
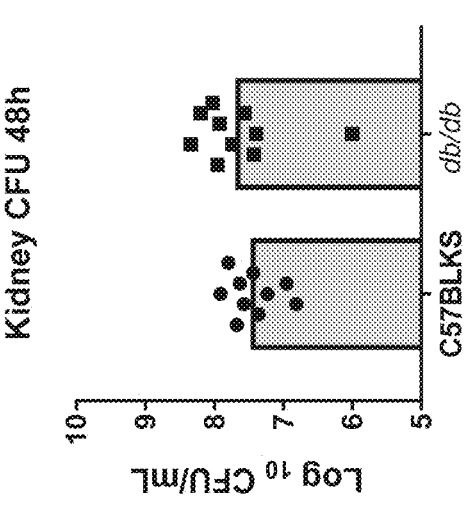

Two models of murine diabetes, STZ induced and db/db, were used to study the effect of diabetes on the systemic response to systemic infection with *S. aureus*. In each model, the diabetic mice had a non-fasting glucose level greater than 450 dg/mL, while non-diabetic control levels were less than 200 dg/mL. Mice were infected with 5e7 CFU *S. aureus* (USA300, SF8300). CFU were collected from the kidney 48 hours post infection, and mortality was monitored for 14 days. Increased mortality was observed in both STZ (P=0.0011) and db/db (P=0.0241) models as compared with non-diabetic control (FIGS. 11A and 11B). Of note, this did not correlate with a difference in bacterial CFU recovered from the kidneys 48 hours post-infection (FIGS. 11C and 11D). To confirm that increased mortality was a consequence of elevated glucose in the diabetic host, mice were treated with Rosiglitazone for 1 week prior to infection to reduce circulating glucose levels (FIG. 11E). Rosiglitazone significantly reduced mortality (P=0.0041) following infection with *S. aureus*, however the bacterial burden in the kidney was unaffected (FIGS. 11F and 11G).

It is notable that no clearance defect was observed in the diabetic mice as compared with non-diabetic controls. This highlights the contribution of excessive inflammation or exaggerated host response to the increase in mortality.

Example 8

This example demonstrates that enhanced NEToisis occurs in diabetic mice.

Figures 12A, 12B, 12C, 12D:

Neutrophils in a diabetic host, or in the presence of elevated glucose levels, are increasingly prone to NETosis. In the diabetic population, NET release has been shown to impair wound healing in mice, and the presence of NETs in the serum correlates with non-healing wounds in patients (Fadini, G. P. et al., *Diabetes* 65: 1061-1071 (2016) and Wong, S. L. et al., *Nat Med* 21: 815-819 (2015)). Neutrophils also release NETs in response to bacterial infection, therefore it was hypothesized that *S. aureus* infection would result in increased systemic NET release in diabetic mice. Complexes of neutrophil elastase and double stranded DNA are used as a measurement of NET formation and quantified by ELISA (Fadini, G. P. et al., *Diabetes* 65: 1061-1071 (2016)). Significant increases (P=0.0003) in serum NETs were observed in diabetic mice intravenously infected with *S. aureus* for 24 hours, while significant increases were not observed in non-diabetic control mice (FIG. 12A). Levels of circulating NETs were not different in uninfected diabetic and non-diabetic mice.

Alpha toxin (AT), once released by *S. aureus*, binds to the receptor ADAM10 on the surface of platelets. (Neutrophils do not express ADAM10.) In response to AT, platelets aggregate and bind to circulating neutrophils, resulting in activation of caspase-1 mediated signaling and NET production (Powers, M. E. et al., *Cell Host Microbe* 17: 775-787 (2015) and Surewaard, B. G. J. et al. *Cell Host Microbe* 24: 271-284 (2018)). Consistent with these findings, neutralization of AT with monoclonal antibody MEDI4893* significantly reduced the number of NE-DNA complexes in the serum 48 hours post-infection in diabetic animals (FIG. 12B). Increased AT-dependent NET production was confirmed 48 hours post-infection by increased citrinulated Histone H3 (H3cit) in the liver as detected by western blot (FIG. 12C) Visualization of liver sections immunohistochemically stained with anti-Ly6G to mark neutrophils and anti-H3 cit also showed increased AT-dependent NET (i.e., less anti-H3 cit staining in the livers of mice that received MEDI4893*) (Cohen T S, et al. *Staphylococcus aureus drives expansion of low density neutrophils in diabetic mice*. JCI 2019 IN PRESS). Neutralization of AT significantly increased survival (P=0.0255) of diabetic mice infected with *S. aureus* (FIG. 12D). These data indicate that systemic infection of the diabetic host lead to an AT-dependent increase in circulating NETs that can be inhibited by MEDI4893*.

Example 9

This example demonstrates that low density neutrophils correlate with increased NETosis.

Similar to macrophages, neutrophils can be separated into different classes based on functional characteristics. Severe burns have been shown to alter the phenotype of circulating neutrophils and to alter TLR expression, cytokine production, and their ability to drive macrophage polarization (Tsuda, Y. et al. *Immunity* 21: 215-226 (2004)). Neutrophils are unique in that they can also be separated by cell density. High density neutrophils are anti-tumor, phagocytic cells, while low density neutrophils are considered pro-tumor phagocytic defective cells (Sagiv, J. Y. et al. *Cell Rep* 10: 562-573 (2015)). While Tsuda et. al. did not measure the density of neutrophils isolated from mice susceptible to *S. aureus* infection, the shape of the nuclei in these neutrophils was similar to the shape of nuclei in low density cells (Sagiv, J. Y. et al. *Cell Rep* 10: 562-573 (2015) and Fridlender, Z. G. et al. *Cancer Cell* 16: 183-194 (2009)). The shapes of the nuclei in neutrophils taken from non-diabetic mice and diabetic mice also had striking differences. The nucleus in cells isolated from non-diabetic mice were multilobular or round, while large numbers of cells with ringed nuclei were observed in the blood of diabetic mice (Cohen T S, et al. *Staphylococcus aureus drives expansion of low density neutrophils in diabetic mice*. JCI 2019 IN PRESS). These structures were similar to those reported by Tsuda et. al to be found in the cells isolated from *S. aureus* susceptible mice, indicating that diabetic mice could have an increased number of low density, or immune impaired neutrophils.

Figures 13A, 13B, 13C, 13D:
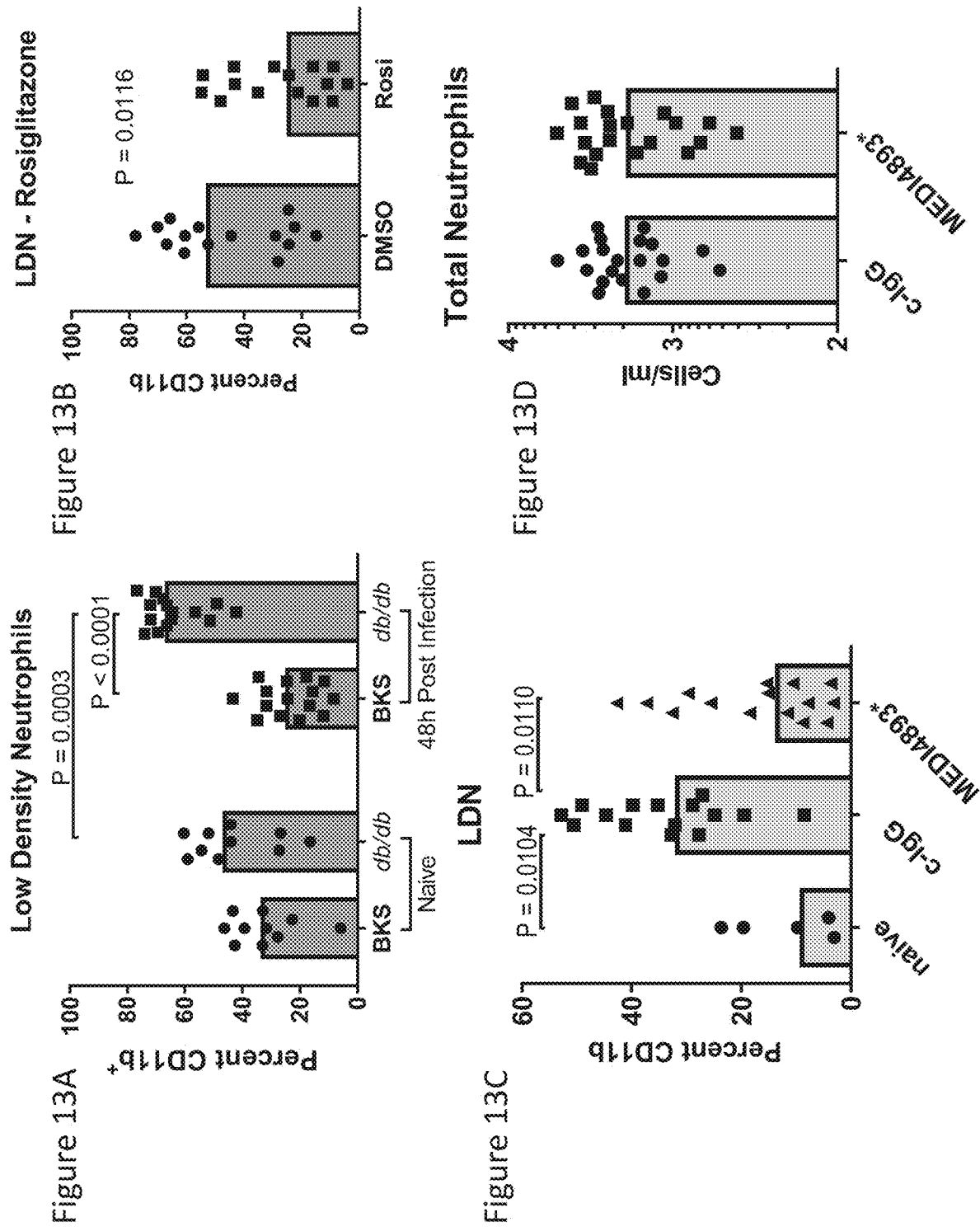

Hyper NET production is a characteristic of low density neutrophils (LDN), and it was hypothesized that higher numbers of LDNs in infected diabetic mice were responsible for the increases in NETs (Villanueva, E. et al. *J Immunol* 187: 538-552 (2011)). Blood was collected from C57BKS and db/db mice 48 hours post-IV infection and was analyzed for presence of LDNs. The amount of LDNs in the blood of infected db/db mice was significantly increased compared to uninfected db/db mice (P<0.0001) as well as infected C57BKS control mice (P=0.0003) (FIG. 13A). Increases in LDNs were not observed in C57BKS mice (FIG. 13A). Similar increases were observed in STZ induced diabetic mice and not in C57BL/6 controls (FIG. 14). Lowering glucose levels with Rosiglitazone prior to infection significantly (P=0.0116) reduced LDNs 48 hours post-infection (FIG. 13B).

To ensure that the observations were not based on degranulated neutrophils, LDNs and high density neutrophils (HDNs) were isolated from the blood of infected db/db mice, and the amounts of lactoferrin (secondary granules) and MMP9 (tertiary granules) were measured by western blot. Equivalent amounts of both were observed, indicating that LDNs have similar granular content as compared to HDNs (Cohen T S, et al. *Staphylococcus aureus drives expansion of low density neutrophils in diabetic mice*. JCI 2019 IN PRESS). Neutralizing AT prevented systemic NET release, therefore the influence of AT on the number of LDNs was assessed. LDNs in the blood of db/db mice treated 24 hours prior to infection with c-IgG or MEDI4893* and infected with *S. aureus* for 48 hours were measured. A significant reduction in LDNs in mice prophylactically treated with MEDI4893* (FIG. 13C) was observed, while overall numbers of neutrophils were not affected (FIG. 13D), indicating that AT contributes to the increase in LDNs.

These data indicate that LDNs contribute to the pathology associated with diabetic *S. aureus* infection and that these LDNs are associated with excessive NET release in both the liver, a key target organ of systemic infections, and systemically in the blood. Moreover, MEDI4893* reduces LDNs in diabetic mice.

Example 10

This example demonstrates that TGFβ drives expansion of LDNs.

Figure 15A:
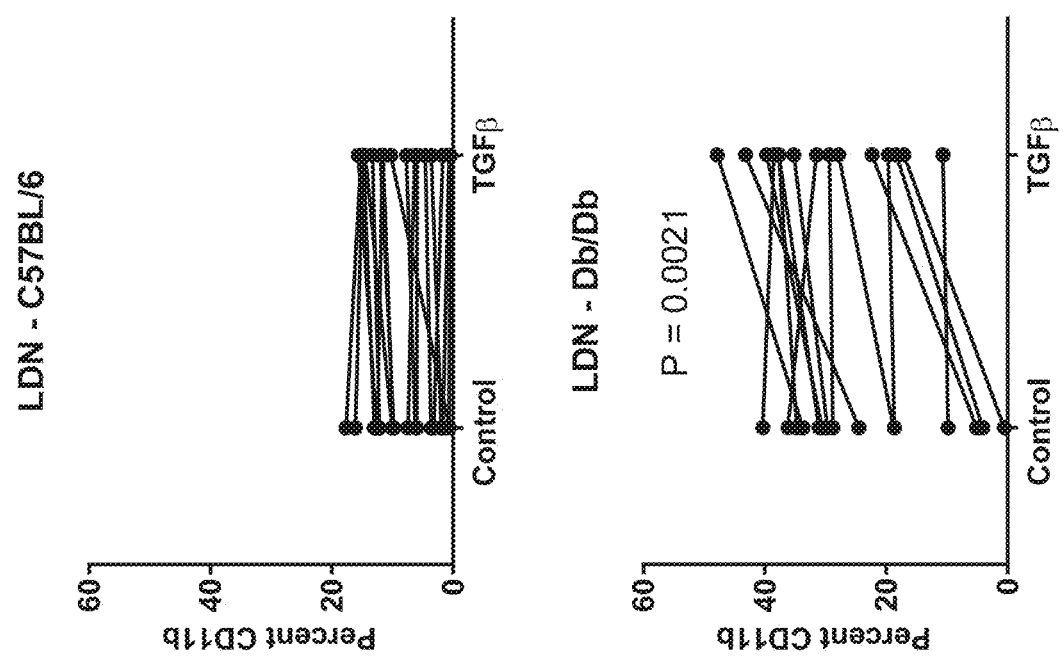
Figure 15B:
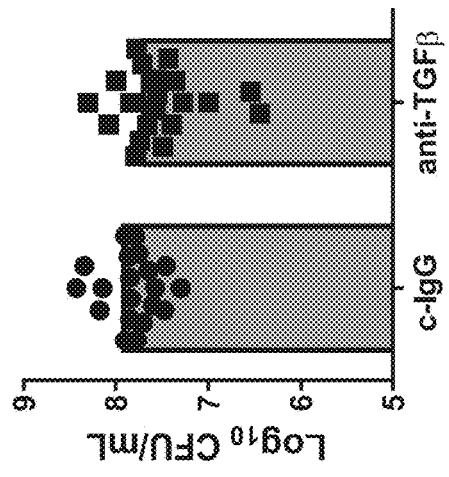
Figure 15C:
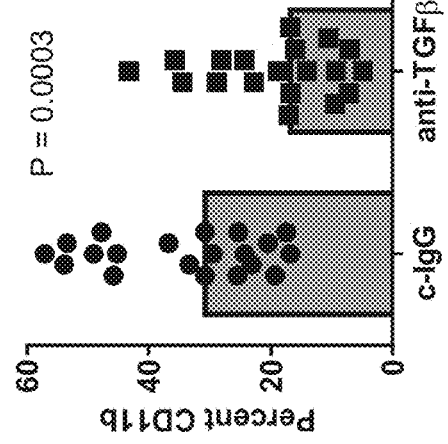
Figure 15D:
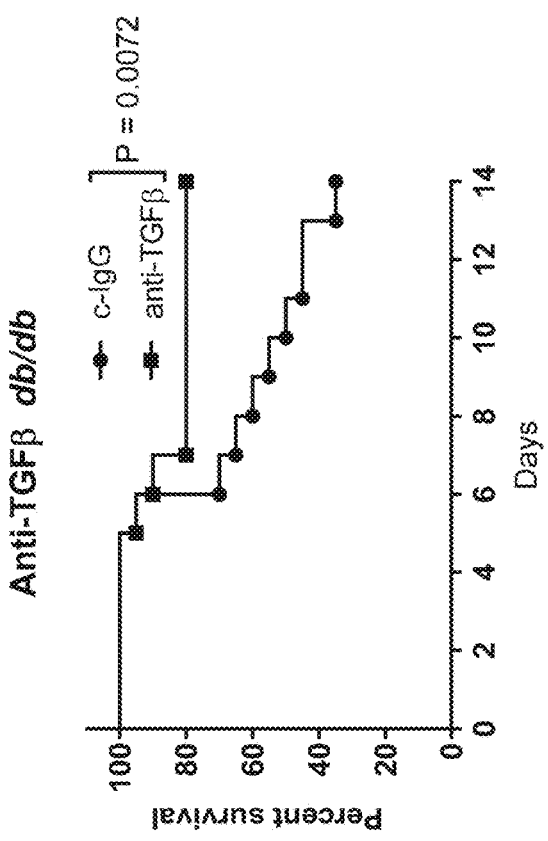

TGFβ has been implicated as a central regulator of neutrophil phenotype, and in tumor models it can drive a phenotypic switch from high to low density neutrophil (Sagiv, J. Y. et al. *Cell Rep* 10: 562-573 (2015) and Fridlender, Z. G. et al. *Cancer Cell* 16: 183-194 (2009). Sagiv et. al. demonstrated that the addition of TGFβ to blood taken from tumor bearing mice, not naïve mice, will increase numbers of LDNs in vitro (id.). This study was repeated with blood from non-diabetic and diabetic mice. The addition of TGFβ to diabetic blood significantly increased (P=0.0021) the number of LDNs (FIG. 15A). The same was not observed in non-diabetic blood. Based on this in vitro evidence demonstrating that TGFβ can increase numbers of LDNs, its necessity for their induction by blocking in vivo was tested. Diabetic mice were prophylactically treated with neutralizing TGFβ antibody 24 hours prior to infection with *S. aureus*. The numbers of LDNs in the bloodstream was significantly reduced (P=0.0003) by inhibition of TGFβ, while numbers of bacteria in the kidneys were similar between groups (FIGS. 15B and 15C). Survival was significantly improved (P=0.0072) by neutralizing TGFβ (FIG. 15D). Visualization of NETs in the liver demonstrated a loss of NETs when TGFβ was neutralized (Cohen T S, et al. *Staphylococcus aureus drives expansion of low density neutrophils in diabetic mice*. JCI 2019 IN PRESS). These data suggest that reducing LDNs by blocking TGFβ could promote survival.

Figure 16C:
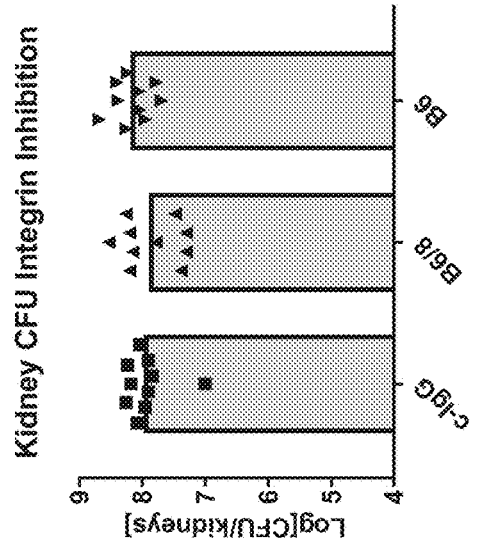
Figure 16D:
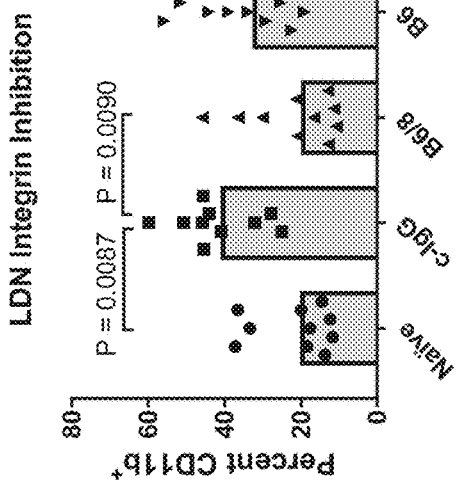
Figure 16E:
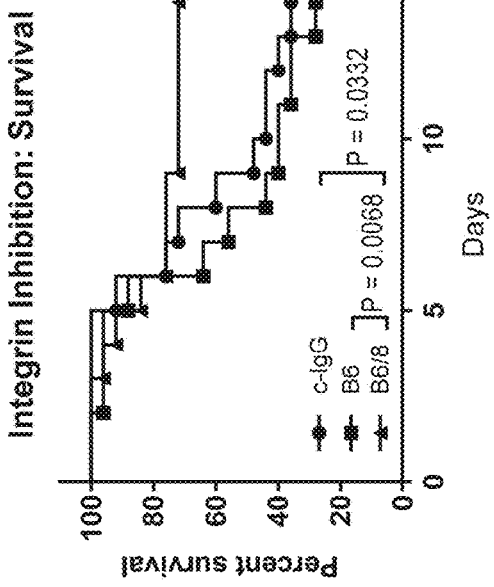

TGFβ is secreted as a pro-form protein (pro-TGFß) and requires cleavage to be activated. Binding of pro-TGFβ by αVβ8 integrin has been linked to its activation and prevention of colitis, and its expression on dendritic cell and monocyte subsets is increased in response to inflammation (Travis, M. A. et al. *Nature* 449: 361-365 (2007) and Kelly, A. et al. *J Exp Med*, doi:10.1084/jem.20171491 (2018)). To determine if *S. aureus* infection influences expression of αVβ8 integrin, innate immune cells were isolated from the liver and spleen of C57BKS and db/db mice 24 hours post-infection, and the expression of αVβ8 was analyzed by flow cytometry. Numbers of β8 positive inflammatory monocytes and dendritic cells increased in the livers of db/db mice, not C57BKS mice, following infection (FIG. 16A). Interestingly, while integrin expression increased on the surface of monocytes, it was the overall number of DCs that increased, not the density of β8 (FIG. 16B). To demonstrate the functional relevance of αVβ8 in this model, mice were prophylactically treated with antibodies neutralizing αVβ6/8, αVβ6 or c-IgG and infected with *S. aureus*. Forty-eight hours post infection LDNs were significantly decreased (P=0.0090) in the bloodstream in the mice treated with αVβ6/8 neutralizing antibody compared with c-IgG (FIG. 16C). Neutralization of αVβ6 alone did not reduce the numbers of these cells. Integrin inhibition did not affect the numbers of bacteria in the kidneys 48 hours post-infection (FIG. 16D). Survival was significantly improved in mice treated with anti-αVß6/8 antibody as compared with c-IgG treated mice (FIG. 16E). Therefore, consistent with directly neutralizing TGFβ, blocking the integrin responsible for activating this pathway was protective in diabetic mice.

These data show that neutralization of either αVß6/8 or TGFβ prevents LDN increases and reduces mortality. These data also show that dendritic cells play a central role in the pathogenesis of diabetic infection due to their ability to activate TGFβ and promote expansion of LDNs.

Example 11

This example demonstrates that AT drives TGFß activation.

It was hypothesized that AT was influencing LDN numbers by affecting the TGFβ pathway. Following its activation, TGFß binds to its receptor complex, activates SMAD transcription factors, and drives expression of downstream genes. Therefore, activation of SMAD signaling is commonly used as a surrogate measurement of TGFβ activation. pSMAD levels were analyzed in the livers of diabetic and non-diabetic mice that were infected (24 hours) with *S. aureus*. Significantly increased pSMAD was observed in the livers of infected diabetic mice as compared to naïve diabetic mice (P<0.0001) and infected non-diabetic mice (P=0.0338) (FIG. 17A). In diabetic mice, MEDI4893* significantly reduced (P<0.0001) pSMAD levels in the liver, indicating that AT was contributing to activation of TGFβ signaling (FIG. 17B). Neutralizing AT did not alter the numbers of αVβ8 expressing innate immune cells (FIG. 17C). These data indicate that AT influences activation of TGFβ through a mechanism that is independent of αVβ8 expression on innate immune cells. Accordingly, neutralization of AT, which is a key *S. aureus* virulence factor, limits activation of TGFβ signaling, and subsequently reduces LDN numbers and NET release.

These data indicate that, in addition to binding to ADAM10 on platelets, AT can act through a second pathway that alters the neutrophil phenotype and subsequent response to *S. aureus* infection. In the diabetic host, AT-dependent activation of TGFß signaling drives expansion of LDNs. Thus, AT is both promoting the expansion of the LDN population which spontaneously release NETs and activating platelets, which can bind and further activate neutrophils.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a *Staphylococcus aureus* (*S. aureus*) infection in a subject comprising administering to the subject (a) an antibody or antigen-binding fragment thereof that binds to *S. aureus* alpha toxin (AT) and comprises a variable heavy chain (VH) comprising the amino acid sequence of SEQ ID NO:19 and a variable light chain (VL) comprising the amino acid sequence of SEQ ID NO:33, (b) an antibody or antigen-binding fragment thereof that binds to *S. aureus* clumping factor A (ClfA) and comprises a VH comprising the amino acid sequence of SEQ ID NO:20 and a VL comprising the amino acid sequence of SEQ ID NO:34, and (c) an antibody or antigen-binding fragment thereof that binds to at least one *S. aureus* leukotoxin and comprises a VH comprising the amino acid sequence of SEQ ID NO:32 and comprises a VL comprising the amino acid sequence of SEQ ID NO:46.

2. The method of claim 1, wherein the antibody or antigen-binding fragment thereof that binds to *S. aureus* ClfA comprises a heavy chain constant domain comprising the amino acid sequence of CSYHLC (SEQ ID NO:55).

3. The method of claim 2, wherein said heavy chain constant domain comprises the amino acid sequence of MHEACSYHLCQKSLSLS (SEQ ID NO:56).

4. The method of claim 1, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, and/or osteomyelitis.

5. The method of claim 1, wherein the treating an *S. aureus* infection comprises inhibiting *S. aureus* agglutination, toxin neutralization, inducing opsonophagocytosis, inhibiting *S. aureus* fibrinogen binding, inhibiting thromboembolic lesion formation, inhibiting *S. aureus*-associated sepsis, or any combination of the foregoing.

6. The method of claim 1, wherein the antibody or antigen-binding fragment thereof that binds to *S. aureus* AT, the antibody or antigen-binding fragment thereof that binds to *S. aureus* ClfA, and/or the antibody or antigen-binding fragment thereof that binds to at least one *S. aureus* leukotoxin are administered in the same pharmaceutical composition.

7. The method of claim 1, wherein the *S. aureus* is antibiotic-resistant *S. aureus*.

8. The method of claim 1, wherein (a) the antibody that binds to *S. aureus* AT is an IgG antibody, (b) the antibody that binds to *S. aureus* ClfA is an IgG antibody, and (c) the antibody that binds to at least one *S. aureus* leukotoxin is an IgG antibody.

9. The method of claim 8, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, and/or osteomyelitis.

10. The method of claim 8, wherein the *S. aureus* is antibiotic-resistant *S. aureus*.

11. The method of claim 1, wherein (a) the antibody that binds to *S. aureus* AT is an IgG1 antibody, (b) the antibody that binds to *S. aureus* ClfA is an IgG1 antibody, and (c) the antibody that binds to at least one *S. aureus* leukotoxin is an IgG1 antibody.

12. The method of claim 11, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, and/or osteomyelitis.

13. The method of claim 11, wherein the *S. aureus* is antibiotic-resistant *S. aureus*.

14. The method of claim 1, wherein (a) the antibody that binds to *S. aureus* AT comprises a heavy chain comprising the amino acid sequence of SEQ ID NO:47 and a light chain comprising the amino acid sequence of SEQ ID NO:52, (b) the antibody that binds to *S. aureus* ClfA comprises a heavy chain comprising the amino acid sequence of SEQ ID NO:49 and a light chain comprising the amino acid sequence of SEQ ID NO:53, and (c) the antibody that binds to at least one *S. aureus* leukotoxin comprises a heavy chain comprising the amino acid sequence of SEQ ID NO:50 and a light chain comprising the amino acid sequence of SEQ ID NO:54.

15. The method of claim 14, wherein the *S. aureus* infection is sepsis, bacteremia, pneumonia, ICU pneumonia, a skin or soft tissue infection (SSTI), a diabetic infection of the lower limbs, a diabetic foot ulcer (DFU), a bone infection, a joint infection, a device infection, a wound infection, a surgical site infection, and/or osteomyelitis.

16. The method of claim 15, wherein the *S. aureus* is antibiotic-resistant *S. aureus*.

17. The method of claim 14, wherein the *S. aureus* is antibiotic-resistant *S. aureus*.

18. The method of claim 14, wherein the *S. aureus* infection is a diabetic foot ulcer (DFU).

19. The method of claim 14, wherein the *S. aureus* infection is a diabetic infection of the lower limbs.

20. The method of claim 1, wherein (a) the antibody that binds to *S. aureus* AT comprises a heavy chain comprising the amino acid sequence of SEQ ID NO:48 and a light chain comprising the amino acid sequence of SEQ ID NO:52, (b) the antibody that binds to *S. aureus* ClfA comprises a heavy chain comprising the amino acid sequence of SEQ ID NO:70 and a light chain comprising the amino acid sequence of SEQ ID NO:53, and (c) the antibody that binds to at least one *S. aureus* leukotoxin comprises a heavy chain comprising the amino acid sequence of SEQ ID NO:51 and a light chain comprising the amino acid sequence of SEQ ID NO:54.

21. The method of claim 1, wherein the *S. aureus* infection is a diabetic foot ulcer (DFU).

22. The method of claim 1, wherein the *S. aureus* infection is a diabetic infection of the lower limbs.

* * * * *